US011141244B2

(12) United States Patent
Kumar et al.

(10) Patent No.: US 11,141,244 B2
(45) Date of Patent: Oct. 12, 2021

(54) OSSEOINTEGRATIVE SURGICAL IMPLANT

(71) Applicant: MAKB Limited, Irvine, CA (US)

(72) Inventors: Ajay Kumar, Palmdale, CA (US); Jonathan Barney, Newport Beach, CA (US)

(73) Assignee: CERAMEDICA, INC., Irvine, CA (US)

(*) Notice: Subject to any disclaimer, the term of this patent is extended or adjusted under 35 U.S.C. 154(b) by 235 days.

(21) Appl. No.: 16/355,600

(22) Filed: Mar. 15, 2019

(65) Prior Publication Data

US 2019/0269484 A1 Sep. 5, 2019

Related U.S. Application Data

(63) Continuation of application No. 14/699,832, filed on Apr. 29, 2015, now abandoned.
(Continued)

(51) Int. Cl.
*A61C 8/00* (2006.01)
*A61C 13/00* (2006.01)
(Continued)

(52) U.S. Cl.
CPC .......... *A61C 8/0015* (2013.01); *A61B 17/866* (2013.01); *A61C 8/0006* (2013.01);
(Continued)

(58) Field of Classification Search
CPC ... A61B 17/866; A61C 8/0006; A61C 8/0012; A61C 8/0013; A61C 8/0015;
(Continued)

(56) References Cited

U.S. PATENT DOCUMENTS

| 4,983,182 A | 1/1991 | Kijima et al. |
| 5,063,003 A | 11/1991 | Gonzalez-Oliver |

(Continued)

FOREIGN PATENT DOCUMENTS

| DE | 4012731 A1 | 10/1990 |
| DE | 19530981 A1 | 8/1995 |

(Continued)

OTHER PUBLICATIONS

International Search Report for Osseointegrative Surgical Implant, International App. No. PCT/US2015/28363, Applicant Osseodyne Surgical Solutions, LLC.
(Continued)

*Primary Examiner* — Matthew M Nelson
(74) *Attorney, Agent, or Firm* — Stetina Brunda Garred & Brucker

(57) ABSTRACT

Embodiments of the present invention provide an osseointegrative implant and related tools, components and fabrication techniques for surgical bone fixation and dental restoration purposes. In one embodiment an all-ceramic single-stage threaded or press-fit implant is provided having finely detailed surface features formed by ceramic injection molding and/or spark plasma sintering of a powder compact or green body comprising finely powdered zirconia. In another embodiment a two-stage threaded implant is provided having an exterior shell or body formed substantially entirely of ceramic and/or CNT-reinforced ceramic composite material. The implant may include one or more frictionally anisotropic bone-engaging surfaces. In another embodiment a densely sintered ceramic implant is provided wherein, prior to sintering, the porous debound green body is exposed to ions and/or particles of silver, gold, titanium, zirconia, YSZ, α-tricalcium phosphate, hydroxyapatite, carbon, carbon nanotubes, and/or other particles which remain
(Continued)

lodged in the implant surface after sintering. Optionally, at least the supragingival portions of an all-ceramic implant are configured to have high translucence in the visible light range. Optionally, at least the bone-engaging portions of an all-ceramic implant are coated with a fused layer of titanium oxide.

14 Claims, 18 Drawing Sheets

Related U.S. Application Data

(60) Provisional application No. 61/986,242, filed on Apr. 30, 2014.

(51) Int. Cl.
 *A61B 17/86* (2006.01)
 *A61C 8/02* (2006.01)
(52) U.S. Cl.
 CPC .............. *A61C 8/006* (2013.01); *A61C 8/008* (2013.01); *A61C 8/0012* (2013.01); *A61C 8/0013* (2013.01); *A61C 8/0022* (2013.01); *A61C 8/0025* (2013.01); *A61C 8/0037* (2013.01); *A61C 8/0039* (2013.01); *A61C 8/0053* (2013.01); *A61C 8/0068* (2013.01); *A61C 8/0075* (2013.01); *A61C 8/0087* (2013.01); *A61C 8/0089* (2013.01); *A61C 13/0003* (2013.01); *A61C 13/0018* (2013.01); *A61C 2008/0046* (2013.01)
(58) Field of Classification Search
 CPC ... A61C 8/0022; A61C 8/0025; A61C 8/0037; A61C 8/0039; A61C 8/0053; A61C 8/006; A61C 8/0068; A61C 8/0075; A61C 8/008; A61C 8/0087; A61C 8/0089; A61C 13/0003; A61C 13/0018; A61C 2008/0046
 USPC ........................................................ 433/174
 See application file for complete search history.

(56) References Cited

U.S. PATENT DOCUMENTS

| | | | |
|---|---|---|---|
| 5,110,513 A | | 5/1992 | Puvilland |
| 5,123,844 A | | 6/1992 | Wakai et al. |
| 5,192,325 A | | 3/1993 | Kijima et al. |
| 5,269,686 A | | 12/1993 | James |
| 5,342,201 A | | 8/1994 | Oden |
| 5,762,499 A | | 6/1998 | Dard et al. |
| 6,168,435 B1 | | 1/2001 | Beaty et al. |
| 6,273,722 B1 | | 8/2001 | Phillips |
| 6,280,193 B1 | | 8/2001 | Peltier |
| 6,592,805 B1 | | 7/2003 | Wang et al. |
| 7,708,559 B2 | | 5/2010 | Wohrle et al. |
| RE41,584 E | | 8/2010 | Ying et al. |
| 8,011,925 B2 | | 9/2011 | Powell et al. |
| 8,397,791 B2 * | | 3/2013 | Wang .................. A61C 8/0018 164/312 |
| 8,408,906 B2 | | 4/2013 | de Wild et al. |
| 8,439,680 B2 | | 5/2013 | Sanchez et al. |
| 8,454,362 B2 | | 6/2013 | Rubbert |
| 8,674,018 B2 | | 3/2014 | ter Maat et al. |
| 8,961,178 B2 | | 2/2015 | Hayashi et al. |
| 9,387,506 B2 | | 7/2016 | Stephan |
| 2002/0037233 A1* | | 3/2002 | Billiet .................... B22F 5/007 419/37 |
| 2003/0058187 A1* | | 3/2003 | Billiet .................... H01Q 1/362 343/895 |
| 2003/0059742 A1 | | 3/2003 | Webster et al. |
| 2004/0016651 A1 | | 1/2004 | Windler |
| 2004/0101807 A1 | | 5/2004 | Porter et al. |
| 2004/0121286 A1 | | 6/2004 | Aravena et al. |
| 2004/0137209 A1 | | 7/2004 | Zeller et al. |
| 2004/0029075 A1 | | 12/2004 | Peltier et al. |
| 2005/0012231 A1 | | 1/2005 | Olsson et al. |
| 2005/0106534 A1 | | 5/2005 | Gahlert |
| 2005/0266380 A1 | | 12/2005 | Soler et al. |
| 2007/0182042 A1 | | 8/2007 | Ikushima et al. |
| 2008/0050699 A1 | | 2/2008 | Zhang et al. |
| 2008/0303181 A1 | | 12/2008 | Holand et al. |
| 2009/0011384 A1 | | 1/2009 | Collins et al. |
| 2009/0042167 A1 | | 2/2009 | Van Der Zel |
| 2010/0038344 A1 | | 2/2010 | Forster et al. |
| 2010/0094420 A1* | | 4/2010 | Grohowski, Jr. ....... B22F 7/002 623/16.11 |
| 2010/0248184 A1 | | 9/2010 | Soler et al. |
| 2011/0003083 A1 | | 1/2011 | Yang et al. |
| 2011/0014586 A1 | | 1/2011 | Jorneus et al. |
| 2011/0045439 A1 | | 2/2011 | Tripodakis et al. |
| 2011/0065064 A1 | | 3/2011 | Kahdermann et al. |
| 2011/0076643 A1 | | 3/2011 | Kandemann |
| 2011/0260349 A1* | | 10/2011 | Rolf .................... C04B 35/6264 264/16 |
| 2011/0269103 A1 | | 11/2011 | Shimko |
| 2011/0318708 A1 | | 12/2011 | Gahlert |
| 2012/0064489 A1 | | 3/2012 | Rubbert et al. |
| 2012/0088649 A1 | | 4/2012 | Frage et al. |
| 2012/0129131 A1 | | 5/2012 | Baehre et al. |
| 2012/0276336 A1 | | 11/2012 | Malshe et al. |
| 2012/0301849 A1* | | 11/2012 | Wang ..................... A61C 13/20 433/174 |
| 2013/0011610 A1 | | 1/2013 | Stephan |
| 2013/0011811 A1 | | 1/2013 | Gourlaouen-Preissler et al. |
| 2013/0150227 A1 | | 6/2013 | Wang et al. |
| 2013/0177468 A1 | | 7/2013 | Hayashi et al. |
| 2013/0177876 A1 | | 7/2013 | Hommann et al. |
| 2013/0236855 A1 | | 9/2013 | Bullis et al. |
| 2013/0266909 A1 | | 10/2013 | Delfosse et al. |
| 2014/0030676 A1 | | 1/2014 | Di Girolamo et al. |
| 2014/0147808 A1 | | 5/2014 | Buurlage |
| 2015/0147724 A1 | | 5/2015 | Staudenmann et al. |
| 2015/0298353 A1* | | 10/2015 | Zhang ....................... B22F 3/12 125/21 |
| 2016/0106524 A1 | | 4/2016 | Gahlert |
| 2019/0269484 A1* | | 9/2019 | Kumar ................. A61C 8/0053 |

FOREIGN PATENT DOCUMENTS

| | | |
|---|---|---|
| DE | 19714178 | 3/2016 |
| EP | 0870478 A1 | 10/1998 |
| EP | 1570804 A1 | 3/2009 |
| TW | 201343143 A | 3/2011 |
| TW | 201238567 A1 | 10/2012 |
| WO | 200134056 A1 | 5/2001 |
| WO | 2004096 A1 | 11/2004 |
| WO | 2009098036 A2 | 8/2009 |
| WO | 2013004361 A2 | 1/2013 |
| WO | 2013126407 A1 | 8/2013 |
| WO | 2013190043 A2 | 12/2013 |

OTHER PUBLICATIONS

Supplementary Partial European Search Report of International Application No. PCT/US2015/028363, filed Apr. 15, 2015, in the name of Ajay Kumar.
European Search Report for Osseointegrative Surgical Implant, International App. No. PCT/US2015/28363, Applicant Osseodyne Surgical Solutions, LLC.
Su Yong Kwon et al., A Large Increase in the Thermal Conductivity of Carbon Nanotube/Polymer Composite Produced by Percolation Phenomena, SciVerse ScienceDierct journal, Dec. 28, 2012, pp. 1-6, Carbon 55 (2013) 285 290, Elsevier, Ltd., online.
Making New Solutions Possible with Advanced Ceramics, Medical Advanced Ceramics for Medical Technology, pp. 1-7, Bangerter Microtechnik AG, Europe.

(56) References Cited

OTHER PUBLICATIONS

Johann Cho et al., Carbon Nanotubes: do they toughen brittle matrices, journal, Mar. 1, 2011, pp. 1-10, J Mater Sci (2011) 46:4770 4779, Springer Science+Business Media, LLC. 2011, online.
E. Fortunati et al., Carbon Nanotubes and Silver Nanoparticles for Multifunctional Conductive Biopolymer Composites, Science Direct Journal, Feb. 26, 2011, pp. 1-10, Carbon 49 (2011) 2370 2379, Elsevier, Ltd., Online.
Maria Protopapadaki et al., Comparison of Fracture Resistance of Pressable Metal Ceramic Custom Implant Abutment with a Commercially Fabricated CAD/CAM Zirconia Implant Abutment, The Journal of Prosthetic Dentistry, Oct. 2009, pp. 1-8, vol. 110 Issue 5, Buffalo New York, Editorial Council.
A.V. Shevchoenko et al., Complex Doped Zirconia for Ceramic Implants: Production and Properties, Powder Metallurgy and Metal Ceramics, Aug. 8, 2013, pp. 441-448, vol. 53 Nos. 7-8, Springer Science+Business Media New York 2014, Ukraine.
A.V. Ragulya, Consolidation of Ceramic Nanopowders, Invited Review, May 6, 2008, pp. 118-134, Advances in Applied Ceramics 2008 vol. 107 No. 3, Ukraine.
Fei Xin et al., Decoration of Carbon Nanotubes with Silver Nanoparticles for Advanced CNT/Polymer Nanocomposites, Composites: Part A, Mar. 24, 2011, pp. 1-7, Composites: Part A 42 (2011) 961-967, Elsevier, Ltd.
P. Dahl et al., Densification and Properties of Zirconia Prepared by Three Different Sintering Techniques, Science Direct, Sep. 12, 2006, pp. 1603-1610, Ceramics International 33 (2007) 1603 1610, Elsevier, Ltd. and Techna Group S.r.l. 2006.
Ben Milsom et al., The Effect of Carbon Nanotubes on the Sintering Behaviour of Zirconia, Journal of the European Ceramic Society Jul. 28, 2012, pp. 4149-4156, vol. 32 (2012), London.
Kamal Ebeid et al., Effect of Changes in Sintering Parameters on Monolithic Translucent Zirconia, Science Direct Journal, Feb. 6, 2014, pp. e419-e424, Dental Materials 30 (2014), Elsevier, Ltd.
M. Cattani-Lorente, Effect of Different Surface Treatments on the Hydrothermal Degradation of a 3Y-TZP ceramic for Dental Implants, Journal Science Direct, Feb. 14, 2014, pp. 1136-1146, Dental Materials 30 (2014), Elsevier, Ltd., Geneva.
Amilcar C. Freitas Jr. et al., The Effect of Implant Design on Insertion Torque and Immediate Micromotion, Article, Nov. 23, 2010, pp. 113-118, Clinical Oral Implants Research 23, New York, New York.
Zuhair A. Munir et al., Electric Current Activation of Sintering: A Review of the Pulsed Electric Current Sintering Process, Journal, Sep. 21, 2010, pp. 1-19, J. Am. Ceram. Soc. 94[1] 1 19, The American Ceramic Society, Davis California.
Gustavo Suarez, Effect of Starting Powders on the Sintering og Nanostructed ZrO2 Ceramics by Colloidal Processing, Science and Technology of Advanced Materials, Apr. 16, 2009, pp. 1-8, Sci. Technol. Adv. Mater. 10 (2009) 025004 (8pp), National Institute for Materials Science, United Kingdom.
G.W. Liu et al., Fabrication of Coloured Zirconia Ceramics by Infiltating Water Debound Injection Moulded Green Body, Short Communication, Apr. 22, 2009, pp. 57-62, vol. 110 No. 1, Maney on behalf of the Institute of Materials, Minerals and Mining, Beijing.
Haibin Zhang et al., Fabrication of Transparent Yttria by High-Pressure Spark Plasma Sintering, Journal; Rapid Communications of the American Ceramic Society, Jun. 7, 2011, pp. 3206-3210, vol. 94 No. 10, Advanced Materials Processing Unit, Japan.
M. Gahlert et al., Failure Analysis of Fractured Dental Zirconia Implants, Article Clinical Oral Implants , Mar. 19, 2011, pp. 287-293, vol. 23, Joh Wiley & Sons, Germany.
Reham B. Osman et al., Fractured Zirconia Implants and Related Implants Designs: Scanning Electron Microscopy Analysis, Clinical Oral Implants, pp. 592-597, vol. 24, John Wiley & Sons, Online.
P. Vult Von Steyern, Fracture Strength of Two Oxide Ceramic Crown Systems After Cyclic Pre-Loading and Thermocycling, Journal of Oral Rehabilitation, Oct. 25, 2005, pp. 682-689, vol. 33, Blackwell Publishing, Ltd., Sweden.
Alexander Filippov et al., Frictional-Anisotropy-Based Systems in Biology: Structual Diversity and Numerical Model, Scientific Reports, Feb. 7, 2013, pp. 1-6, vol. 3:1240.
M.T. Laranjo et al., Gold Nanoparticles Enclosed in Silica Xerogels by High-Pressure Processing, Jul. 7, 2011, pp. 4987-4995, J Nanopart Res (2011) 13, Springer Science+Business Media B.V., Online.
Wei Cui, Improving Thermal Conductivity While Retaining High Electrical Resistivity of Epoxy Composites by incorporating Silica-Coated Multi-walled Carbon Nanotubes, Journal Science Direct, Sep. 29, 2010, pp. 495-500, Carbon 49 (2011), Elsevier Ltd., Online.
K. Madhav Reddy, Inhibition of Grain Growth During the Final Stage of Multi-Stage Sprak Plasma Sintering if Oxide Ceramics, Scripta Materialia, Jun. 4, 2010, pp. 585-588, vol. 63, Elsevier Ltd., Online.
Wael Att et al., Influance of Preparation and Wall Thickness on the Resistance to Fracture of Zirconia Implant Abutments, pp. e196-e203, 2011 Wiley Periodicals, Inc. Germany.
S. Anil et al., Dental Implant Surface Enhancement and Osseointegration, Implant Dentistry—Rapidly Evolving Practice, pp. 83-108, www.intechopen.com.
I. Ahmad et al.,Interfacial Investigations and Mechanical Properties of Carbon Nanotube Reinforcing Al2O3 Nanocomposites, Divisions of Materials, Mechanics & Structures, pp. 1-10, Nottingham NanoScience, University Park, Nottingham.
Isreal Krindges et al., Low-Pressure Injection Molding of Ceramic Springs, International Journal of Applied Ceramic Technology, 2008, pp. 243-248, vol. 5 No. 3, The American Ceramic Society, Brazil.
Clarisse Sanon et al., Low Temperature Degradation and Reliability of One-Piece Ceramic Oral Implants with a Porous Surface, SciVerse Science Direct Journal Jan. 21, 2013, pp. 389-397, Dental Materials 29 (2013), Elsevier Ltd. Online.
V. Piotter, Manufacturing of Complex-Shaped Ceramic Components by Micropowder Injection Molding, International Journal of Advanced Manufacturing Technology, May 30, 2009, pp. 131-134, vol. 46, Springer Verlag London Limited 2009.
A. Schubert, Micro-EDM Milling of Electrically Nonconducting Zirconia Ceramics, Journal SciVerse ScienceDirect, Mar. 26, 2013, pp. 298-302, vol. 6, Elsevier B.V.
Maria A. Auger, Molding and Replication of Ceramic Surfaces with Nanoscale Resolution, www.small-joumal.com, Sep. 14, 2004, pp. 300-309, vol. 1 No. 3, Wiley VCH.
Nitin P. Padture, Multifunctional Composite of Ceramics and Single-Walled Carbon Nanotubes, Advanced Materials, Feb. 23, 2009, pp. 1767-1770, vol. 21, Wiley VCH, Columbus Ohio.
Mehdi Mazaheri, Multi-Walled Carbon Nanotubes/ Nanostructed Zirconia Composites: Outstanding Mechanical Properties in a Wide Range of Temperature, Journal of Composites Science and Technology, Feb. 1, 2011, pp. 939-945, vol. 71, Elsevier Ltd.
I. Ahmad et al., Multi-Walled Carbon Nanotubes Reinforced Al2O3 Nanocomposites: Mechanical Properties and Interfacial Investigations, Journal of Composites Science and Technology, Mar. 18, 2010, pp. 1199-1206, vol. 70, Elsevier Ltd. Online.
Haibin Zhang, Optical Properties and Microstructure of Nanocrystalline Cubic Zirconia Prepared by High-Pressure Spark Plasma Sintering, Journal of American Ceramic Society, Jan. 29, 2011, pp. 2981-2986, vol. 94 No. 9.
Feng-Jun Zhang, Photoelectrocatalytic Properties and Bactericidal Activities of Silver-Treated Carbon Nanotube/Titania Composites, Journal of Composites Science and Technology, Jan. 14, 2011, pp. 658-665, vol. 71, Elsevier Ltd.
S.S Scherrer, POST—Hot Isostatic Pressing: A healing Treatment for Process related defects and Laboratory Grinding Damages of Dental Zirconia, Journal of SciVerse Science Direct, Apr. 25, 2013, pp. e180-e190, vol. 29, Elsevier Ltd.
Tatsuo Kumagai, Rapid Densification of Yttria-Stabilized Tetragonal Zirconia by Electric Current-Activated/Assited Sintering Technique, Jun. 17, 2010, pp. 1215-1223, vol. 94 No. 4, The American Ceramic Society.
David Salamon, Rapid Sintering of Crack-free Zirconia Ceramics by Pressure-Less Spark Plasma Sintering, Feb. 14, 2012, Scripta Materialia, pp. 899-902, vol. 66, Elsevier Ltd. Sweden.

(56) References Cited

OTHER PUBLICATIONS

Shih-Fu Ou, Research of Antibacterial Activity on Silver Containing Yttria-Stabilized-Zirconia Bioceramic, Oct. 17, 2012, pp. 3591-3596, Ceramics International, vol. 39, Elsevier Ltd and Techna Group S.r.l.

R. Chaim, Sintering and Densification of Nanocrystalline Ceramic Oxide Powders: a review, Advances in Applied Ceramics, Mar. 5, 2008, pp. 159-169, vol. 107 No. 3, Institute of Materials, Minerals and Mining.

Zeynep Ozkurt et al, Zirconia Dental Implants: A Literature Review, Journal of Oral Implantology, 2011, pp. 367-376, vol. XXXVII No. 3, Department of Prosthodontics, Faculty or Dentistry.

Farhana Mohd Foudzi et al., Yttria Stabilized Zirconia Formed by Micro Ceramic Injection Molding: Rheological Properties and Debinding Effects on the Sintered Parts, SciVerse Science Direct Article, Sep. 10, 2012, pp. 1-10, Elsevier Ltd. amd Techna Group S.r.l.

Dr. Richard M. Parker, Use of Zirconia in Restorative Dentistry, Dentistry Today, Mar. 2007, pp. 114-119.

S.F. Wang et al., Transparent Ceramics: Processing, Materials and Applications, Progress in Solid State Chemistry, Dec. 2, 2012, pp. 20-54, vol. 41 (2013), Elsevier Ltd.

R.H.W. Brodbelt et al., Translucency of Dental Porcelains, Dec. 4, 1978, pp. 70-75 Jan. 1980, J Dent Res vol. 59 No. 1, University of Michigan.

Jin Gyu Park et al., Thermal Conductivity of MWCT/epoxy Composites: The Effects of Length, Alignment and Functionalization, SciVerse Science Direct Journal, Jan. 4, 2012, pp. 2083-2090, Carbon 50, Elsevier Ltd., Online.

H.K. Kansal et al., Technology and Research Developments in Powder Mixed Electric Discharge Machining, Journal or Materials Processing Technology, Oct. 31, 2006, pp. 33-41, vol. 184 (2007), Elsevier B.V.

Wei Liu et al., Surface Modifcation of Stearic Acid to Zirconia Powders Induced by Ball Milling for Water-Based Injection Molding, Journal of the American Ceramic Society, Jan. 28, 2011, pp. 1327-1330, vol. 95 No. 5, The American Ceramics Society.

\* cited by examiner

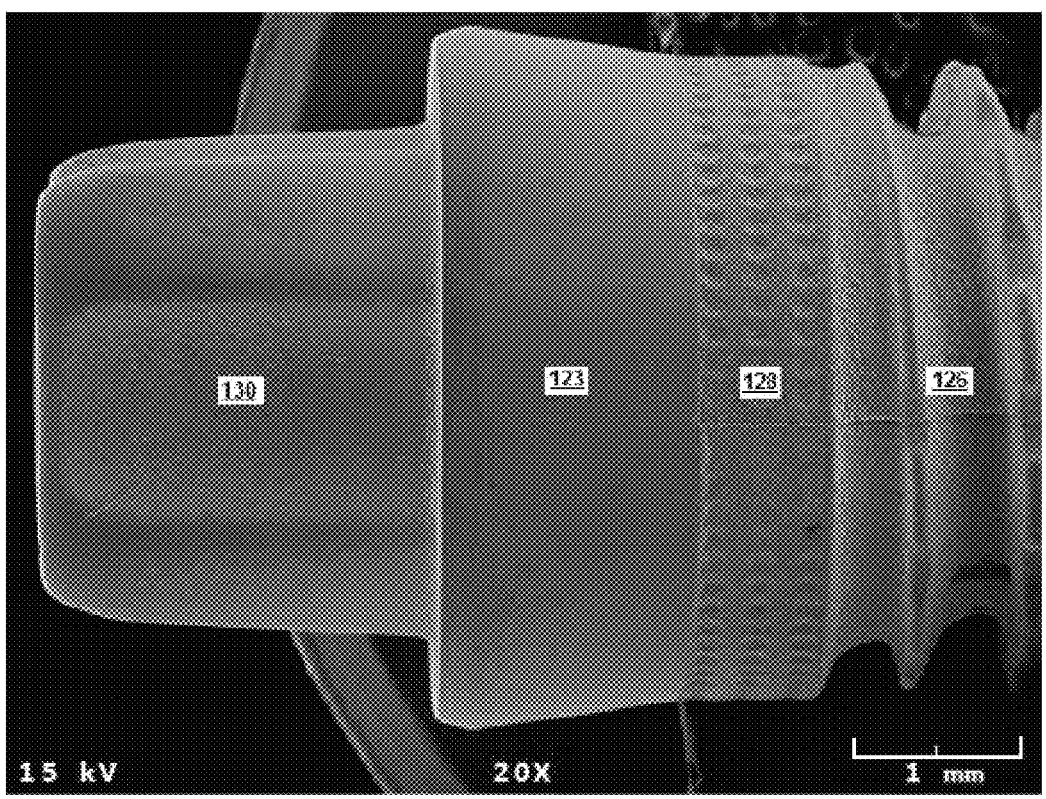
FIG. 5A
FIG. 5B
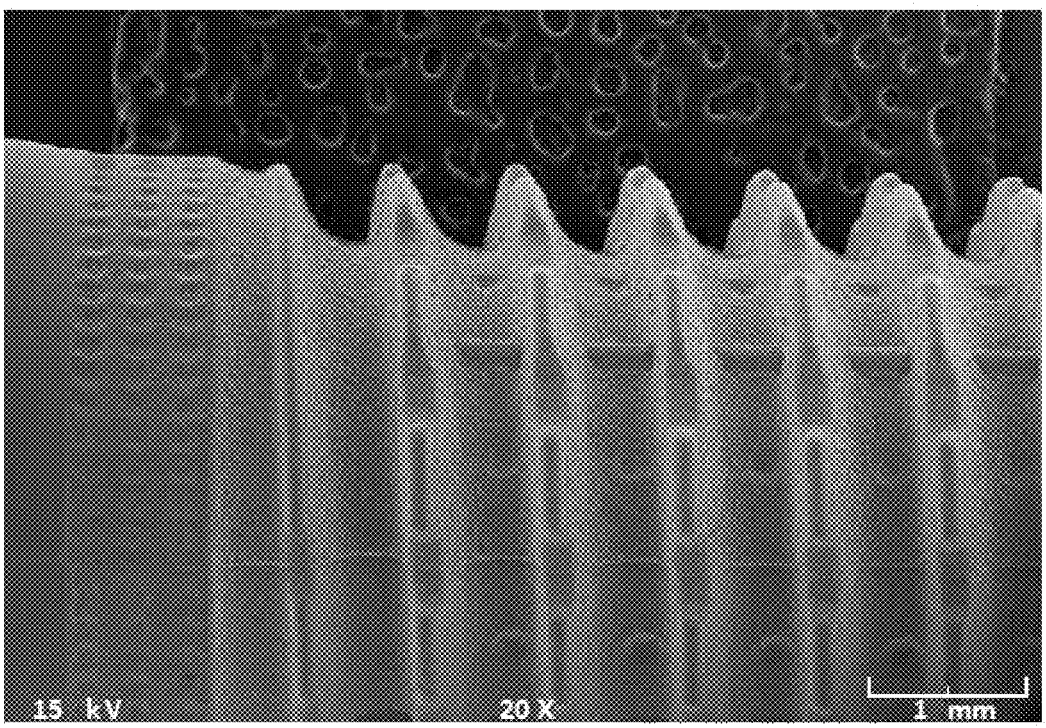

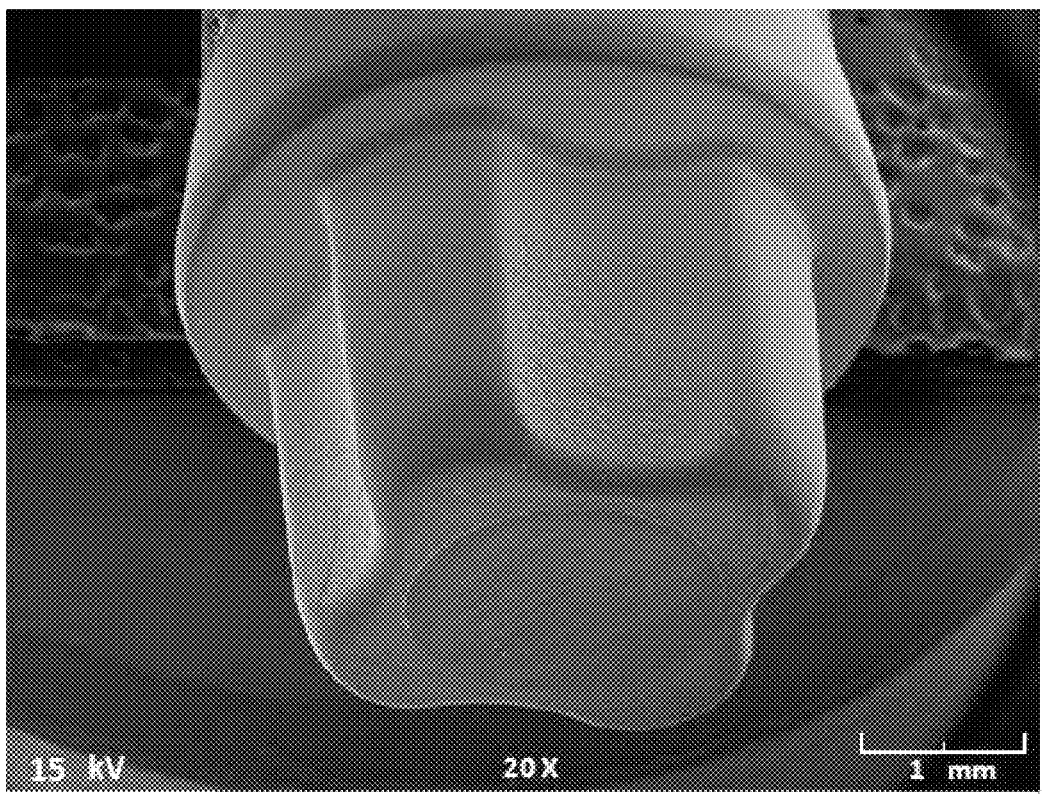
FIG. 5C
FIG. 5D
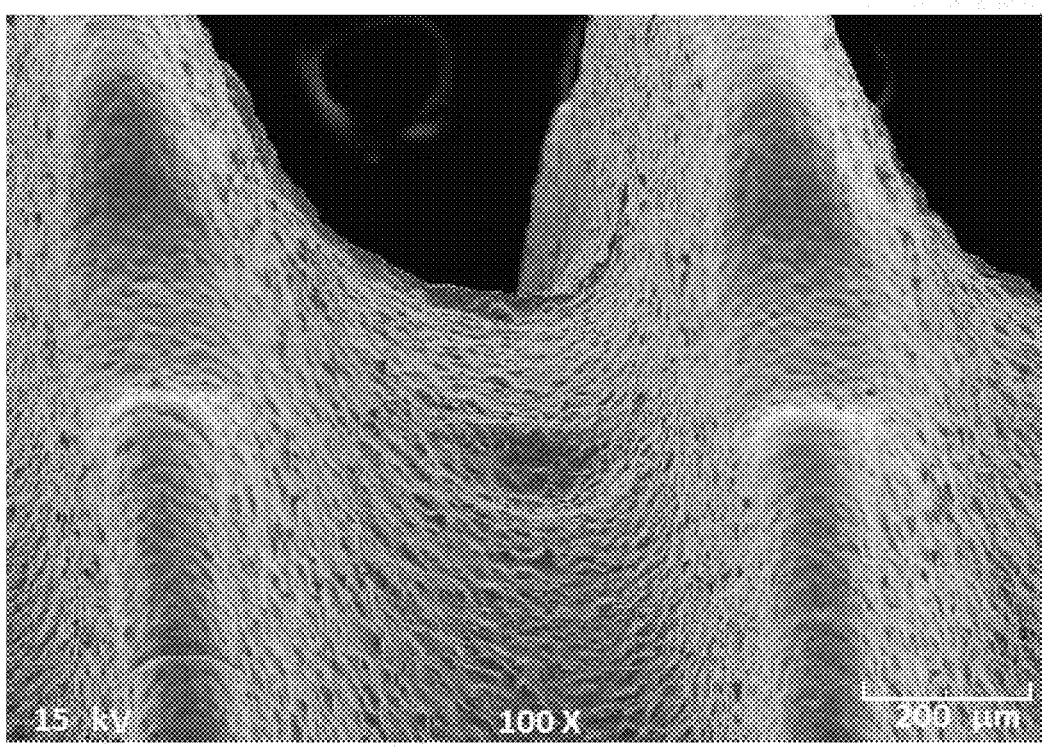

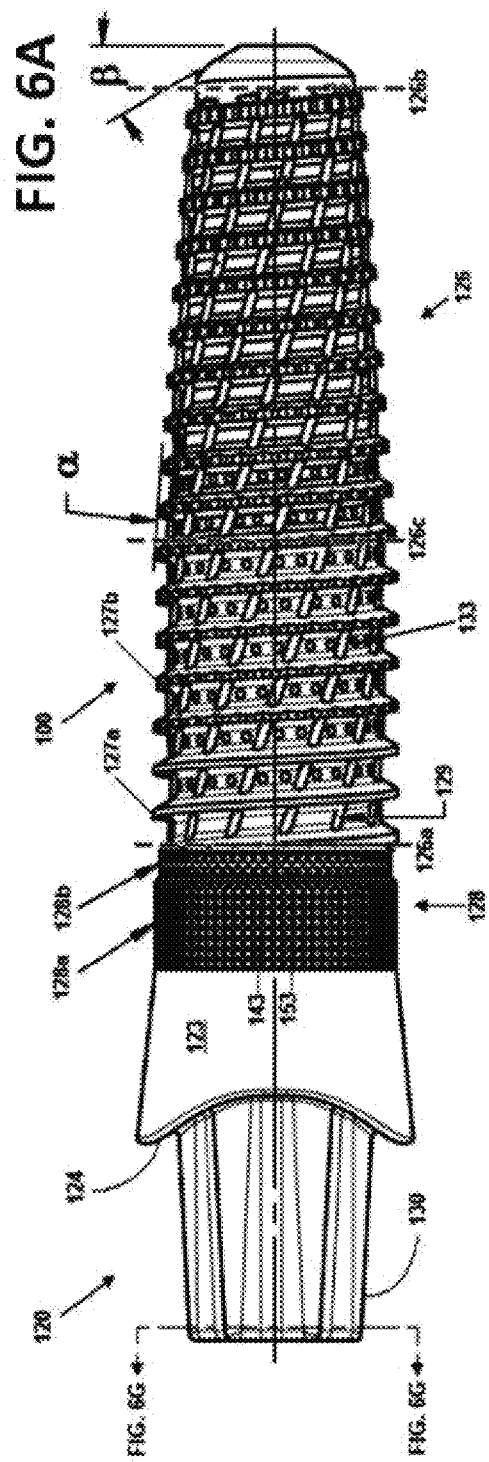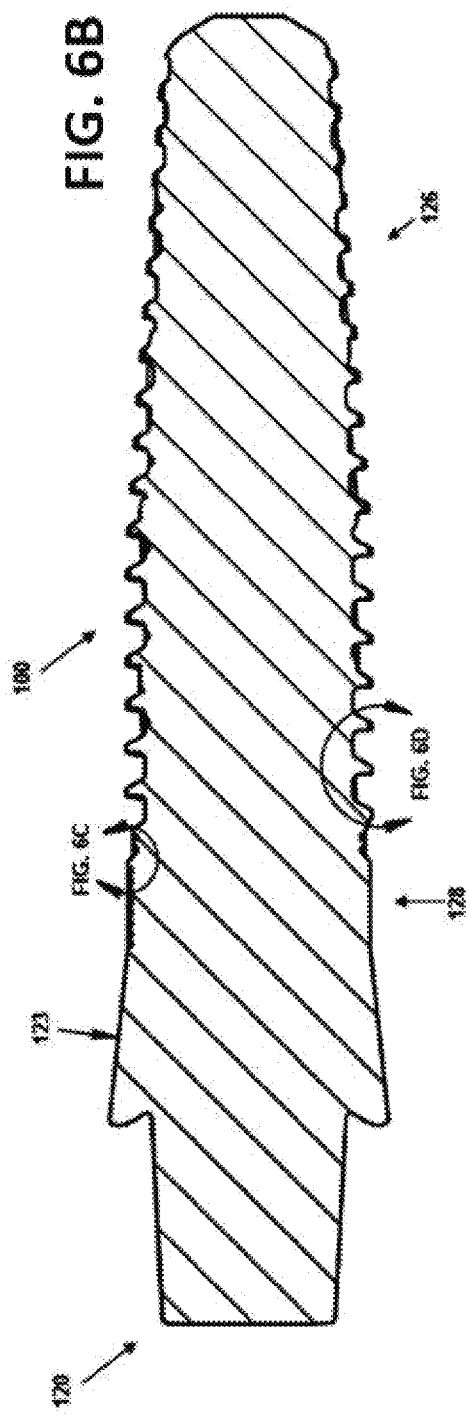

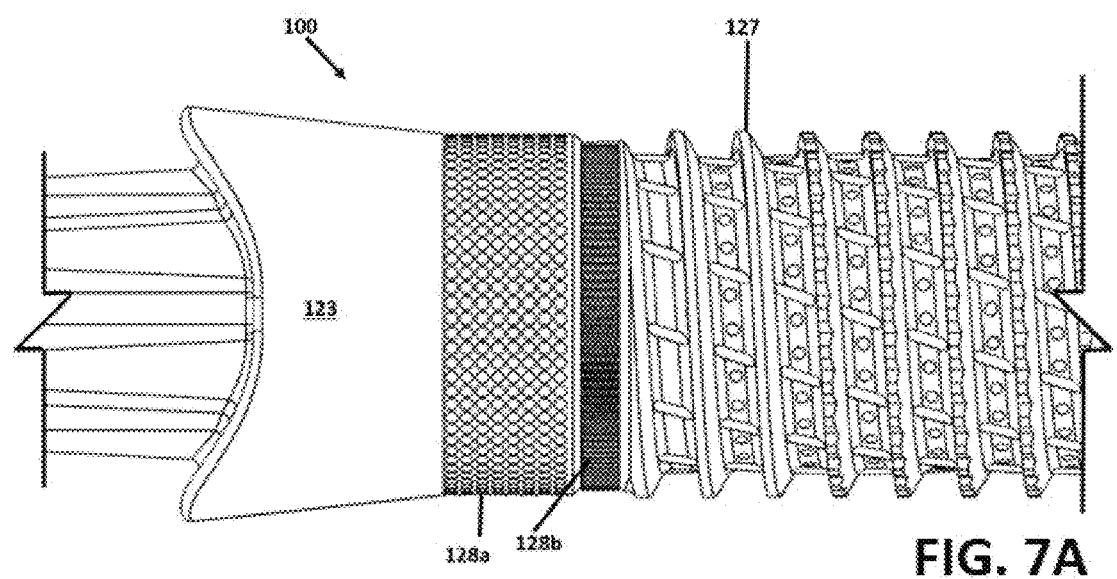
FIG. 7A
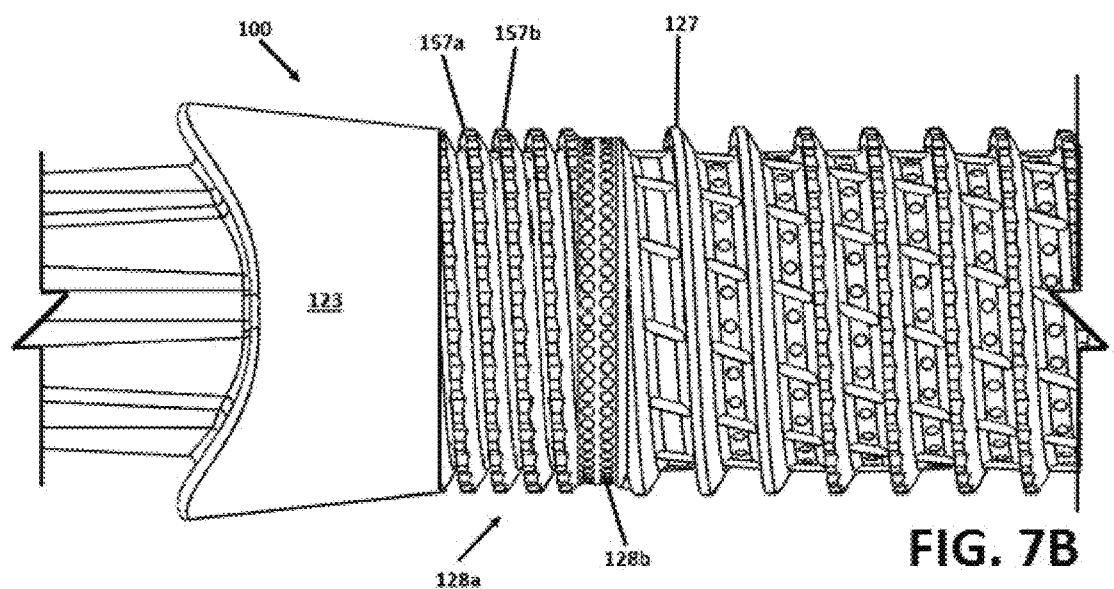
FIG. 7B
FIG. 8A
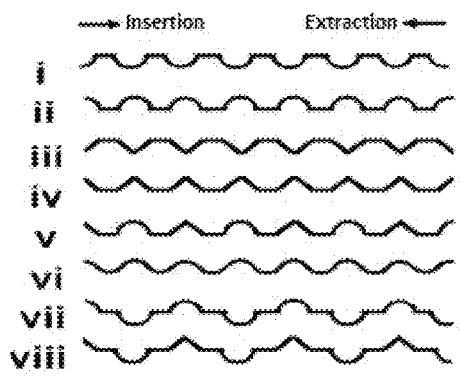
FIG. 8B
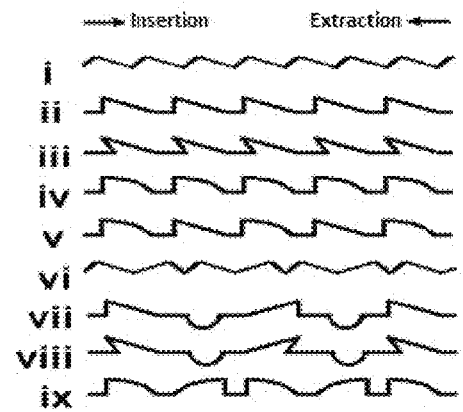

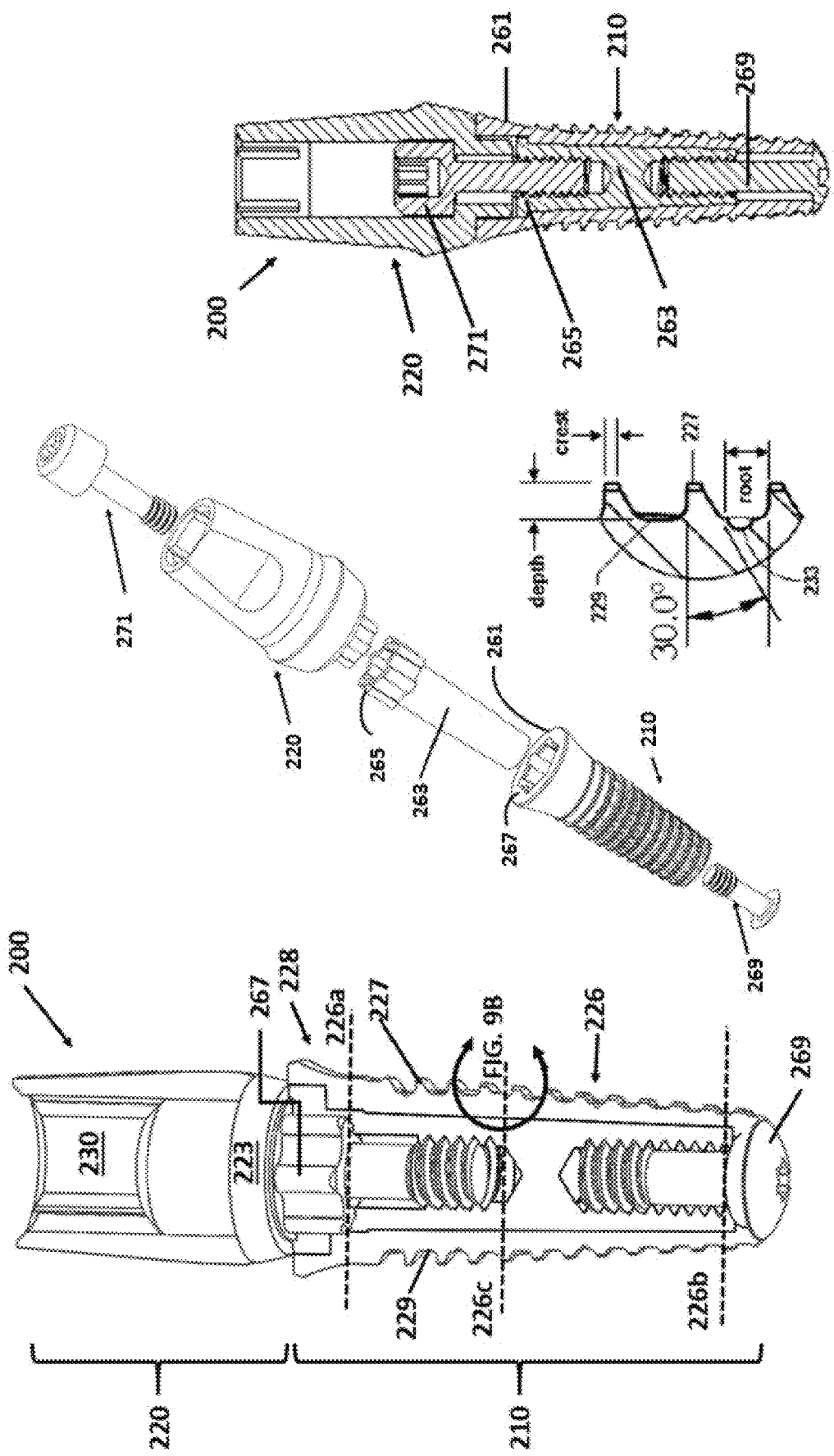

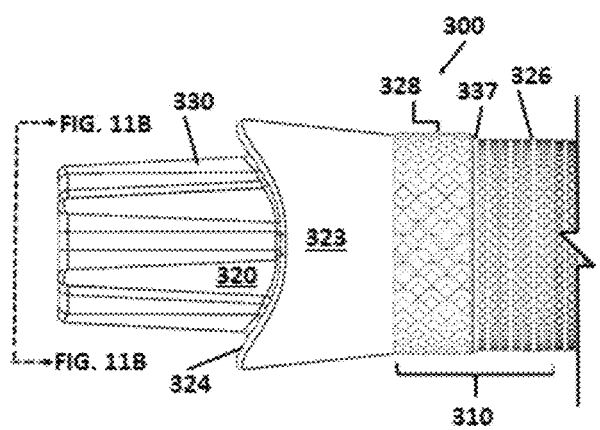
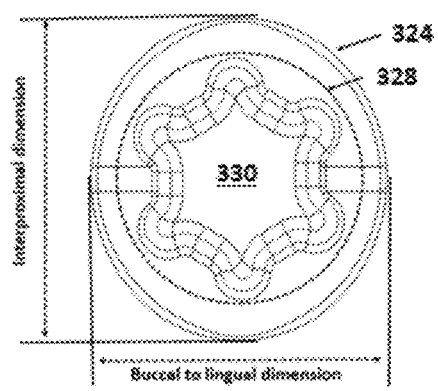
FIG. 11A  FIG. 11B
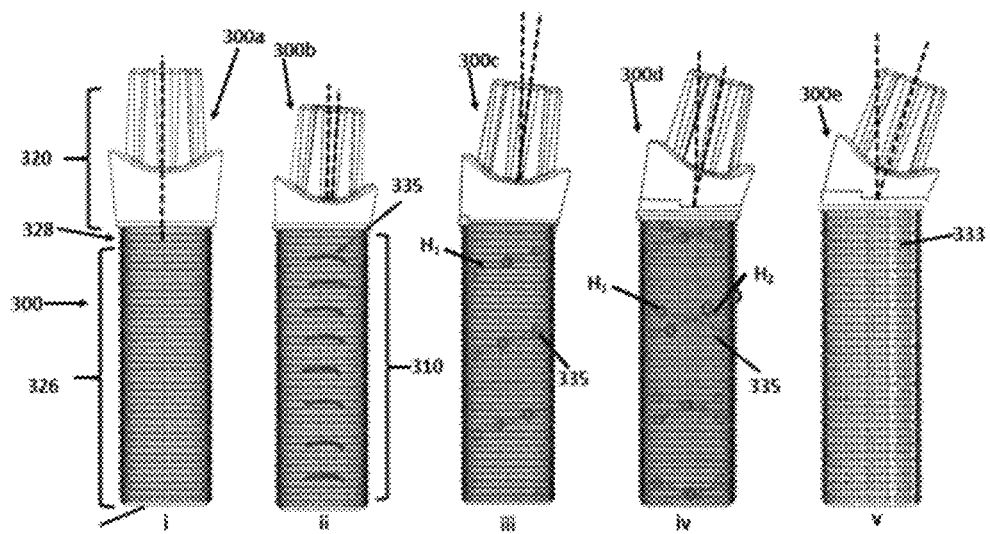
FIG. 11C
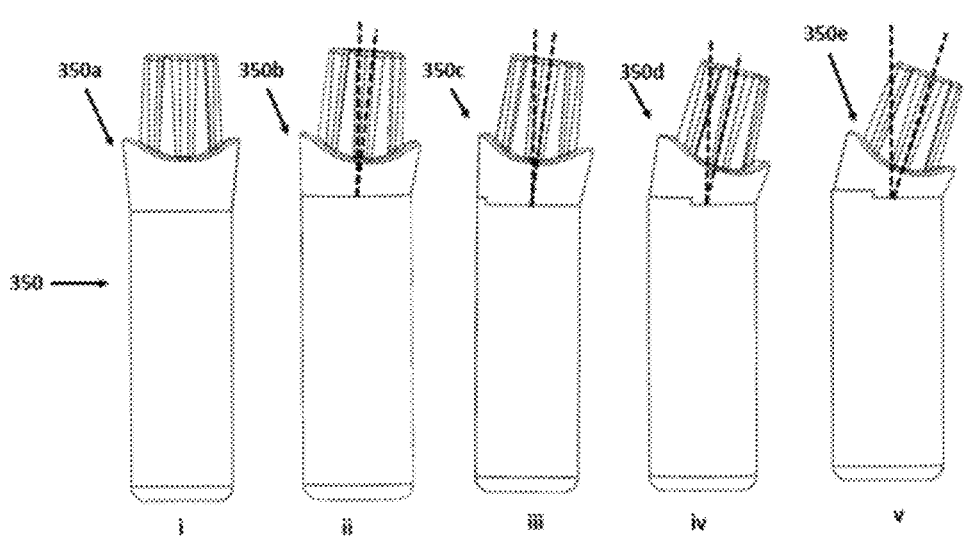
FIG. 11D

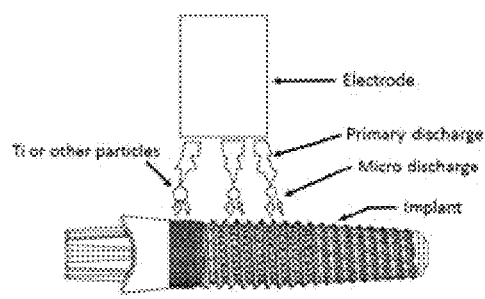
FIG. 19
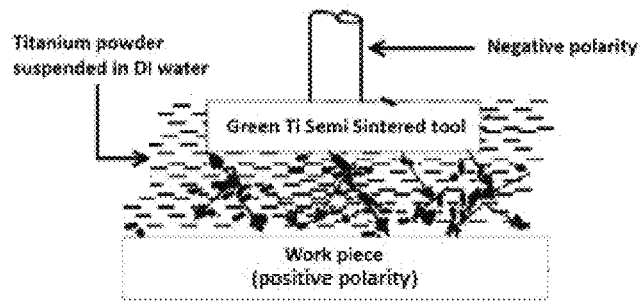
FIG. 20
FIG. 21
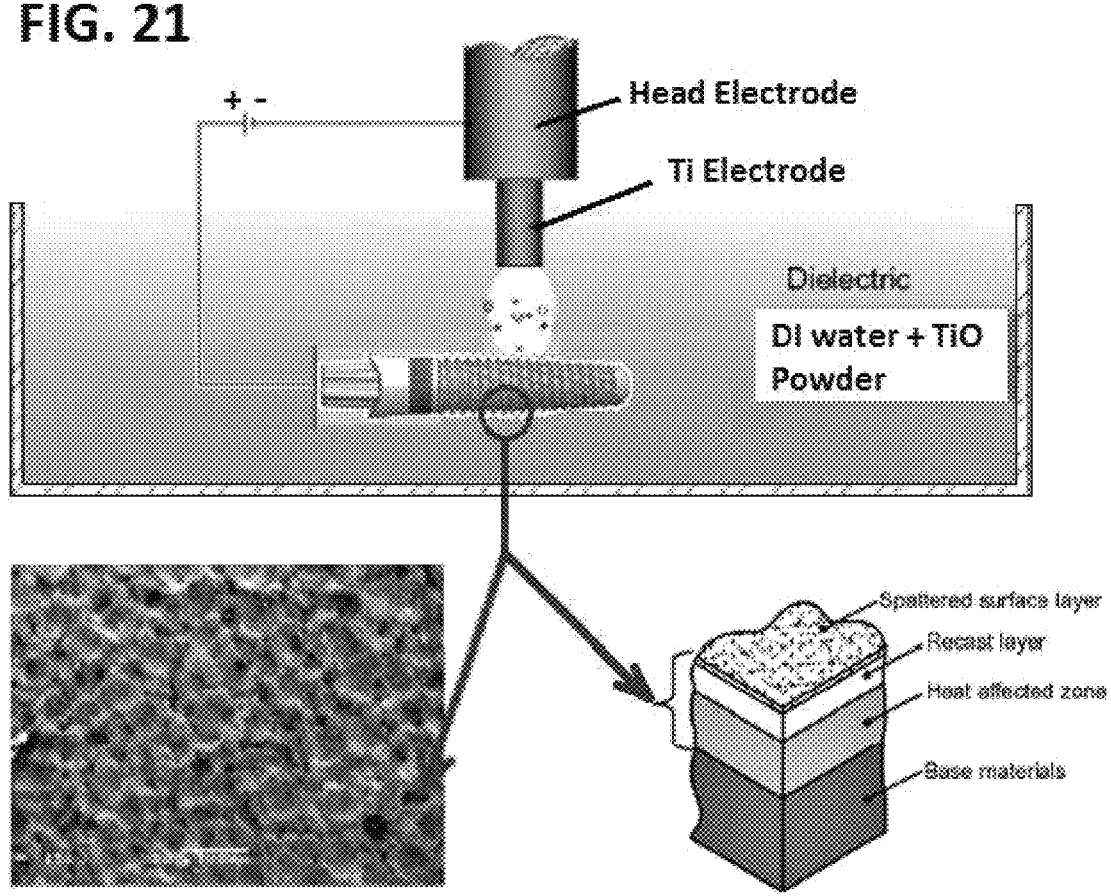

OSSEOINTEGRATIVE SURGICAL IMPLANT

CROSS-REFERENCE TO RELATED APPLICATIONS

The application claims the benefit under 35 U.S.C. § 119(e) to Provisional Patent Application No. 61/986,242 filed Apr. 30, 2014, the entire contents of which are incorporated herein by reference.

STATEMENT RE: FEDERALLY SPONSORED RESEARCH/DEVELOPMENT

Not Applicable

BACKGROUND

The present invention generally relates to osseointegrative implants and related tools and components for surgical bone fixation and dental restoration purposes and improved methods for manufacturing and using the same.

Surgical bone fixation devices such as screws, staples, rods, and plates have been in clinical use for decades. These devices largely evolved from industrial designs for fastening wood, steel, plastic and other materials. Starting in the 1950s Per-Ingvar Branemark and others demonstrated that implanted bone fixation devices made of pure titanium had the ability to become permanently incorporated with living bone tissue. That is, the living bone tissue becomes so fused with the titanium oxide layer of the implant that the two cannot be separated without fracture. See, e.g., Branemark, P L., Osseointegration and its Experimental Studies, J Prosthetic Dentistry 1983 50:399-410. Bone fixation devices formed from pure titanium and its various alloys are the basis for modern skeletal fixation techniques that support healing and functional repair of the human body. These and similar devices also form the basic foundation of the rapidly evolving field of restorative implant dentistry.

Restorative implant dentistry generally involves the surgical restoration of one or more teeth in a patient's mouth using various bio-compatible prosthetic components. Such bio-compatible prosthetic components typically include an osseointegrative dental implant or anchor that supports a prosthetic tooth (e.g., a porcelain crown), an implant-supported bridge or an implant-supported denture. Dental implants have traditionally been fabricated as a bone-anchoring pin or screw formed from a known osseointegrative material, such as pure titanium or a titanium alloy. The bone-anchoring portion of the pin or screw is typically configured to extend into an osteotomy formed within the alveolar bone (either the maxilla or the mandible) of a patient. Biological healing and bone tissue growth around the surgical site eventually results in osseointegration (i.e., permanent fixation) of the implant body with the living bone tissue surrounding the osteotomy and the implant body. Other portions of the implant body typically extend through the gingiva into the oral cavity to support one or more prosthetic teeth.

Depending on the clinical diagnosis and the particular needs and desires of the patient an oral surgeon will typically use either a single-stage (typically one-piece) implant and restoration procedure or a two-stage (multi-piece) implant and restoration procedure. In a single-stage restoration procedure the implant body is typically formed as a single integral structure having both subgingival and supragingival portions. The subgingival portion is firmly implanted into the bone while the supragingival portion extends transgingivally into the oral cavity to provide support for a temporary or permanent prosthetic tooth. One drawback of conventional single-stage implants is that there is limited flexibility in the placement of the implant because the supragingival portion is fixed relative to the subgingival portion and extends into the oral cavity typically in fixed coaxial alignment with the implanted subgingival portion. In certain clinical situations the size, shape and orientation of the native or grafted bone at the osteotomy site can limit or preclude the use of a conventional single-stage implant.

In a two-stage restoration, the implant body is typically formed from two or more pieces comprising normally an "anchor" portion and an "abutment" portion. Typically, the anchor portion of the implant body includes a bone-engaging subgingival portion that is implanted into the bone in a first surgical procedure. In some cases the surrounding gingiva is sutured closed over the entire anchor portion of the implant body while healing and initial osseointegration occurs. In other cases, some portions of the anchor portion may remain exposed through the gingiva. For example, the anchor portion may include a transgingival portion and/or a supragingival portion. In yet other cases, a temporary transgingival healing abutment or similar structure may be used to promote transgingival healing and desired soft tissue growth around the exposed portions of the implant. Once initial healing is complete and the implant is determined to be sufficiently stable a hole is formed through the gingiva (or the healing abutment is removed) in a second surgical procedure and a permanent abutment and/or other supragingival structure is secured to the implant and extends transgingivally into the oral cavity to provide support for a temporary or permanent prosthetic tooth. A primary advantage of two-stage implants is greater flexibility in the placement of the implant body because the size, shape and angular orientation of the supragingival portion can often be changed once the implant anchor has been surgically placed. One disadvantage of two-piece implants is that the retaining screw or other mechanical fastening device used to secure the abutment to the anchor can eventually loosen or break. Furthermore the junction where the abutment seats against the anchor can form a micro gap, which can act as a bacterial trap and lead to infection.

The anchor portion of conventional dental implants have taken on two basic forms, either a smooth cylindrical form which is press-fit into a drilled osteotomy, or a threaded form which is threaded into a threaded or unthreaded osteotomy prepared using a bone drill, a bone tap and/or other specialized tools. The geometry of a threaded implant is typically such that it can be inserted into the osteotomy and firmly secured to the surrounding bone tissue via one or more threads which advance into the osteotomy and create residual stresses in the surrounding bone tissue which hold the implant securely in place. This provides good primary stability, which is a desirable feature of most threaded implants. However, too much residual stress can cause bone necrosis and/or recession over time, leading to reduced secondary stability (i.e., reduced osseointegration of the implant and/or long-term loss of securement). Press-fit implants are generally easier to install and have more predictable secondary stability due to more uniform distribution of residual stresses. However, primary stability is typically less with conventional press-fit implants because there is typically little or no positive mechanical engagement and interlocking of the implant body with the surrounding bone tissue.

Many variations and combinations of these two basic forms have been devised over the years. For example, US20040101807 describes a threaded titanium implant configured to be screwed into the bone of a patient. US05762499 describes an implant having a press fit geometry in which the implant body is tapered and has a plurality of circumferential grooves for receiving bone ingrowth. US05269686 describes a combination drivable threaded titanium implant having a long-pitch rounded thread which provides frictional retention as the implant is driven into an unthreaded osteotomy with a mallet or the like. US06273722 similarly describes a hybrid press-fit threaded titanium implant having a body configured to be press-fit into an unthreaded osteotomy and having a shallow clockwise helical thread for securely locking the implant in position and a counter-clockwise helical groove for improving osseointegration and long-term stability of the implant. US20110269103 describes an expandable press-fit implant comprising an expandable portion configured to move between an unexpanded (non-stress-inducing) configuration and an expanded (stress-inducing) configuration for providing both primary and secondary implant stability.

Once sufficient implant stability has been achieved other prosthetic components can be secured to and/or built on top of the implant body, such as an anatomically-functional aesthetic porcelain crown or cap. Typically a support post or abutment is formed or mounted on the implant body and protrudes into the oral cavity through an opening provided in the soft gingivae or gum tissues covering the alveolar bone. The support post or abutment is typically shaped, angled and/or contoured to form a medically and structurally sound transdermal interface between the implanted bone-anchoring device and a functionally and aesthetically sculpted dental prosthesis or other restorative device desired to be supported. Typically, the coronal portion of the post or abutment that extends transdermally through the soft gum tissue has a machined or polished biologically inert surface that provides a good sealing interface with the surrounding soft gum tissues. The smooth surface prevents or resists the accumulation of plaque and calculus and facilitates ease of cleaning. The remaining portions of the post or abutment extend outward so as to receive and support a dental prosthesis or other restorative device that is typically bonded or cemented directly to the abutment using a suitable bonding agent such as zinc phosphate or polycarboxylate.

In a typical single-tooth restoration an anatomically-functional prosthetic tooth is fabricated from dental-grade porcelain, which is a special type of ceramic material made by firing clay, in the form of kaolin, to high temperatures between 1,200° C. (2,192° F.) and 1,400° C. (2,552° F.). Typical properties associated with porcelain include low solubility; considerable strength, hardness, toughness, whiteness, translucency, and a high resistance to chemical attack and thermal shock. The toughness, strength, and translucence of porcelain arise mainly from the high-temperature formation of glass and the mineral mullite or porcelainite (aluminum silicate, $Al6Si2O13$, in orthorhombic crystalline form) within the fired body. The combination of these unique properties provide for a functional and aesthetically pleasing lifelike analogue of a natural tooth being replaced. See, e.g., R. Brodbelt et al., Translucency of dental porcelains, J Dent Res 59(1):70-5 (1980), incorporated herein by reference in its entirety.

A typical drawback encountered when using a titanium post or abutment to support a porcelain crown is that it generally results in a dark, central rod-like shadow in the restored tooth, particularly when exposed to high-brightness light. This makes the prosthesis somewhat unattractive and able to be distinguished from a natural tooth, especially when the restoration is located in the upper anterior region of the mouth. Further, since the materials are different at the bonding interface (porcelain versus titanium) and have different mechanical properties, surface chemistries and coefficients of thermal expansion, problems are frequently encountered when bonding or securing the prosthesis to the supporting abutment. Clinical studies have also shown that titanium can cause adverse biological reactions when maintained in direct contact with the soft gingivae surrounding the implant site, leading to a higher-than-desired incidence of gum recession around the implant site and further compromising the desired aesthetics of the restoration.

One attempted solution to the attractiveness, securing and recession problem has involved the use of a two-stage implant having an abutment fabricated partially or entirely from a ceramic material, typically, alumina (aluminum oxide, $Al2O3$), which is white in color and can be tinted to closely match the color of a natural tooth being replaced. This approach allows direct surface bonding by interaction of a porcelain crown to a ceramic support post resulting in a secure and almost seamless bond between the prosthetic structure and the ceramic support post. Long-term clinical studies have demonstrated that ceramic materials are generally more tissue-friendly than titanium when in prolonged direct contact with the soft gingivae surrounding the implant site, leading to less incidence of gum recession. Many efforts have thus been made to provide dental implants in which at least the parts that extend through the gingivae into the oral cavity are made partially or entirely from a ceramic material.

For example, US20130236855 discloses a ceramic dental implant abutment for securing a prosthetic tooth to an implant body via a titanium screw that extends through a passageway formed in the abutment. US07708559 discloses a dental implant system wherein a ceramic abutment is provided having a screw-receiving central bore and a lower mating surface configured to mate with an upper mating surface of the dental implant body. US06168435 discloses a ceramic abutment having a supragingival portion protruding beyond the gingivae, a subgingival portion extending into the gingivae and a metallic core for providing structural support and securement of the abutment to the implant body. DE19530981 discloses a prefabricated implant abutment comprising a tooth-colored zirconia ceramic configured to be attached to a titanium implant.

Conventional ceramic abutments, while providing a viable alternative to titanium abutments and a solution to some of the aforenoted problems, do not completely resolve the aesthetic concerns and can also introduce a number of additional problems and challenges. Aesthetic limitations result primarily from the relative opacity of the ceramic material when compared to a natural tooth and also the need for a metal (e.g., titanium) retention screw to secure the ceramic abutment to the implant. Other problems and challenges stem from the fact that ceramic materials have a much greater hardness and much more limited flexure than titanium. When a ceramic abutment is secured to a titanium implant, inevitable rocking of the abutment (due to, for example, chewing action) causes high-stress interactions between the relatively hard ceramic abutment and the relatively soft metal implant. This can eventually damage the implant severely enough that surgical intervention is required to remove and replace the titanium implant.

Some all-ceramic implant solutions have also been proposed that provide both a subgingival anchoring portion and a transgingival abutment portion fabricated from a ceramic material as either a single stage (one-piece) or two stage (multi-piece) implant system. Conventional all-ceramic implants are found in a variety of geometries and configurations typical of those used in traditional titanium implant designs. For example, US20110045439 discloses a one-piece threaded zirconia dental implant having integrally-formed subgingival and supragingival portions and a bonded transmucosal abutment component formed of either ceramic or a high-strength polymer material. US20110076643 discloses a two-part threaded implant formed from a ceramic composition comprising zirconium oxide, yttrium oxide, hafnium oxide and aluminum oxide.

Some commercially-available all-ceramic implant solutions eliminate the aforenoted titanium-to-ceramic interface problems and, thus, provide a viable alternative to traditional titanium or titanium-ceramic implants. However, the use of conventional ceramic materials and fabrication techniques have limited the number of applications due to high production costs, poor mechanical strength, low fatigue stability and tendency to crack or fracture over time. Conventional ceramic implants have also historically been considered clinically less satisfactory than metal implants, such as titanium or titanium alloys, because of reduced primary stability resulting from inherent material limitations which limit the amount of torque or insertion force that can be applied to the implant body (for threaded implants), and reduced or retarded secondary stability resulting from slower and/or less complete osseointegration.

A variety of high-performance ceramic materials formed from zirconium-dioxide (zirconia, ZrO2) have recently been introduced and have been used successfully in a number of different medical and dental applications. Zirconia is well known as an orthopedic implant material and has been used in hip surgery for many years. By adding a small amount of yttrium (Y2O3) to zirconia, it is possible to fully or partially stabilize the ceramic in a tetragonal phase that normally is unstable at room temperature. Several studies have reported fracture toughness values of 9 MPa•m½ for yttrium-stabilized zirconia, substantially higher than for other ceramics such as alumina (~3-5 MPa•m½), albeit still significantly lower than titanium (~44-66 MPa•m½). Yttria-stabilized zirconia also exhibits good wear resistance and has a light white color which can be tinted to closely match a natural tooth color. Ceramic materials formed from zirconium-dioxide are also typically radiopaque which desirably allows the material to be easily viewed through conventional dental x-ray imaging.

For example, US06165925 discloses a composition of yttrium-stabilized zirconium oxide (zirconia) useful for the production of a densely sintered semi-finished article as a starting material for the manufacture of a prosthesis. WO0134056 discloses a single-piece dental implant formed from zirconia ceramic consisting of an insertion portion which can be fitted in the jawbone and a support component which protrudes beyond the jawbone. However, to achieve sufficient material strength and toughness, the zirconia ceramic is typically densely sintered prior to machining. This makes the resulting sintered body extremely hard and difficult to machine and results in a finished surface having essentially no porosity. A dental implant made of densely-sintered zirconia ceramic is typically bio-inert and, thus, has only weak osseointegrative properties.

Various solutions have been proposed to improve the osseointegrative properties of a densely sintered zirconia ceramic implant while maintaining its desirable mechanical properties. For example, US20050106534 discloses a one-piece zirconia ceramic implant comprising an anchoring portion for anchoring within the bone and an abutment portion for receiving a prosthetic tooth and wherein the outer surface of at least the anchoring portion is acid etched, sandblasted or coated with a material that promotes osseointegration. EP0870478 discloses a single-piece all-ceramic dental implant having a hardened core of zirconium oxide coated with a second ceramic material which can be more-easily chemically and/or mechanically processed to provide a surface that better promotes osseointegration. US04983182 discloses a ceramic implant comprising a densely sintered body of zirconia and a coating layer of a less densely sintered mixture comprising α-tricalcium phosphate and zirconia, or hydroxyapatite and zirconia. Each of these proposed solutions involve multiple additional processing steps and materials which greatly increase the cost and complexity of manufacturing a finished product.

Despite various improvements over the years, conventional titanium implant designs and attachment components do not fully address the clinical needs for surgical replacement of natural teeth, particularly in clinical applications involving aesthetic regions of the mouth. Compared with traditional titanium implants, currently-available ceramic implants are costlier to produce, are more limited in their clinical application, are more susceptible to failure via fracture and/or fatigue, and provide less primary and secondary stability. Currently-available ceramic implants and attachment components also do not completely resolve the aforenoted aesthetic concerns due to the relative opacity of the ceramic materials used relative to the translucence of a natural tooth. Accordingly, there is a need for an improved osseointegrative implant that is cheaper to produce, provides a greater range of clinical application, greater resistance to failure via fracture and/or fatigue, good primary and secondary stability, improved ease of use, improved osseointegration, and an aesthetic translucent appearance more closely resembling that of a natural tooth being replaced.

BRIEF SUMMARY

Embodiments of the present invention provide an osseointegrative implant and related tools, components and fabrication techniques for surgical bone fixation and dental restoration purposes. In one embodiment an all-ceramic single-stage threaded implant is provided having finely detailed surface features formed by injection molding and/or spark plasma sintering of a powder compact or green body comprising powdered zirconia. In another embodiment an all-ceramic single-stage press-fit implant is provided having finely detailed surface features formed by ceramic injection molding and/or spark plasma sintering of a powder compact or green body comprising powdered zirconia. In another embodiment a two-stage threaded implant is provided having an exterior shell or body formed substantially entirely of ceramic and/or CNT-reinforced ceramic composite material. In another embodiment a titanium implant is provided having finely detailed surface features formed by injection molding and/or spark plasma sintering of a powder compact or green body comprising powdered titanium.

In accordance with other embodiments and variations of the invention, detailed surface features may include various unique patterns of dimples, bumps, spikes and/or similar surface features designed to improve primary stability and/or promote healing and osseointegration. Unique surface features may also include one or more frictionally anisotropic bone-engaging surfaces configured to reduce and/or increase friction in a desired direction relative to insertion or removal of the implant. Optionally, at least the bone-engaging portions of the implant are coated with a layer of titanium oxide that is fused to the ceramic surface of the implant via an electric discharge process. Optionally, at least the supragingival portions are densely sintered and annealed in an oxygen atmosphere to produce a ceramic implant having high translucence in the visible light range.

In accordance with other embodiments and variations of the invention, an all-ceramic implant is formed at least in part by sintering a green body formed by slip casting, powder compacting or injection molding a feedstock comprising 3 mol % yttria-stabilized powdered zirconia having an average particle size of about 0.16 μm. Optionally, the entire implant may be molded or powder compacted in green stage to substantially its final geometry (enlarged to account for shrinkage during subsequent sintering), including finely detailed surface texturing and other desired surface features. The green stage implant may be debinded (if a binder is used) and sintered in one or more sintering operations to produce a finished dental implant product that does not require any grinding or machining operations. The green body may be formed by injection molding a ceramic feedstock comprising powdered 3-mol % yttria-stabilized zirconia $(Y_2O_3)_3 (ZrO_2)_{97}$ having an average particle size of less than 0.25 μm and a BET surface area greater than about 8.0 m2/g. The powdered YSZ is first coated with stearic acid by ball-milling with 3 vol % stearic acid solution. The SA-coated powder is then thoroughly mixed with a water-soluble binder until a solids loading of about 48% is reached.

In accordance with other embodiments and variations of the invention, a densely sintered zirconia implant may be formed by sintering a debound injection-molded green body. Prior to sintering, the debound green body is fully or partially immersed in an aqueous solution containing ions and/or particles of silver, gold, titanium, zirconia, YSZ, α-tricalcium phosphate, hydroxyapatite, carbon, carbon nanotubes, and/or other particles sufficiently small in size such that at least some of the particles enter and remain lodged in the implant surface after sintering. In an alternative embodiment, the debound green body may be fully or partially immersed in a colloidal solution containing particles of carbon, carbon nanotubes, and/or other carbon-based particles sufficiently small in size such that at least some of the particles enter and remain lodged in the porous surface of the green body and/or diffuse interiorly to a desired depth. The green body is then fully sintered in a vacuum chamber or other oxygen free environment. After sintering the implant is heated in an oxygen environment until substantially all of the carbon-based particles are fully oxidized and/or burned off leaving a porous outer surface having improved biological compatibility and/or osseointegration characteristics.

In accordance with other embodiments and variations of the invention, a densely sintered zirconia implant may be formed at least in part by spark plasma sintering a powder compact formed by compacting finely powdered 3-mol % yttria-stabilized zirconia having an average particle size less than about 50 nm and a BET surface area greater than about 15 m2/g. The powder compact is pressed into a graphite die by uniaxial pressing followed by cold isostatic pressing producing a compacted green body having a density of around 43% of theoretical density. A pulsed DC current is introduced through a pair of graphite plungers and is caused to pass directly through the powder compact, heating it at a rate exceeding 500° C./min until a maximum sintering temperature of 1050° C. is reached. Mechanical pressure of up to 400 MPa is applied until the powdered material is densely compressed and sintered to a final density greater than about 96.5% of theoretical density. The result is a densely sintered zirconia implant having small grain size (between about 0.1 μm and 1.0 μm in diameter) and finely detailed surface features closely following the internal geometries of the graphite die.

In accordance with other embodiments and variations of the invention, a densely sintered zirconia dental implant is provided having desired translucence properties. The implant is formed at least in part by spark plasma sintering a powder compact formed by compacting finely powdered 3-mol % yttria-stabilized zirconia having an average particle size less than about 30 nm and a BET surface area greater than about 20 m2/g. The powder compact is pressed into a graphite die and compacted until a density of around 43% of theoretical density is achieved. A pulsed DC current is then introduced through a pair of graphite plungers and is caused to pass directly through the powder compact, heating it at a rate exceeding 500° C./min until a maximum sintering temperature of 1100° C. is reached. Mechanical pressure of up to 800 MPa is applied until the powdered material is densely compressed and sintered to a final density greater than about 99.5% of theoretical density. The result is a densely sintered zirconia implant having desired translucence properties.

In accordance with other embodiments and variations of the invention, an implant is provided comprising a CNT-reinforced ceramic composite material. The implant is fabricated by densely sintering a green body formed from a composite powder mixture comprising approximately 98.0 wt % of powdered 3-mol % yttria-stabilized zirconia $(Y_2O_3)_3 (ZrO_2)_{97}$ and approximately 2.0 wt % of SWCNTs. In an alternative embodiment a ceramic composite implant is formed at least in part by densely sintering a green body formed from a composite powder mixture comprising approximately 97.5 wt % of powdered 3-mol % yttria-stabilized zirconia $(Y_2O_3)_3 (ZrO_2)_{97}$ and approximately 2.5 wt % of MWCNTs decorated with silver, gold and/or titanium.

In accordance with other embodiments and variations of the invention, an implant is formed substantially entirely from a non-electrically-conductive ceramic material. At least the bone-engaging surfaces of the implant are surface modified by a PMEDC process to create a strongly bonded titanium oxide layer having desired surface roughness and porosity characteristics. An initial coating of titanium nitride (TiN) is applied to the bone-engaging surfaces of the ceramic implant by physical vapor deposition in order to form a temporary conductive layer for initiating the PMEDC process. During PMEDC a titanium cathode is used which is formed from a partially-sintered powder compact of pure titanium. Pure titanium powder having an average particle size of 100 μm is added to dionized water and is maintained in fluid suspension at a concentration of 40 g/l using a pump having a flow rate of about 20 L/min. The implant is immersed in the fluid suspension and a PMEDC process is carried out until a fused titanium oxide layer is attained having a desired thickness.

For purposes of summarizing the invention and the advantages achieved over the prior art, certain objects and advantages of the invention have been described herein above. Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

BRIEF DESCRIPTION OF THE DRAWINGS

Having thus summarized the general nature of the invention and its essential features and advantages, certain preferred embodiments and obvious modifications thereof will become apparent to those skilled in the art from the detailed description herein having reference to the figures that follow, of which:

FIGS. 5A-C are SEM photographs (taken at 20× magnification) of a post-sintered dental implant having features and advantages in accordance with the embodiment described in connection with FIGS. 4A-E;

FIG. 5D is an SEM photograph (taken at 100× magnification) of the dental implant illustrated in FIGS. 5A-C, showing in more detail the rough molded surface texture achieved at the lower anchor portion thereof;

FIG. 6A is a side plan view of another alternative embodiment of a single stage threaded implant having features and advantages in accordance with the present invention;

FIG. 6B is a longitudinal cross-sectional view of the single stage threaded implant of FIG. 6A;

FIGS. 7A and 7B are side plan views of additional alternative embodiments of a single stage threaded implant having features and advantages in accordance with the present invention;

FIGS. 8A and 8B are schematic illustrations of various isotropic and anisotropic surface features that may be provided or formed on one or more bone-engaging surfaces of a threaded or unthreaded implant in accordance with the present invention;

FIG. 9A is a side plan view of a two stage threaded implant having features and advantages in accordance with the present invention;

FIG. 9B is a partial cross-sectional view of the lower anchoring portion of the two stage threaded implant of FIG. 9A;

FIG. 9C is an exploded assembly view of the two stage threaded implant of FIG. 9A;

FIG. 9D is a longitudinal cross-sectional view of the two stage threaded implant of FIG. 9A;

FIG. 11A is a side plan view of a single stage press-fit implant having features and advantages in accordance with the present invention;

FIG. 11B is a top plan view of the single stage press-fit implant of FIG. 11A;

FIG. 11C illustrates an implant system comprising multiple alternative configurations of a single stage press-fit implant having features and advantages in accordance with the present invention;

FIG. 11D illustrates an optional system comprising multiple implant analogues having configurations corresponding to each implant configuration illustrated in FIG. 11C;

FIG. 19 is a schematic diagram of an electric discharge coating process for coating a ceramic implant with a fused layer of titanium oxide and having features and advantages in accordance with the present invention;

FIGS. 20 and 21 are schematic diagrams of a powder mixed electric discharge coating process for coating a ceramic implant with a fused layer of titanium oxide and having features and advantages in accordance with the present invention;

Figure 2:
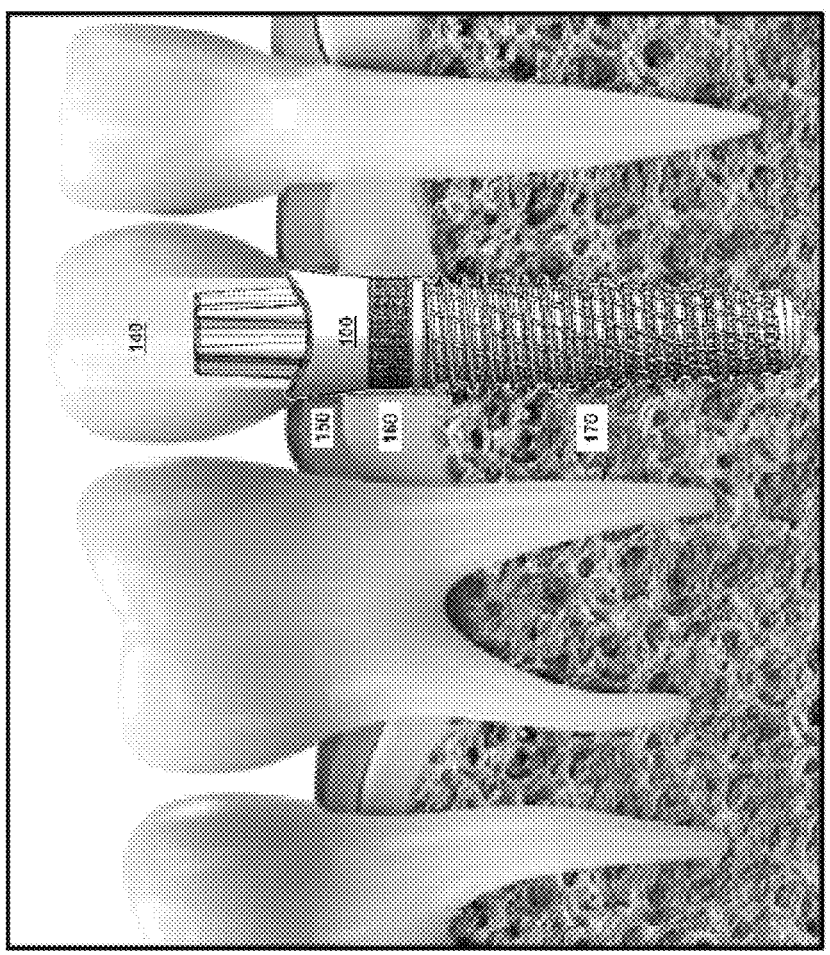
FIG. 2 is a partial cross-section view illustrating the placement of a threaded implant within the alveolar bone of a patient.

For convenience of description and for better clarity and understanding of the invention, similar elements in different figures may be identified with similar or even identical reference numerals. However, not all such elements in all embodiments are necessarily identical as there may be differences that become clear to persons skilled in the art when read and understood in the context of each particular disclosed preferred embodiment.

DETAILED DESCRIPTION

The attached figures and accompanying disclosure illustrate and describe multiple embodiments of various surgical implants and associated tools, components and fabrication techniques having features and advantages of the invention as more-fully described herein. All of these embodiments are intended to be within the scope of the invention herein disclosed. These and other embodiments and obvious variations of the present invention will become readily apparent to those skilled in the art from the following detailed description of the preferred embodiments having reference to the attached figures, the invention not being limited to any particular preferred embodiment(s) disclosed.

Definitions

The following terms as used herein in the specification and in the claims shall be defined and understood as follows, regardless of any other ordinary or understood meanings, dictionary definitions, definitions in documents incorporated by reference, or other possible meanings of the defined terms:

The indefinite articles "a" and "an" should be understood to mean at least one.

The conjunctive phrase "and/or" should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

The phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

The phrase "communicatively coupled" or "communicative coupling" means that there is a path or channel of communication from one component to another, whether the path is direct or indirect and whether such path includes a path through one or more intervening component.

The conjunctive article "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either,"

"one of," "only one of," or "exactly one of." When a range of "about X to Y" or "between about X and Y" is stated, the range includes from about X to about Y or between about X and about Y.

Acronyms

Figure 1:
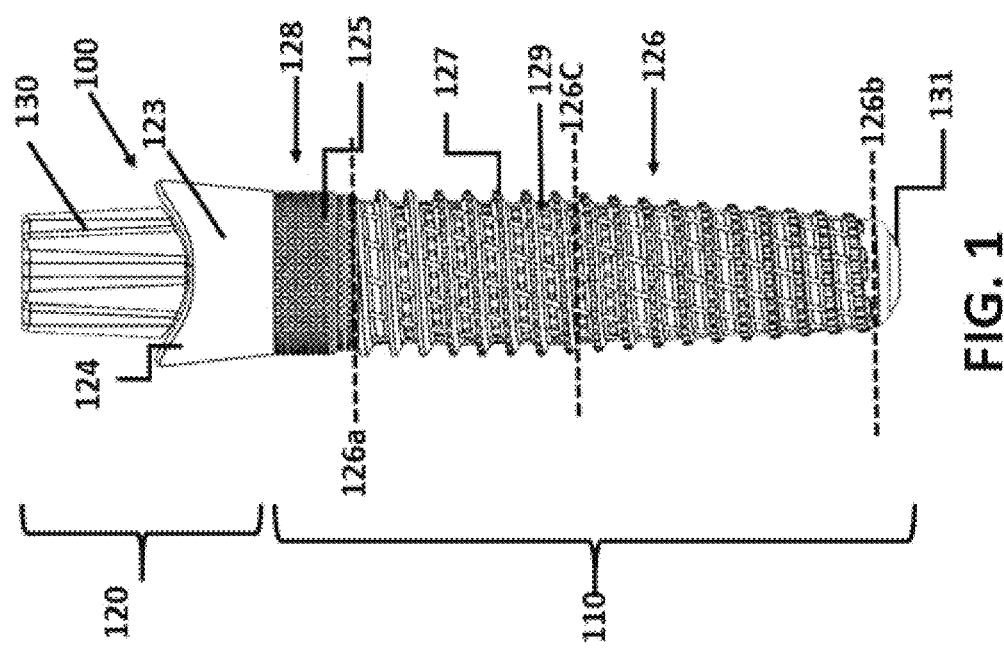
FIG. 1 is a side plan view of one embodiment of a single stage threaded implant having features and advantages in accordance with the present invention.

For the convenience of the reader certain acronyms and abbreviations used herein in the specification and claims are listed below:
BET Brunauer, Emmett and Teller technique
CIP cold isostatic pressing
CL conductive layer
CNT carbon nanotube
CT computed tomography
CTE coefficient of thermal expansion
DI dionized water
DLC diamond-like carbon
EDC electric discharge coating
EDM electrical discharge machining
FAST field-assisted sintering technique
FDA Food and Drug Administration
FESEM field emission scanning electron microscope
HIP Hot isostatic pressing
LTCC low-temperature co-fired ceramic
MWCNT multi-walled carbon nanotube
MWS Microwave sintering
NEMS nano-electro-mechanical system
PECS pulsed electric current sintering
PEG polyethylene glycol
PMEDC powder mixed electric discharge coating
PMMA polymethylmethacrylate
POM Polyoxymethylene
PVB polyvinyl butyral
SA stearic acid
SEM scanning electron microscope
SPS spark plasma sintering
SWCNT single-walled carbon nanotube
YSZ yttrium-stabilized zirconia Single Stage Threaded Implant FIG. 1 is a side plan view of one embodiment of a single stage threaded implant 100 having features and advantages of the present invention. Preferably the entire implant 100 is formed from a suitable ceramic material such as yttrium-stabilized zirconia which is densely sintered and molded to a final desired geometry, as will be described in more detail later. Alternatively, the implant 100 may be formed as a densely sintered ceramic blank which is then machined to a final desired geometry by grinding and/or other machining steps. Alternatively, the implant 100 may be formed from a blank of pure titanium, titanium alloy, or other suitable material by molding, casting, rolling, forging, grinding and/or other machining operations. Alternatively, the implant 100 may be formed in two or more mating pieces configured to be permanently and/or removably secured to one another either before, during or after use in one or more surgical procedures. This may be accomplished, for example, using one or more mating screws or fasteners, and/or using a suitable cement or bonding agent such as zinc phosphate or polycarboxylate.

As illustrated in FIG. 1, the implant 100 generally comprises an anchoring portion 110 configured to extend subgingivally into an osteotomy formed within the alveolar bone (either the maxilla or the mandible), and an abutment portion 120 connected to and preferably integrally-formed with the anchoring portion 110 and configured to extend through the gingiva 150 (see, e.g., FIG. 2) into the oral cavity to support a prosthetic tooth 140 (see, e.g., FIG. 2) or other structure(s) desired to be secured. The implant is configured to be surgically inserted into a threaded or unthreaded osteotomy formed within the alveolar bone of a patient. As illustrated in more detail in FIG. 2, the alveolar bone typically consists of both hard/dense cortical bone 160 and relatively soft/spongy cancellous bone 170, as illustrated.

Referring again to FIG. 1, the anchoring portion 110 of the implant 100 generally comprises a soft-bone-engaging lower anchoring portion 126 and a hard-bone-engaging upper anchoring portion 128. The lower anchoring portion 126 comprises a generally tapered round or cylinder-like body extending from a proximal end 126a (nearest the oral cavity) to a distal end 126b (furthest from the oral cavity) and one or more threads 127 configured to engage the soft cancellous bone tissue 170 (see FIG. 2). The tapered body is preferably widest at the proximal end and smallest at the distal end and may have a constant or variable (e.g., accelerating or decelerating) rate of taper from the proximal to the distal end. In one embodiment the distal end 126b of the lower anchoring portion 126 may be 20% to 60% smaller in diameter than the proximal end 126a. In another embodiment the distal end 126b may be 38% smaller in diameter than the proximal end 126a. Preferably, the taper rate accelerates from approximately 0 mm/mm) (0° at the proximal end 126a to approximately 0.1625 mm/mm)(4.6° at the distal end 126b. In alternative embodiments, the taper rate may vary from approximately 0 mm/mm)(0° to approximately 0.36 mm/mm)(10° and may accelerate, decelerate, or remain constant along the length thereof. The lower anchoring portion 126 may have a diameter ranging from 2.5 mm to 7.5 mm and a length ranging from 3 mm to 12 mm, as desired or expedient. If desired, the distal end 126b of the implant may terminate in a single-reducing or double-reducing chamfer 131, as illustrated in FIG. 1. Of course, a wide variety of geometrically similar implant designs formed in various shapes, sizes and dimensions are possible and desirable according to the particular clinical indication and the particular needs and desires of the patient.

Preferably, the lower anchoring portion 126 is formed with a single continuous clockwise thread 127 that extends helically and/or spirally from the proximal end 126a to the distal end 126b thereof. Preferably the thread 127 has a pitch of between about 0.4 mm to 0.8 mm or about 15%-25% of the major thread diameter Dt at or near the proximal end 126a and, more preferably, about 18% of the major thread diameter Dt at or near the proximal end 126a (See FIG. 3C). The major thread diameter Dt at or near the proximal end 126a is preferably about 3-6 mm and is slightly larger (e.g., by about 0.5%-5%, more preferably by about 1%-3%, and most preferably by about 1.5%) than the diameter D1 of the upper anchoring portion 128. The minor thread diameter at or near the proximal end 126a is preferably 10%-20% smaller and, more preferably, about 15% smaller than the major thread diameter Dt at or near the proximal end 126a. The thread depth is preferably about 5-10% of the major thread diameter Dt at or near the proximal end 126a and, more preferably, about 8% of the major thread diameter Dt at or near the proximal end 126a.

Figure 3A:
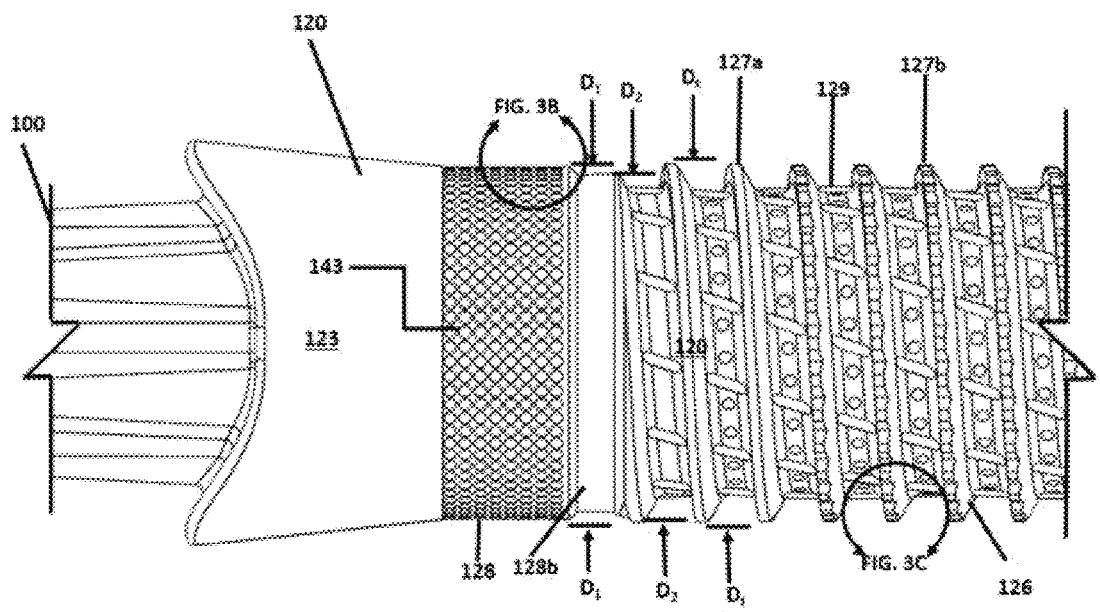
FIG. 3A is a side plan view of an alternative embodiment of a single stage threaded implant having features and advantages in accordance with the present invention.
Figure 3B:
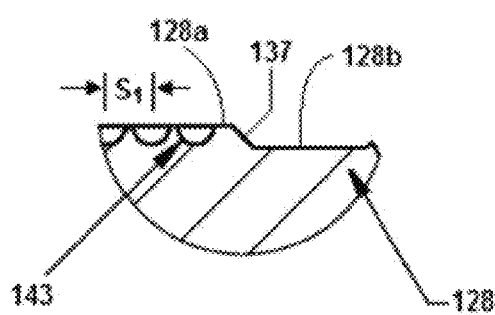
FIG. 3B is a partial sectional view of the upper anchoring portion of the single stage threaded implant of FIG. 3A.
Figure 3C:
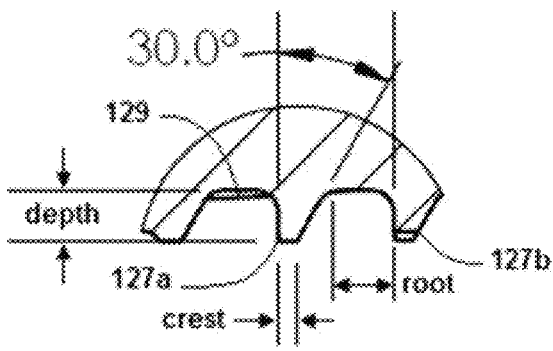
FIG. 3C is a partial sectional view of the lower anchoring portion of the single stage threaded implant of FIG. 3A.

The preferred thread profile is a truncated 30° saw tooth shape having a neutral or slightly positive (e.g., 3° to)5° rake angle relative to the pull-out direction of the implant 100, as illustrated in more detail in FIG. 3C. The root or spacing between adjacent threads is preferably about 40%-60% of the thread pitch and, more preferably, about 50% of the thread pitch. A flattened, angled and/or rounded crest is preferably formed at the outer-most edge of the thread 127 and preferably has a width of about 10%-20% of the thread pitch and, more preferably, about 16% of the thread pitch. Preferably, the thread pitch, the saw tooth profile and the crest width remain substantially constant from the proximal end 126*a* to the distal end 126*b*. Preferably the thread profile and thread depth remain substantially constant from the proximal end 126*a* to an inflexion point 126*c* located approximately one-third of the distance from the proximal end 126*a* to the distal end 126*b*, as illustrated in FIG. 1. From the inflexion point 126*c* to the distal end 126*b* preferably the thread depth decreases at a constant and/or accelerating rate, reducing from about 8% of the major thread diameter at or near the inflexion point 126*c* to less than about 1-2% of the major thread diameter at or near the distal end 126*b*, as illustrated in FIG. 1.

As illustrated in more detail in FIG. 3A, the thread 127 may either be continuous (e.g., smooth thread 127*a*) and/or discontinuous (e.g., notched or serrated thread 127*b*). Preferably, the thread 127 is notched or serrated along at least a portion of its length, as best illustrated in FIGS. 3A and 4. Advantageously, it has been discovered that providing such notches or serrations reduces sliding friction during implant insertion, increases static friction post-insertion, increases the ratio of static to sliding friction, increases surface area, increases mechanical bone engagement, improves primary stability and/or improves the osseointegrative properties of the implant 100. If desired, two or more continuous or discontinuous threads (not shown) may be provided, for example, where it is desired to introduce a second thread having a different thread pitch, thread profile, major thread diameter, thread depth and/or helix angle than a first thread. For example, two parallel threads may be provided wherein, the first thread is substantially discontinuous, notched or serrated along its length and has a relatively larger major thread diameter and wherein the second thread is substantially continuous or non-serrated and has a relatively smaller major thread diameter.

If desired, one or more cutting edges may also be formed or provided on the thread 127 at or near the distal end 126*b* of the lower anchoring portion 126 and/or between the distal end 126B and the inflexion point 126*c* so as to provide a self-tapping and/or self-drilling capability in accordance with any one of a number of well-known self-tapping and/or self-drilling thread designs. Preferably, saw-tooth-like cutting edges are formed in the thread 127 between the distal end 126B and the inflexion point 126*c* so as to provide a self-tapping capability wherein mating threads are cut into the surrounding bone tissue as the implant 100 is threaded into an unthreaded or partially-threaded osteotomy. If desired, the spacing, depth and/or rake angle of the cutting edges may be varied from the distal end 126*b* to the inflexion point 126*c* so as to minimize friction and cutting forces and/or to maximize fracture resistance. Preferably, any cutting edges formed in thread 127 are substantially evenly spaced along the crest of the thread and increase in depth from the distal end 126*b* to the inflexion point 126*c*. Preferably, such cutting edges have associated rake angles that gradually decrease from neutral or slightly positive (e.g., 0° to)5° at the distal end 126*b* to substantially negative (e.g., −30° to −45°) at or near the inflexion point 126*c*. If desired, any one or more of the cutting edges may be formed with an oblique rake angle so as to reduce friction and associated cutting forces. Optionally, the cutting edges may be formed with alternating positive and negative rake angles and/or alternating oblique rake angles, as desired.

Figure 3D:
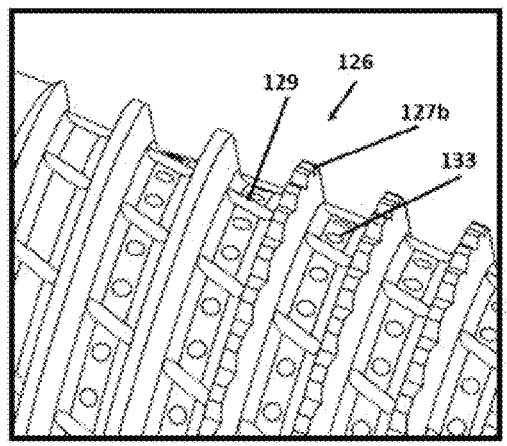
FIG. 3D is a detail view of the lower anchoring portion of the single stage threaded implant of FIG. 3A, illustrating various unique surface geometries having features and advantages in accordance with the present invention.

As illustrated in more detail in FIG. 3D, multiple tie rods 129 are preferably provided between each adjacent thread 127 in a regular or irregular spaced pattern. Tie rods 129 are preferably raised surface features which are directly molded, machined or otherwise integrally formed with the lower anchoring portion 126 of the implant body between adjacent threads 127. In the particular embodiment illustrated in FIGS. 1-3 the tie rods 129 are arranged in a staggered pattern around the lower anchoring portion 126 forming a clockwise helical sweep path from the proximal end 126*a* to the distal end 126*b* thereof, as best illustrated in FIGS. 1 and 3A. Other similar raised or sunken finely detailed surface features (e.g., geometrical features ranging in size from about 25-150 μm) may also be provided on various bone-engaging surfaces of the implant 100 as desired or expedient, such as for example and without limitation, in the form of dimples, bumps or ridges. Any or all of these optional surface features may be provided in various shapes, sizes, combinations and arrangements, as desired, such as illustrated and described in more detail later in connection with FIGS. 8A and 8B. For example, an alternating combination of tie rods 129 and round dimples 133 may be provided in a regular spaced pattern between adjacent threads 127, as illustrated in FIG. 3D. This pattern may repeat or continue along the entire thread 127 as it winds from the proximal to the distal end and/or it may repeat or continue along only one or more portions of the thread 127, as illustrated in FIG. 3D. Alternatively, the size, shape, combination and/or arrangement of such surface features may be varied along the path of the thread 127, as desired, so as to provide a variety of bone-engaging surface features such as illustrated in FIG. 3D, for example.

Preferably, these and/or other similar raised or sunken features are formed with a maximum height or depth relative to the implant surface of less than about 0.15 mm or about 4% of the local diameter of the implant 100 and, more preferably, less than about 0.05 mm or about 1% of the local diameter of the implant 100. Advantageously, the combination of these and/or similar raised and/or sunken surface features, such as dimples, bumps and ridges, increases mechanical engagement and promotes in-growth and adhesion of live bone tissue, thereby improving primary stability and promoting healing and osseointegration. The tie rods 129 also increase the torsional strength of the lower anchoring portion 126 thereby increasing its torsional fracture resistance. The tie rods 129 and/or similar structures may also advantageously help remove and/or transport bone debris away from the hard cortical bone 160 during insertion of the implant 100 into a threaded or unthreaded osteotomy. Preferably, the tie rods 129 have a height of about 0.15 mm, a width of about 0.3 mm and a length of about 0.32 mm. Dimples 133 preferably have an average diameter of about 0.130 mm and an average depth of about 0.065 mm. Alternatively, the size and/or depth of the dimples 133 may be varied in a regular or irregular (e.g., random) pattern, if desired, so as to provide a surface that promotes mechanical engagement, adhesion and in-growth of live bone tissue. Alternatively, some or all of the dimples 133 may be replaced with similarly-sized bumps or alternating and/or varying combinations of dimples, bumps and/or other desired surface features as desired.

The upper anchoring portion 128 is designed to engage the hard/dense cortical bone 160 (e.g., see FIG. 2) in a manner that optimally achieves both primary stability and long-term osseointegration. As illustrated in more detail in FIG. 3A, the upper anchoring portion 128 is generally formed as a stepped cylinder having a first portion 128*a* configured to engage the hardest/densest part of the cortical bone near the surface thereof, and a second portion 128*b* configured to engage the less hard/dense part of the cortical bone located 1-2 mm below the surface thereof and/or the transition region between the cortical bone and the softer cancellous bone. The upper anchoring portion 128 is preferably about 1.5 mm to 2 mm in total length, and wherein the first portion 128a comprises about two-thirds and the second portion 128b comprises about one-third of this total length. Preferably, the first portion 128a has a first diameter D1 that is about 3% to 8% larger than the second diameter D2 of the second portion 128b and, more preferably, about 4% to 5% larger. The stepped transition 137 (see, e.g., FIG. 3B) between the first and second portions 128a, 128b may be square, chamfered or curved, as desired or expedient. Optionally, the stepped transition 137 may include one or more downward-facing cutting edges or teeth (not shown) configured and arranged to cut or expand a slightly-undersized osteotomy (e.g., an osteotomy that is 3% to 8% smaller and, more preferably, about 4% to 5% smaller than the first diameter D1) while the threaded implant 100 is being inserted therein. Optionally, the stepped transition 137 may be coated or impregnated with a temporary bonding or sealing agent and/or an antibacterial coating such as silver ions or the like.

Figure 3E:
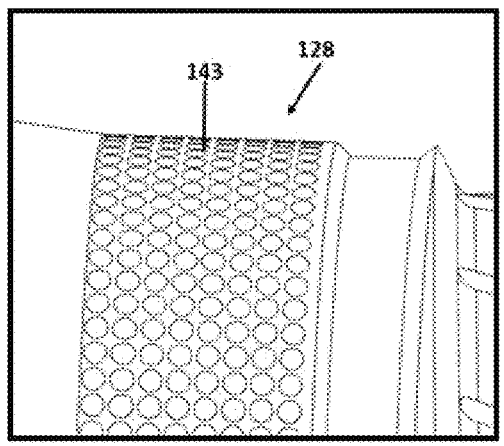
FIG. 3E is a detail view of the upper anchoring portion of the single stage threaded implant of FIG. 3A, illustrating various unique surface geometries having features and advantages in accordance with the present invention.

Preferably, the outer bone-engaging surface of one or both of the first and second portions 128a, 128b are densely covered with multiple raised and/or sunken surface features, such as dimples, bumps or ridges, arranged in a regular or irregular spaced pattern (e.g., dimples 143 shown in FIGS. 3A and 3B). These raised and/or sunken surface features are preferably directly molded or otherwise integrally formed with the upper anchoring portion 128 of the implant body and have a packing density of greater than about 0.65, more preferably greater than about 0.85, and most preferably greater than about 0.90. In the particular preferred embodiment illustrated in FIGS. 1-3 a plurality of similarly-sized dimples 143 are arranged in a square-packed lattice pattern, as illustrated in FIG. 3E, and have a packing density of about 0.75. Alternatively, other suitable lattice packing configurations may be employed, as desired, including without limitation, square, truncated square, snub square, hexagonal, snub hexagonal, tri-hexagonal, truncated tri-hexagonal, triangular, elongated triangular, or rhombi-tri-hexagonal. Square or hexagonal lattice packing configurations are particularly preferred.

Preferably, these and/or other similar raised and/or sunken features are formed with a maximum height or depth relative to the implant surface equal to or less than about 0.15 mm or about 4% of the local diameter of the implant 100. In an alternative embodiment, these and/or other similar raised and/or sunken features are formed with a maximum height or depth relative to the implant surface equal to or less than about 0.05 mm or about 1% of the local diameter of the implant 100. Advantageously, the combination of these and similar raised and/or sunken surface features, such as dimples, bumps and ridges, increases the surface area and mechanical engagement of the implant and encourages in-growth and adhesion of live bone tissue, thereby improving primary stability and promoting healing and osseointegration. Dimples 143 preferably have an average diameter of about 0.130 mm, an average depth of about 0.065 mm and are preferably spaced apart between 0.13 mm and 0.18 mm from center to center and, more preferably about 0.15 mm from center to center, in a square packing or hexagonal packing arrangement. Alternatively, the size and/or depth of the dimples 143 may be varied in a regular or irregular (e.g., random or fractal) pattern, if desired, so as to provide an improved bone-engaging surface that increases mechanical engagement and promotes in-growth and adhesion of live bone tissue. Optionally, some or all of the dimples 143 may be replaced with raised bumps, studs, spurs, spikes, knurling and/or similar raised surface features for providing enhanced gripping, frictional anisotropy, resistance to rotation and/or additional desired bone engagement and increased primary stability. If present, these raised features create limited localized residual stresses at the point where each bump or other raised surface feature presses into the surrounding hard cortical bone tissue 160.

Referring again to FIG. 1, the abutment portion 120 of the implant 100 preferably comprises a smoothly tapered transgingival portion 123 configured to emerge from the anchoring portion 110 through the gingiva in a desired emergence profile, and a supragingival portion 130 comprising a post-like structure configured to extend into the oral cavity to receive and support a prosthetic tooth or other restorative structure such as an anatomically-functional aesthetic porcelain crown. Preferably, the transgingival portion 123 has a machined or polished biologically inert surface that provides a good sealing interface with the surrounding soft gum tissues and prevents or resists the accumulation of plaque and calculus thereon. If desired, the transgingival portion 123 may be shaped and contoured in accordance with any number of tooth emergence profiles as may be desired. Suitable emergence profiles may include, for example, simple rotationally symmetric shapes (e.g., round or conical), bilaterally symmetric shapes (e.g., ovular), radially symmetric shapes (e.g., triangular or hexagonal), compound curves, complex curves, and/or other arbitrary or asymmetric shapes (e.g., shapes mimicking or approximating the emergence profile of a natural tooth being replaced). In one embodiment, a suitable emergence profile is formed as an outwardly-opening flattened or ovular-shaped truncated cone that is substantially circular at the narrower end and substantially ovular at the wider end (see, e.g., FIG. 11B). The distal edge 124 of the transgingival portion 123 may also be contoured or shaped as desired. For example, the buccal and lingual sides of the transgingival portion 123 may be shaved down or undercut, as illustrated in FIG. 1, in order to more closely follow the crescent-shaped gum lines of a natural tooth being replaced.

The supragingival portion 130 preferably comprises a post-like structure having a tapered anti-rotational cross-section (e.g., hex, square, star, and/or the like) configured to extend into the oral cavity to receive and support a porcelain crown or other restorative device or structure. This may be bonded or cemented directly to the supragingival portion 130 using a suitable bonding agent such as zinc phosphate or polycarboxylate. Preferably, a torque driver or similar tool (see, e.g., FIGS. 12A-12E) is provided with a similarly-configured female socket having a mating anti-rotational cross-section (e.g., hex, square, star, and/or the like) configured to matingly engage and apply a desired amount of torque to the supragingival portion 130 to drive the threaded implant 100 into an osteotomy to a final desired depth.

Figure 4A:
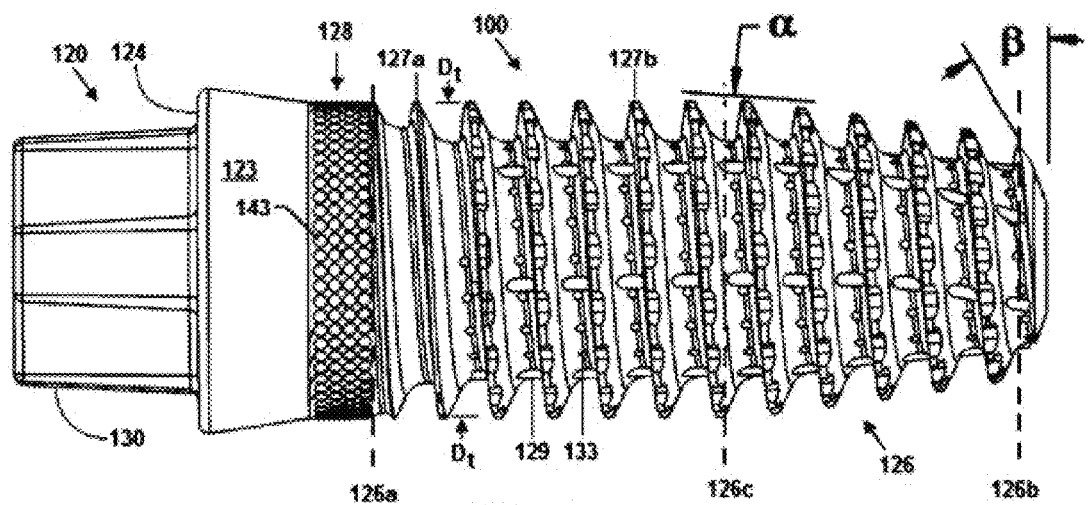
FIG. 4A is a side plan view of an alternative embodiment of a single stage threaded implant having features and advantages in accordance with the present invention.
Figure 4B:
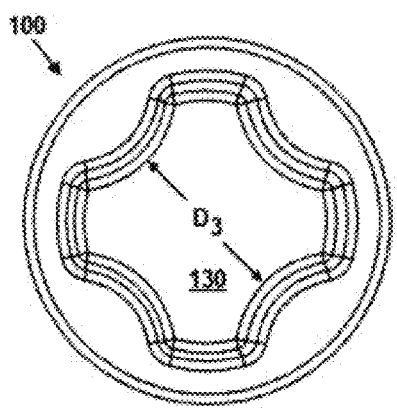
FIG. 4B is a top plan view of the single stage threaded implant of FIG. 4A as viewed from the proximal end thereof.
Figure 4C:
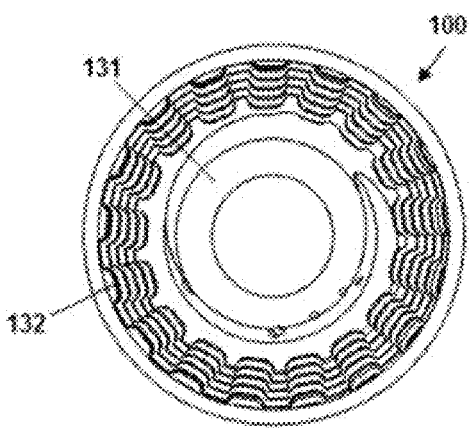
FIG. 4C is a bottom plan view of the single stage threaded implant of FIG. 4A as viewed from the distal end thereof.
Figure 4D:
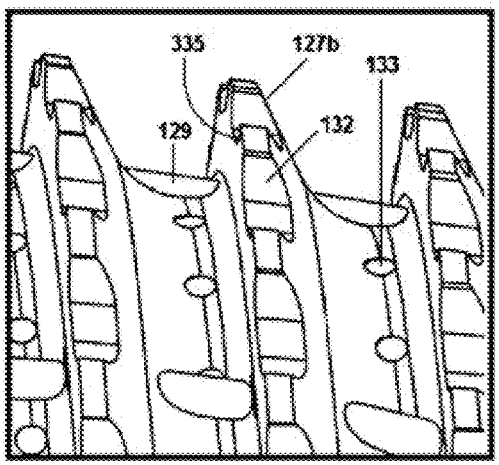
FIG. 4D is a detail view of the lower anchoring portion of the single stage threaded implant of FIG. 4A, illustrating various unique surface geometries having features and advantages in accordance with the present invention.
Figure 4E:
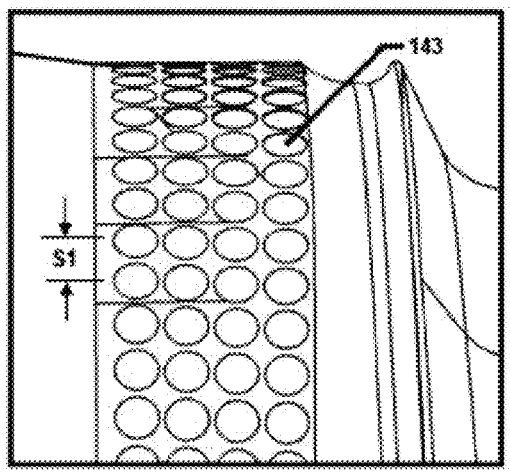
FIG. 4E is a detail view of the upper anchoring portion of the single stage threaded implant of FIG. 4A, illustrating various unique surface geometries having features and advantages in accordance with the present invention.

FIGS. 4A-C are side, top, and bottom plan views, respectively, of a modified embodiment of the single stage threaded implant 100 illustrated and described above in connection with FIGS. 1-3 and having features and advantages of the present invention. FIGS. 4D-E are detail views of the modified implant of FIGS. 4A-C. The threaded implant illustrated in FIGS. 4A-E is similar or identical in design and construction to the implant illustrated and described above in connection with FIGS. 1-3, with the exception of certain features which are described in more detail below.

As noted above, preferably the lower anchoring portion 126 is formed with a single continuous clockwise thread 127 that extends helically and/or spirally from the proximal end 126a to the distal end 126b thereof. Preferably the thread 127 has a pitch of 0.775 mm or about 19% of the major thread diameter Dt at or near the proximal end 126a (see, e.g., FIG. 4A). The major thread diameter Dt at or near the proximal end 126a is preferably about 4.00 mm and is slightly smaller (by 0.10 mm or about 2.5%) than the largest diameter D1 of the upper anchoring portion 128. The minor thread diameter at or near the proximal end 126a is preferably about 25% smaller than the major thread diameter Dt at or near the proximal end 126a. The thread depth is preferably about 0.513 mm or 12.8% of the major thread diameter Dt at or near the proximal end 126a. The major thread diameter Dt at or near the distal end 126b is preferably about 3.17 mm or about 21% smaller than at the proximal end 126a. The minor thread diameter at or near the distal end 126b is preferably about 23% smaller than the major thread diameter Dt at or near the distal end 126b. The thread depth at or near the distal end 126b is preferably about 0.364 mm or 11.5% of the major thread diameter Dt at or near the distal end 126b.

The preferred thread profile is a truncated 30° saw tooth shape having a substantially square gripping edge 335 formed with neutral rake angle (i.e., orthogonal) relative to the pull-out direction of the implant 100, as illustrated in more detail in FIG. 4D. The root or spacing between adjacent threads is preferably 0.412 mm or about 53% of the thread pitch. A flattened crest is preferably formed at the outer-most edge of the thread 127 and preferably has a width of 0.126 mm or about 16% of the thread pitch at the proximal end 126a gradually widening to about 0.198 mm or about 25% of the thread pitch at or near the distal end 126b. Preferably, the thread pitch and the saw tooth profile remain substantially constant from the proximal end 126a to the distal end 126b. Preferably the thread profile and thread depth remain substantially constant from the proximal end 126a to an inflexion point 126c located approximately half the distance from the proximal end 126a to the distal end 126b, as illustrated in FIG. 4A. From the inflexion point 126c to the distal end 126b preferably the thread depth decreases at a substantially constant rate, reducing from 0.500 mm or about 12.5% of the major thread diameter Dt at or near the inflexion point 126c to 0.364 mm or about 11.5% of the major thread diameter Dt at or near the distal end 126b, as best illustrated in FIG. 4A.

The thread 127 is preferably continuous for the first 2 thread revolutions 127a starting from the proximal end 126a and then transitioning to a notched or serrated thread 127b for the remaining portions thereof to the distal end 126b. Preferably, the thread 127 is notched with truncated V-notches 132, as best illustrated in FIGS. 4C and 4D. The truncated V-notches 132 are preferably equally radially spaced with a radial spacing of about 21.2°. Alternatively, the V-notches 132 may be equally spaced linearly along the thread path or variably spaced, as desired. If desired, the shape of the truncated V-notches may be varied gradually and/or discretely so as to provide, for example, more aggressive cutting or scraping action (e.g. less-negative rake angles and/or more oblique cutting angles) at or near the distal end 126b of the lower anchoring portion 126 and/or between the distal end 126B and the inflexion point 126c so as to provide a self-tapping and/or self-drilling capability. For example, saw-tooth-like cutting edges may be formed in the thread 127b between the distal end 126b and the inflexion point 126c so as to provide a self-tapping capability wherein mating threads are cut into the surrounding bone tissue as the implant 100 is threaded into an unthreaded or partially-threaded osteotomy. If desired, the spacing, depth and/or rake angle of the cutting edges may be varied from the distal end 126b to the inflexion point 126c so as to minimize friction and cutting forces and/or maximize fracture resistance. Preferably, any cutting edges formed in thread 127b are substantially evenly spaced along the crest of the thread and increase in depth from the distal end 126b to the inflexion point 126c. Preferably, such cutting edges have associated rake angles that gradually decrease from neutral or slightly positive (e.g., 0° to)5° at the distal end 126b to substantially negative (e.g., −30° to −45°) at or near the inflexion point 126c. If desired, any one or more of the cutting edges may be formed with an oblique rake angle so as to reduce friction and associated cutting forces. Optionally, the cutting edges may be formed with alternating positive and negative rake angles and/or alternating oblique rake angles, as desired.

Multiple tie rods 129 are preferably provided between each adjacent thread 127 in a regular spaced pattern. Tie rods 129 are preferably raised surface features which are directly molded and integrally formed with the lower anchoring portion 126 of the implant body between adjacent threads 127, as illustrated in more detail in FIG. 4D. In the particular embodiment illustrated in FIGS. 4A-E the tie rods 129 are substantially equally radially and linearly spaced from the proximal end 126a to the inflexion point 126c. From the inflexion point 126c to the distal end 126b the tie rods 129 are preferably equally linearly spaced along the inner root of the thread 127b forming a clockwise helical sweep path along the lower anchor portion 126 from the inflexion point 126c to the distal end 126b thereof, as best illustrated in FIG. 4A. Preferably, starting with at least the second thread revolution from the proximal end an alternating combination of tie rods 129 and round dimples 133 are provided in a regular spaced pattern between adjacent threads 127, as best illustrated in FIGS. 4A and 4D. This pattern preferably continues and repeats along the remaining portion of the thread 127 until it reaches the distal end 126b. Preferably, the tie rods 129 and dimples 133 are formed with a maximum height or depth relative to the implant surface of less than about 0.15 mm or about 5% of the local diameter of the implant 100 and, more preferably, less than about 0.05 mm or about 1.5% of the local diameter of the implant 100. Preferably, the tie rods 129 have a height of about 0.10 mm, a width of about 0.10 mm and a length of about 0.4 mm. Dimples 133 preferably have an average diameter of about 0.210 mm and an average depth of about 0.075 mm.

The upper anchoring portion 128 is generally formed as a short cylinder having a total length of between about 0.75 and 1.0 mm, more preferably, about 0.875 mm. Preferably, the outer bone-engaging surface of the upper anchoring portion 128 is densely covered with 3-4 equally spaced rows of hemispherical dimples 143 having a radius of 0.125 mm and arranged in a square or hexagonal packing pattern with an average center-to-center spacing S1 of 0.280 mm (see FIG. 4E). Alternatively, the size and/or depth of the dimples 143 may be varied in a regular or irregular (e.g., random or fractal) pattern, if desired, so as to provide an improved bone-engaging surface that increases mechanical engagement and promotes in-growth and adhesion of live bone tissue. Optionally, some or all of the dimples 143 may be replaced with raised bumps, studs, spurs, spikes, knurling and/or similar raised surface features for providing enhanced gripping, frictional anisotropy, resistance to rotation and/or additional desired bone engagement and increased primary stability. If present, these raised features create limited localized residual stresses at the point where each bump or other raised surface feature presses into the surrounding hard cortical bone tissue 160.

As illustrated in FIG. 4A the abutment portion 120 of the implant 100 preferably comprises a smoothly tapered transgingival portion 123 configured to emerge from the anchoring portion 110 through the gingiva in a desired emergence profile, and a supragingival portion 130 comprising a post-like structure configured to extend into the oral cavity to receive and support a prosthetic tooth or other restorative structure such as an anatomically-functional aesthetic porcelain crown. Preferably, the transgingival portion 123 has a smooth polished biologically inert surface that provides a good sealing interface with the surrounding soft gum tissues and prevents or resists the accumulation of plaque and calculus thereon. A suitably smooth surface may be formed, for example, by direct molding and sintering as described herein. If desired, the transgingival portion 123 may be molded, shaped and/or contoured in accordance with any number of tooth emergence profiles as may be desired. Suitable emergence profiles may include, for example, simple rotationally symmetric shapes (e.g., round or conical), bilaterally symmetric shapes (e.g., ovular), radially symmetric shapes (e.g., triangular or hexagonal), compound curves, complex curves, or other arbitrary or asymmetric shapes (e.g., shapes mimicking or approximating the emergence profile of a natural tooth being replaced).

As with the other embodiments described above, the supragingival portion 130 of the implant 100 preferably comprises a tapered post 130 having a generally square or quad-lobed cross-section (e.g., FIG. 4B). The post 130 is configured to extend into the oral cavity to receive and support a porcelain crown or other restorative device or structure. Preferably, a tapered post having a smoothly-curved quad-lobed cross section is provided. The post 130 preferably has a minor diameter D3 at its widest point (closest to the transgingival portion 123) of about 2.40 mm, tapering to about 2.25 mm at its narrowest point (furthest from the transgingival portion 123). The edges of each lobe preferably have an external radius R1 of between about 0.12 mm and 0.24 mm and a transition radius R2 of between about 0.20 mm and 0.40 mm. Preferably, a torque driver or similar tool is provided with a similarly-configured quad-lobed female socket configured to matingly engage and apply a desired (preferably limited) amount of torque to the supragingival portion 130 so as to drive the threaded implant 100 into an osteotomy to a final desired depth (see, e.g., FIGS. 12A-E and the accompanying discussion herein).

Preferably, the entire implant 100, including substantially all finely detailed surface features and surface texturing described herein, is injection molded and sintered to substantially its final geometry (the mold being slightly oversized to account for shrinkage during subsequent sintering). The post-sintered dental implant advantageously requires substantially no additional grinding, machining or chemical etching operations prior to final sterilization and packaging. Optionally, some additional machining operations or resurfacing (e.g., deburring, polishing, etching, or sharpening) may be performed either before or after final sintering.

FIGS. 5A-C are SEM photographs (taken at 20× magnification) of a post-sintered molded ceramic implant 100 having features and advantages in accordance with the embodiment described in connection with FIG. 4A-E. As can be seen from the SEM photographs, substantially all of the detailed surface features (e.g., tie rods, dimples, V-notches, etc.) are able to be molded directly into the implant 100 and are substantially retained throughout the debinding and sintering processes (described in more detail later). All final surface finishes and texturing are also able to be molded directly into the implant 100 in accordance with the present invention. For example, FIG. 5A shows different surface finishes provided at the supragingival portion 130 (average surface roughness (Sa) of 1.952 μm and a peak-to-peak surface roughness (Sz) of 28.88 μm), transgingival portion 123 (average surface roughness (Sa) of 0.053 μm and a peak-to-peak surface roughness (Sz) of 1.636 μm), upper anchor portion 128 (average surface roughness (Sa) of 1.972 μm and a peak-to-peak surface roughness (Sz) of 23.91 μm), and lower anchor portion 126 (average surface roughness (Sa) of 2.530 82 m and a peak-to-peak surface roughness (Sz) of 36.27 μm). These and other desired surface finishes are directly molded into the implant 100 by selectively machining, electro-machining (e.g., EDC or PMEDC), polishing, sandblasting, and/or etching the final mold from which the implant 100 is produced. FIG. 5D is an SEM photograph (taken at 100× magnification) of the dental implant 100 illustrated in FIGS. 5A-C, showing in more detail the molded surface texture achieved at the lower anchor portion thereof. The rough molded surface is characterized by a unique combination of varying-sized peaks and hill-like formations and random spatter-like surface features that help promote rapid and/or more thorough osseointegration of the implant 100 with live bone tissue.

Figure 6C:
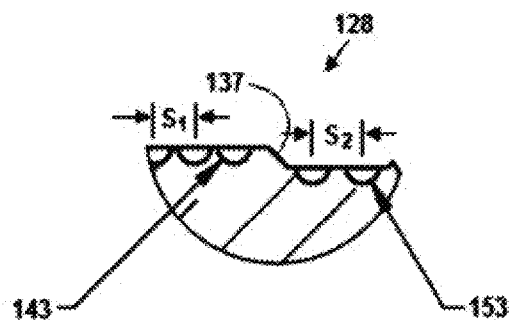
FIG. 6C is a partial sectional view of the upper anchoring portion of the single stage threaded implant of FIG. 6A.

FIGS. 6A and 6B are side plan and longitudinal cross-sectional views, respectively, of a modified embodiment of the single stage threaded implant 100 illustrated and described above in connection with FIGS. 1-5 and having features and advantages of the present invention. FIGS. 6C-H are various detail views of the modified implant of FIGS. 6A and 6B. The threaded implant illustrated in FIGS. 6A-H is similar or identical in design and construction to the implant illustrated and described above in connection with FIGS. 1-5, with the exception of certain features that are described in more detail below. As noted above, preferably the lower anchoring portion 126 is formed with a single continuous clockwise thread 127 that extends helically and/or spirally from the proximal end 126*a* to the distal end 126*b* thereof. Preferably the thread 127 has a pitch of 0.635 mm or about 18% of the major thread diameter Dt at or near the proximal end 126*a* (see, e.g., FIGS. 3A and 6D). The major thread diameter Dt at or near the proximal end 126*a* is preferably about 3.581 mm and is slightly larger (by 0.05 mm or about 1.5%) than the largest diameter D1 of the upper anchoring portion 128. The minor thread diameter at or near the proximal end 126*a* is preferably about 15% smaller than the major thread diameter Dt at or near the proximal end 126*a*. The thread depth is preferably about 0.279 mm or 8% of the major thread diameter Dt at or near the proximal end 126*a*.

Figure 6D:
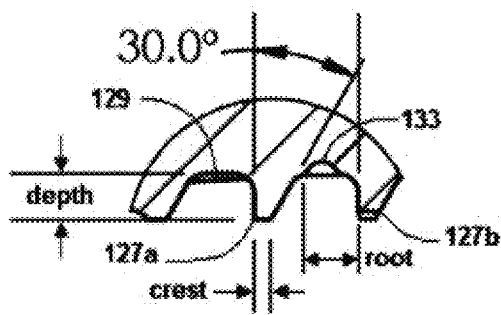
FIG. 6D is a partial sectional view of the lower anchoring portion of the single stage threaded implant of FIG. 6A.

The preferred thread profile is a truncated 30° saw tooth shape having a substantially square gripping edge formed with neutral rake angle (i.e., orthogonal) relative to the pull-out direction of the implant 100, as illustrated in more detail in FIG. 6D. The root or spacing between adjacent threads is preferably 0.318 mm or about 50% of the thread pitch. A flattened crest is preferably formed at the outer-most edge of the thread 127 and preferably has a width of 0.102 mm or about 16% of the thread pitch at the proximal end 126*a* gradually widening to about 0.22 mm or about 35% of the thread pitch at or near the distal end 126*b*. Preferably, the thread pitch and the saw tooth profile remain substantially constant from the proximal end 126*a* to the distal end 126*b*. Preferably the thread profile and thread depth remain substantially constant from the proximal end 126a to an inflexion point 126c located approximately two-fifths of the distance from the proximal end 126a to the distal end 126b, as illustrated in FIG. 6A. From the inflexion point 126c to the distal end 126b preferably the thread depth decreases at a substantially constant rate, reducing from 0.279 mm or about 8% of the major thread diameter at or near the inflexion point 126c to less than 0.04 mm or about 1% of the major thread diameter at or near the distal end 126b, as best illustrated in FIG. 6B.

Figure 6E:
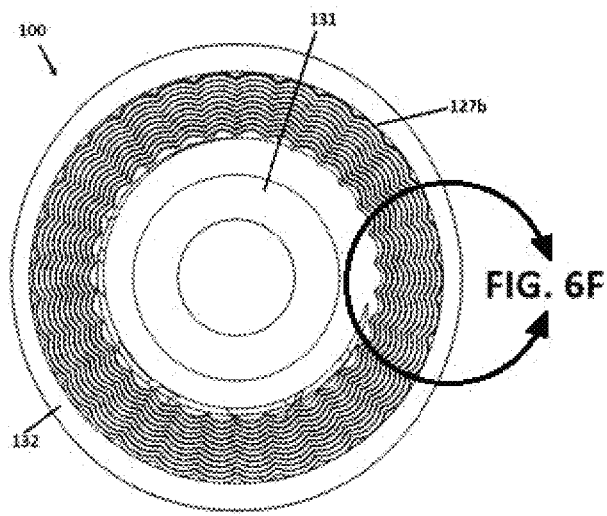
FIG. 6E is a bottom plan view of the single stage threaded implant of FIG. 6A as viewed from the distal end thereof.
Figure 6F:
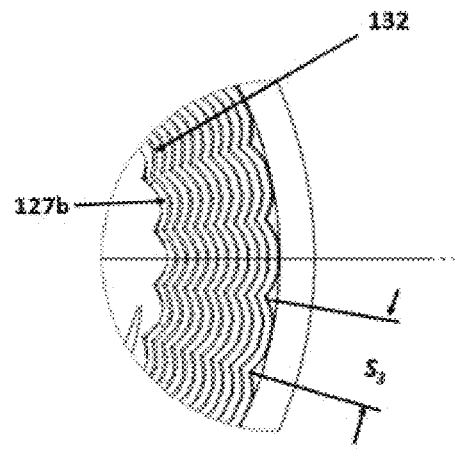
FIG. 6F is a partial sectional view of the single stage threaded implant of FIG. 6E.
Figure 6G:
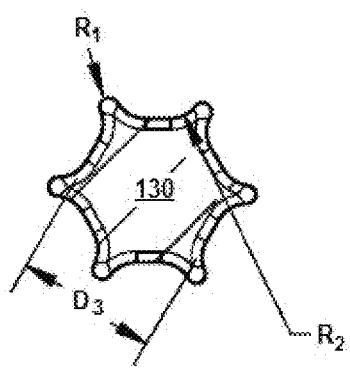
FIG. 6G is a transverse cross-sectional view of the supragingival portion of the single stage threaded implant of FIG. 6A.
Figure 6H:
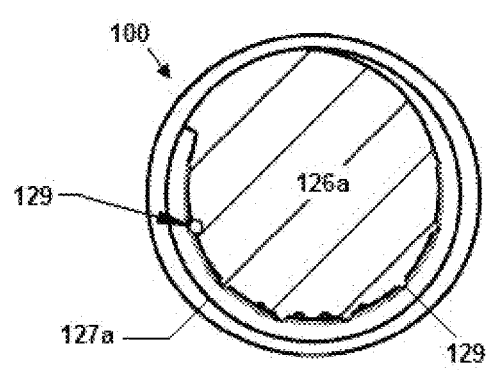
FIG. 6H is a transverse cross-sectional view of the lower and upper anchoring portion of the single stage threaded implant of FIG. 6A as viewed from the proximal end of the lower anchoring portion.

The thread 127 is preferably continuous for the first 2-3 thread revolutions 127a starting from the proximal end 126a and then transitioning to a notched or serrated thread 127b for the remaining portions thereof to the distal end 126b. Preferably, the thread 127 is notched with V-notches 132, as best illustrated in FIGS. 6E and 6F, which are preferably substantially equally radially spaced with a radial spacing S3 of about 11.25°. Alternatively, the V-notches 132 may be equally linearly spaced along the thread path or variably spaced, as desired. If desired, the shape of the V-notches may be varied gradually and/or discretely so as to provide, for example, more aggressive cutting or scraping action (e.g. less-negative rake angles and/or more oblique cutting angles) at or near the distal end 126b of the lower anchoring portion 126 and/or between the distal end 126B and the inflexion point 126c so as to provide a self-tapping and/or self-drilling capability. For example, saw-tooth-like cutting edges may be formed in the thread 127b between the distal end 126b and the inflexion point 126c so as to provide a self-tapping capability wherein mating threads are cut into the surrounding bone tissue as the implant 100 is threaded into an unthreaded or partially-threaded osteotomy. If desired, the spacing, depth and/or rake angle of the cutting edges may be varied from the distal end 126b to the inflexion point 126c so as to minimize friction and cutting forces and/or maximize fracture resistance. Preferably, any cutting edges formed in thread 127b are substantially evenly spaced along the crest of the thread and increase in depth from the distal end 126b to the inflexion point 126c. Preferably, such cutting edges have associated rake angles that gradually decrease from neutral or slightly positive (e.g., 0° to)5° at the distal end 126b to substantially negative (e.g., −30° to −45°) at or near the inflexion point 126c. If desired, any one or more of the cutting edges may be formed with an oblique rake angle so as to reduce friction and associated cutting forces. Optionally, the cutting edges may be formed with alternating positive and negative rake angles and/or alternating oblique rake angles, as desired.

Multiple tie rods 129 are preferably provided between each adjacent thread 127 in a regular spaced pattern. Tie rods 129 are preferably raised surface features which are directly molded, machined or otherwise integrally formed with the lower anchoring portion 126 of the implant body between adjacent threads 127, as illustrated in more detail in FIGS. 6D and 6H. In the particular embodiment illustrated in FIGS. 6A-H the tie rods 129 are arranged in a staggered pattern around the lower anchoring portion 126 forming a clockwise helical sweep path from the proximal end 126a to the distal end 126b thereof, as best illustrated in FIG. 6A. Preferably, starting with at least the second thread revolution from the proximal end an alternating combination of tie rods 129 and round dimples 133 are provided in a regular spaced pattern between adjacent threads 127, as best illustrated in FIGS. 6A and 6D. This pattern preferably continues and repeats along a portion of the remaining thread 127 until it reaches several revolutions after the inflexion point 126c. Preferably, the tie rods 129 and dimples 133 are formed with a maximum height or depth relative to the implant surface of less than about 0.15 mm or about 4% of the local diameter of the implant 100 and, more preferably, less than about 0.05 mm or about 1% of the local diameter of the implant 100. Preferably, the tie rods 129 have a height of about 0.15 mm, a width of about 0.3 mm and a length of about 0.32 mm. Dimples 133 preferably have an average diameter of about 0.130 mm and an average depth of about 0.065 mm.

The upper anchoring portion 128 is generally formed as a stepped cylinder having a first portion 128a configured to engage the hardest/densest part of the cortical bone near the surface thereof, and a second portion 128b configured to engage the less hard/dense part of the cortical bone located 1-2 mm below the surface thereof and/or the transition region between the cortical bone and the softer cancellous bone. The upper anchoring portion 128 is preferably about 1.5 mm to 2 mm in total length, and wherein the first portion 128a comprises about three-fourths and the second portion 128b comprises about one-fourth of this total length. Preferably, the first portion 128a has a first diameter D1 that is about 4% to 5% larger than the second diameter D2 of the second portion 128b. The stepped transition 137 between the first and second portions 128a, 128b (see, e.g., FIG. 6C) preferably forms a 45° chamfer. Optionally, the stepped transition 137 may be coated or impregnated with a temporary bonding or sealing agent and/or an antibacterial coating such as silver ions or the like.

Preferably, the outer bone-engaging surface of the first portion 128a is densely covered with 8 circumferential rows of hemispherical dimples 143 having a radius of 0.064 mm and arranged in a square or hexagonal packing pattern with a center-to-center spacing S1 of 0.152 mm (see FIG. 6C). The outer bone-engaging surface of the second portion 128b is densely covered with 2 circumferential rows of hemispherical dimples 153 having a radius of 0.064 mm and arranged in a square or hexagonal packing pattern with a center-to-center spacing S2 of 0.191 mm. Alternatively, the size and/or depth of the dimples 143 may be varied in a regular or irregular (e.g., random) pattern, if desired, so as to provide an improved bone-engaging surface that increases mechanical engagement and promotes in-growth and adhesion of live bone tissue. Optionally, some or all of the dimples 143, 153 may be replaced with raised bumps, studs, spurs, spikes, knurling and/or similar raised surface features for providing enhanced gripping, frictional anisotropy, resistance to rotation and/or additional desired bone engagement and increased primary stability. If present, these raised features create limited localized residual stresses at the point where each bump or other raised surface feature presses into the surrounding hard cortical bone tissue 160.

For example, 5% to 50% and, more preferably, about 15% of the dimples 143 and/or 153 may be replaced with small bumps that protrude less than about 0.03 to 0.10 mm and, more preferably, about 0.065 mm from the bone-engaging surface 128a into the surrounding hard cortical bone tissue. These bumps and/or similar raised surface features may be arranged in a regular or irregular (e.g., random) pattern and/or they may be arranged, for example, in a helical pattern matching that of the thread 127, if desired. Alternatively, an alternating pattern of round dimples and raised spikes may be provided in a regular or irregular spaced pattern in order to provide precisely controlled amounts of mechanical engagement with the hard cortical bone tissue. Advantageously, the combination of these raised and/or sunken surface features produce precisely controllable amounts of localized stress and stress relief distributed over one or more desired areas of the implant site, resulting in increased mechanical engagement and interlocking of the implant 100 with the surrounding hard bone tissue and improved primary stability, while reducing or limiting the possibility of stress-induced bone necrosis and other bone injuries. Of course, those skilled in the art will readily appreciate that a wide variety of similar raised and/or sunken surface features may be provided in various shapes, sizes, combinations and patterns in order to achieve these and similar advantages as described herein.

As illustrated in FIGS. 6A and 6B the abutment portion 120 of the implant 100 preferably comprises a smoothly tapered transgingival portion 123 configured to emerge from the anchoring portion 110 through the gingiva in a desired emergence profile, and a supragingival portion 130 comprising a post-like structure configured to extend into the oral cavity to receive and support a prosthetic tooth or other restorative structure such as an anatomically-functional aesthetic porcelain crown. Preferably, the transgingival portion 123 has a smooth biologically inert surface that provides a good sealing interface with the surrounding soft gum tissues and prevents or resists the accumulation of plaque and calculus thereon. A suitably smooth surface may be formed, for example, by molding, machining and/or polishing. If desired, the transgingival portion 123 may be molded, shaped and/or contoured in accordance with any number of tooth emergence profiles as may be desired. Suitable emergence profiles may include, for example, simple rotationally symmetric shapes (e.g., round or conical), bilaterally symmetric shapes (e.g., ovular), radially symmetric shapes (e.g., triangular or hexagonal), compound curves, complex curves, or other arbitrary or asymmetric shapes (e.g., shapes mimicking or approximating the emergence profile of a natural tooth being replaced). In one embodiment, a suitable emergence profile is formed as an outwardly-opening flattened or ovular-shaped truncated cone that is substantially circular at the narrower end and substantially ovular at the wider end (see, e.g., FIG. 11B). The distal edge 124 of the transgingival portion 123 may also be contoured or shaped as desired. For example, the buccal and lingual sides of the transgingival portion 123 may be shaved down or undercut, as illustrated in FIG. 6A, in order to more closely follow the crescent-shaped gum lines of a natural tooth being replaced.

As with the other embodiments described above, the supragingival portion 130 of the implant 100 preferably comprises a tapered post 130 having a hex or star-like cross-section (e.g., FIG. 6G) configured to extend into the oral cavity to receive and support a porcelain crown or other restorative device or structure. Preferably, a tapered post having a smoothly-curved 6-star cross section is provided. The post 130 preferably has a minor diameter D3 at its widest point (closest to the transgingival portion 123) of about 2.1 mm, tapering to about 1.75 mm at its narrowest point (furthest from the transgingival portion 123). The points of the star preferably have an external radius R1 of between about 0.12 mm and 0.28 mm and a transition radius R2 of between about 0.23 mm and 0.40 mm. Preferably, a torque driver or similar tool is provided with a similarly-configured 6-star female socket configured to matingly engage and apply a desired (preferably limited) amount of torque to the supragingival portion 130 so as to drive the threaded implant 100 into an osteotomy to a final desired depth (see, e.g., FIGS. 12A-E and the accompanying discussion herein).

FIGS. 7A and 7B illustrate several additional alternative embodiments of a threaded implant design having features and advantages of the invention as illustrated and described above in connection with FIGS. 1-6. In the FIG. 7A embodiment the outer bone-engaging surface of the lower cylindrical portion 128b is further configured with a knurled bone-gripping surface having a raised diamond pattern, as illustrated. Optionally, the lower cylindrical portion 128b may be further coated or impregnated with a temporary bonding or sealing agent and/or an antibacterial coating such as silver ions, silver-decorated carbon nanotubes, or the like. In the FIG. 7B embodiment the outer bone-engaging surface of the lower cylindrical portion 128b is preferably configured with three rows of dimples in a similar configuration to the dimples 153 illustrated and described in connection with FIGS. 6A and 6C. The outer bone-engaging surface of the upper cylindrical portion 128a in the FIG. 7B embodiment is preferably formed with two parallel serrated threads 157a and 157b, as illustrated, each having substantially the same pitch and notched crest configuration as the thread 127b illustrated and described above in connection with FIGS. 3A, 6A, and 6E-F. All of these and similar features may be directly molded, machined or otherwise integrally formed with the upper anchoring portion 128 of the implant 100, as desired or expedient.

Those skilled in the art will appreciate that a wide variety of similar raised and/or sunken surface features and combinations of surface features may be provided or formed on one or more bone-engaging surfaces of a threaded or unthreaded implant in accordance with one or more alternative embodiments of the present invention. These surface features may be provided, for example, on the crest or other bone-engaging portions of one or more threads 127, 157, between adjacent threads 127, on the upper anchoring portion 128, and/or on the lower anchoring portion 126 of a threaded or unthreaded implant. Preferably, these and/or other similar raised or sunken features are formed with a maximum height or depth relative to the implant surface of less than about 0.15 mm or about 4% of the local diameter of the implant. In an alternative embodiment, these and/or other similar raised and/or sunken features are formed with a maximum height or depth relative to the implant surface equal to or less than about 0.05 mm or about 1% of the local diameter of the implant. Advantageously, the combination of these and/or similar raised and/or sunken surface features, such as dimples, bumps and ridges, increases mechanical engagement of the implant and promotes in-growth and adhesion of live bone tissue, thereby improving primary stability and promoting long-term healing and osseointegration.

Some of these surface features may also provide desired gripping, abrading, scraping or cutting action. Yet other surface features may help remove, transport or accommodate bone and other tissue debris that may be formed during insertion of the implant into a threaded or unthreaded osteotomy. Some or all of these surface features may be frictionally isotropic (e.g., see FIG. 8A discussed in more detail below) or frictionally anisotropic (e.g., see FIG. 8B discussed in more detail below), as desired. Those skilled in the art will appreciate that frictionally anisotropic surface features have different frictional properties depending upon the direction in which two surfaces are urged to slide past one another. Frictionally anisotropic surfaces are widespread in nature, ranging from the molecular level to the macroscopic level. For example, the crystal structure of certain solids leads to the anisotropy of their surfaces on an atomic level. Another example of an anisotropic surface is snake skin which is used to produce locomotion by virtue of stiff overlapping scales that are uniformly oriented in the direction of forward sliding motion. Frictional anisotropy can also be produced naturally and/or artificially by employing various anisotropic surface textures and/or surface features, some of which are illustrated and described herein.

For purposes of practicing the claimed invention, frictionally anisotropic surfaces preferably have a directionally-dependent coefficient of sliding friction that is at least 10% less, more preferably at least 25% less, and most preferably at least 50% less, in one direction (e.g., the insertion direction) than in another direction (e.g., the extraction direction). Such frictionally anisotropic surfaces are particularly preferred where it is desired to: i) minimize the insertion force or torque required to drive an implant, ii) maximize the retention or extraction force or torque required to remove an implant, and/or iii) impart desired locomotion to the implant during insertion or extraction thereof (e.g., urging a threaded or unthreaded implant deeper into an osteotomy as it is wiggled, vibrated and/or rotated). Note that for a threaded implant, the "insertion" direction generally refers to clockwise rotation of the implant (assuming a right-handed thread) while the "extraction" direction generally refers to counter-clockwise rotation. For a press-fit implant (described in more detail later) the "insertion" direction generally refers to the pressing-in direction while the "extraction" direction generally refers to the pulling-out direction.

FIGS. 8A and 8B illustrate a number of possible isotropic and anisotropic surface features that may be provided or formed on one or more bone-engaging surfaces of a threaded or unthreaded implant in accordance with one or more alternative embodiments of the present invention. For example, FIG. 8A schematically illustrates the cross-section profile of: (i) a dimpled surface having uniformly sized and spaced dimples, (ii) a stippled surface having uniformly sized and spaced bumps, (iii) a knurled surface having alternating V-shaped grooves, (iv) a friction-enhancing surface having uniformly sized and spaced spikes or studs, (v) a friction-enhancing surface having alternating bumps and spikes, (vi) a textured surface having smoothly undulating sinusoidal wavelets, (vii) a textured surface having alternating bumps and dimples, and (viii) a textured surface having alternating spikes and dimples. FIG. 8B schematically illustrates the cross-section profile of: (i) an anisotropic gripping surface having negatively-raked gripping edges, (ii) an anisotropic gripping surface having neutrally-raked gripping edges, (iii) an anisotropic gripping surface having positively-raked gripping edges, (iv) an anisotropic gripping surface having neutrally-raked gripping edges and rounded leading edges, (v) an anisotropic gripping surface having neutrally-raked gripping edges with alternating flat and rounded leading edges, (vi) an isotropic gripping surface having alternating negatively-raked gripping edges, (vii) an isotropic gripping surface having alternating neutrally-raked and negatively-raked gripping edges and interposed rounded dimples or grooves, (viii) an isotropic gripping surface having alternating positively-raked and negatively-raked gripping edges and interposed rounded dimples or grooves, and (ix) an isotropic gripping surface having alternating neutrally-raked and negatively-raked gripping edges and rounded leading and trailing edges. In each of the cases described above, the various surface features may be formed as discrete localized features or shapes (e.g., radially symmetric dimples, bumps, spikes, studs, spurs, and the like), elongated or irregular features or shapes (e.g., ovals, triangles, rectangles, or the like), or as continuous edges, ridges or grooves that extend from one location to another (e.g., notches formed across a thread). For ease of illustration and explanation, some of the surface features shown and described above are illustrated and/or described as being arranged in a square packing configuration. Of course, those skilled in the art will recognize that a variety of other packing configurations may be used with efficacy, including hexagonal and others as described herein.

Preferably, all of the described geometries and surface features illustrated and discussed above in connection with FIGS. 1-8 are achieved through molding and sintering of the implant 100 (e.g., by spark plasma sintering of yttrium-stabilized zirconia, discussed later) without subsequent machining steps. Alternatively, some or all of the described geometries and/or surface features may be formed by subsequent machining, grinding, etching and/or other fabrication techniques.

Two Stage Threaded Implant

In each of the single-stage threaded implant designs described above, preferably, the subgingival anchoring portion 110 and the supragingival abutment portion 120 are formed as a single integrated structure 100, as will be described in more detail herein. However, in an alternative embodiment the implant 100 may be formed in two or more mating pieces so as to provide greater restorative flexibility. For example, separate mating pieces may be formed as a threaded portion 126, a non-threaded portion 128, a subgingival portion 110, a transgingival portion 123 and/or a supragingival portion 120. Those skilled in the art will appreciate that any two or more of these mating pieces and combinations thereof may be permanently and/or removably secured to one another either before, during or after use in one or more surgical procedures. This may be accomplished, for example, using one or more mating screws or fasteners, or using a suitable cement or bonding agent such as zinc phosphate or polycarboxylate.

FIGS. 9A, 9B, 9C and 9D are a side plan, detail, exploded assembly, and longitudinal cross-sectional views, respectively, of one embodiment of a two stage threaded implant 200 having features and advantages of the present invention. The implant 200 generally comprises an anchoring portion 210 configured to extend subgingivally into an osteotomy formed within the alveolar bone (either the maxilla or the mandible), and a separately-formed ceramic abutment 220 configured to matingly interlock with the anchoring portion 210. The anchoring portion preferably comprises an outer ceramic shell 261 and an inner sleeve 263 formed from a suitably strong material such as titanium or stainless steel. The inner sleeve 263 preferably includes at least one anti-rotational feature 265, such as a hex- or star- or multi-lobe-shaped section, which interlocks with a similarly-configured female socket 267 formed within the outer shell 261. Preferably, a torque driver or similar tool (see, e.g., FIGS. 12A-12E and the accompanying discussion herein) is also provided and includes a similarly-configured male bit (e.g., hex, square, star, multi-lobed and/or the like) configured to matingly engage the socket 267 and to apply a desired amount of torque sufficient to drive the anchoring portion 210 into an osteotomy to a final desired depth. The inner sleeve 263 is preferably threaded on both ends so as to receive a sleeve retention screw 269, for securing and retaining the sleeve 263, and an abutment retention screw 271, for securing and retaining the abutment 220.

Preferably, the abutment 220 and the outer shell 261 of the anchoring portion 210 are formed from a suitable ceramic material such as yttrium-stabilized zirconia which is preferably densely sintered and molded to a final desired geometry, as will be described in more detail later. Alternatively, the abutment 220 and the outer shell 261 may be formed as densely sintered ceramic blanks which are molded to near-final geometry and then machined to their final desired geometry by grinding and/or other machining steps. Alternatively, one or both of the abutment 220 and the outer shell 261 may be formed from blanks of pure titanium, titanium alloy, or other suitable material by molding, casting, rolling, forging, grinding and/or other machining operations.

Referring again to FIG. 9A, the anchoring portion 210 of the implant 200 generally comprises a soft-bone-engaging lower anchoring portion 226 and a hard-bone-engaging upper anchoring portion 228. The lower anchoring portion 226 comprises a generally tapered round or cylinder-like body extending from a proximal end 226a (nearest the oral cavity) to a distal end 226b (furthest from the oral cavity). One or more threads 227 are provided and are configured to engage the soft cancellous bone tissue. The tapered body is preferably widest at the proximal end and smallest at the distal end and may have a constant or variable (e.g., accelerating or decelerating) rate of taper from the proximal to the distal end. In one embodiment the distal end 226b of the lower anchoring portion 226 may be 20% to 60% smaller in diameter than the proximal end 226a. In another embodiment the distal end 226b may be 38% smaller in diameter than the proximal end 226a. Preferably, the taper rate accelerates from approximately 0 mm/mm) (0°) at the proximal end 226a to approximately 0.1625 mm/mm)(4.6°) at the distal end 226b. In alternative embodiments, the taper rate may vary from approximately 0 mm/mm)(0°) to approximately 0.36 mm/mm)(10°) and may accelerate, decelerate, or remain constant along the length thereof. In various embodiments the lower anchoring portion 226 may have a diameter ranging from 2.5 mm to 7.5 mm and a length ranging from 3 mm to 12 mm, as desired or expedient. Of course, a wide variety of geometrically similar implant designs formed in various shapes, sizes and dimensions are possible and desirable according to the particular clinical indication and the particular needs and desires of the patient. The distal end 226b of the implant 200 is capped by sleeve retention screw 269 which is preferably suitably sized and configured to tightly seal against the outer shell 261. Optionally, one or more O-rings and/or other sealing structures (not shown) may be provided, as desired or expedient.

Preferably, the lower anchoring portion 226 is formed with a single continuous clockwise thread 227 that extends helically and/or spirally from the proximal end 226a to the distal end 226b thereof. Preferably the thread 227 has a pitch of between about 0.4 mm to 0.8 mm or about 15%-25% of the major thread diameter Dt at or near the proximal end 226a and, more preferably, about 18% of the major thread diameter at or near the proximal end 226a (see FIG. 9B). The minor thread diameter at or near the proximal end 226a is preferably 10%-20% smaller and, more preferably, about 15% smaller than the major thread diameter at or near the proximal end 226a. The thread depth is preferably about 5-10% of the major thread diameter at or near the proximal end 226a and, more preferably, about 8% of the major thread diameter at or near the proximal end 226a.

The preferred thread profile is a truncated 30° saw tooth shape having a neutral or slightly positive rake angle. The root or spacing between adjacent threads is preferably about 40%-60% of the thread pitch and, more preferably, about 50% of the thread pitch. A flattened crest is preferably formed at the outer-most edge of the thread 227 and preferably has a width of 0.102 mm or about 16% of the thread pitch at the proximal end 226a gradually widening to about 0.22 mm or about 35% of the thread pitch at or near the distal end 226b. Preferably, the thread pitch and the saw tooth profile remain substantially constant from the proximal end 226a to the distal end 226b. Preferably the thread profile and thread depth remain substantially constant from the proximal end 226a to an inflexion point 226c located approximately one-third of the distance from the proximal end 226a to the distal end 226b. From the inflexion point 226c to the distal end 226b preferably the thread depth decreases at a constant and/or accelerating rate, reducing from about 8% of the major thread diameter at or near the inflexion point 226c to less than about 1-2% of the major thread diameter at or near the distal end 226b.

Optionally, the thread 227 may be notched or serrated along at least a portion of its length, as illustrated in FIG. 9A. If desired, one or more cutting edges may also be formed or provided on the thread 227 at or near the distal end 226b of the lower anchoring portion 226 and/or between the distal end 226B and the inflexion point 226c so as to provide a self-tapping and/or self-drilling capability. Preferably, sawtooth-like cutting edges are formed in the thread 227 between the distal end 226B and the inflexion point 226c so as to provide a self-tapping capability wherein mating threads are cut into the surrounding bone tissue as the implant 200 is threaded into an unthreaded or partially-threaded osteotomy. If desired, the spacing, depth and/or rake angle of the cutting edges may be varied from the distal end 226b to the inflexion point 226c so as to minimize friction and cutting forces and/or maximize fracture resistance. Preferably, any cutting edges formed in thread 227 are substantially evenly spaced along the crest of the thread and increase in depth from the distal end 226b to the inflexion point 226c. Preferably, such cutting edges have associated rake angles that gradually decrease from neutral or slightly positive (e.g., 0° to 5°) at the distal end 226b to substantially negative (e.g., −30° to −45°)0 at or near the inflexion point 226c. If desired, any one or more of the cutting edges may be formed with an oblique rake angle so as to reduce friction and associated cutting forces. Optionally, the cutting edges may be formed with alternating positive and negative rake angles and/or alternating oblique rake angles, as desired.

As described above in connection with FIGS. 1-7, multiple tie rods 229 are preferably provided between each adjacent thread 227 in a regular or irregular spaced pattern. Tie rods 229 are preferably raised surface features which are directly molded into the outer ceramic shell 261 between adjacent threads 227. In the particular preferred embodiment illustrated in FIGS. 9A-D the tie rods 229 are arranged in a staggered pattern around the lower anchoring portion 226 forming a clockwise helical sweep path from the proximal end 226a to the distal end 226b thereof, as best illustrated in FIG. 9A. Other raised or sunken surface features may also be provided on various bone-engaging surfaces of the implant 200 as desired or expedient, such as for example and without limitation, in the form of dimples, bumps or ridges. Any or all of these optional surface features may be provided in various shapes, sizes, combinations and arrangements, as desired, such as illustrated and described in connection with FIGS. 8A and 8B. For example, an alternating combination of tie rods 229 and round dimples 233 may be provided in a regular spaced pattern between adjacent threads 227, as illustrated in FIGS. 9A and 9B. This pattern may repeat or continue along the entire thread 227 as it winds from the proximal to the distal end and/or it may repeat or continue along only one or more portions of the thread 227, as illustrated in FIG. 9A. Alternatively, the size, shape, combination and/or arrangement of such surface features may be varied along the path of the thread 227, as desired, so as to provide a variety of bone-engaging surface features.

Preferably, these and/or other similar raised or sunken features are formed with a maximum height or depth relative to the implant surface of less than about 0.15 mm or about 4% of the local diameter of the implant 200. In an alternative embodiment, these and/or other similar raised and/or sunken features are formed with a maximum height or depth relative to the implant surface equal to or less than about 0.05 mm or about 1% of the local diameter of the implant 200. Preferably, the tie rods 229 have a height of about 0.15 mm, a width of about 0.3 mm and a length of about 0.32 mm. Dimples 233 preferably have an average diameter of about 0.130 mm and an average depth of about 0.065 mm. Alternatively, the size and/or depth of the dimples 233 may be varied in a regular or irregular (e.g., random) pattern, if desired, so as to provide a surface that promotes mechanical engagement, adhesion and in-growth of live bone tissue. Alternatively, some or all of the dimples 233 may be replaced with similarly-sized bumps or alternating and/or varying combinations of dimples, bumps and/or other similar surface features as desired.

The upper anchoring portion 228 is designed to engage the hard/dense cortical bone in a manner that optimally achieves both primary stability and long-term osseointegration. The upper anchoring portion 228 is preferably formed as an inverted truncated cone having an emergence profile that preferably substantially matches the emergence profile of the transgingival portion 223 of the abutment 220, as illustrated in FIGS. 9A and 9D. Optionally, the outer bone-engaging surface of the upper anchoring portion 228 may be densely covered with multiple raised and/or sunken surface features (not shown), such as dimples, bumps or ridges, arranged in a regular or irregular spaced pattern. These raised and/or sunken surface features are preferably directly molded, machined or otherwise integrally formed with the upper anchoring portion 228 of the outer shell 261 and have a packing density of greater than about 0.65, more preferably greater than about 0.75, and most preferably greater than about 0.85. Preferably, these and/or other similar raised and/or sunken features are formed with a maximum height or depth relative to the implant surface equal to or less than about 0.15 mm or about 4% of the local diameter of the implant 200. In an alternative embodiment, these and/or other similar raised and/or sunken features are formed with a maximum height or depth relative to the implant surface equal to or less than about 0.05 mm or about 1% of the local diameter of the implant 200.

The abutment 220 preferably comprises a smoothly tapered transgingival portion 223 configured to emerge from the anchoring portion 210 through the gingiva in a desired emergence profile, and a supragingival portion 230 comprising a post-like structure configured to extend into the oral cavity to receive and support a prosthetic tooth or other restorative structure such as an anatomically-functional aesthetic porcelain crown. Preferably, the transgingival portion 223 has a machined or polished biologically inert surface that provides a good sealing interface with the surrounding soft gum tissues and prevents or resists the accumulation of plaque and calculus thereon. If desired, the transgingival portion 223 may be shaped and contoured in accordance with any number of tooth emergence profiles as may be desired. Suitable emergence profiles may include, for example, simple rotationally symmetric shapes (e.g., round or conical), bilaterally symmetric shapes (e.g., ovular), radially symmetric shapes (e.g., triangular or hexagonal), compound curves, complex curves, or other arbitrary or asymmetric shapes (e.g., shapes mimicking or approximating the emergence profile of a natural tooth being replaced). In one embodiment, a suitable emergence profile is formed as an outwardly-opening flattened or ovular-shaped truncated cone that is substantially circular at the narrower end and substantially ovular at the wider end (see, e.g., FIG. 11B). The supragingival portion 230 preferably comprises a tapered anti-rotational cross-section configured to extend into the oral cavity to receive and support a porcelain crown or other restorative device or structure. This may be bonded or cemented directly to the supragingival portion 230 using a suitable bonding agent such as zinc phosphate or polycarboxylate.

Figure 10C:
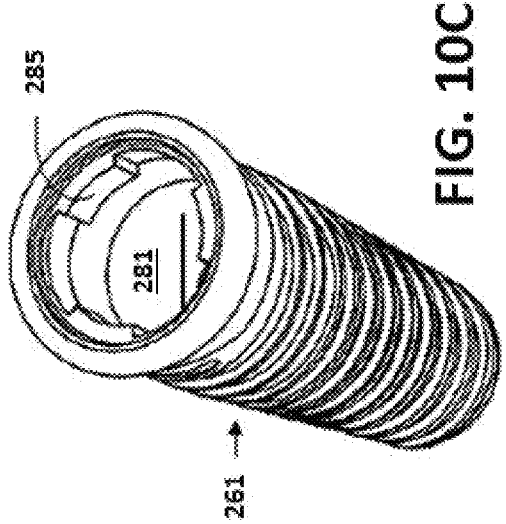
FIG. 10C is an isometric view of the outer shell portion of the implant anchoring portion of FIG. 10A.
Figure 10D:
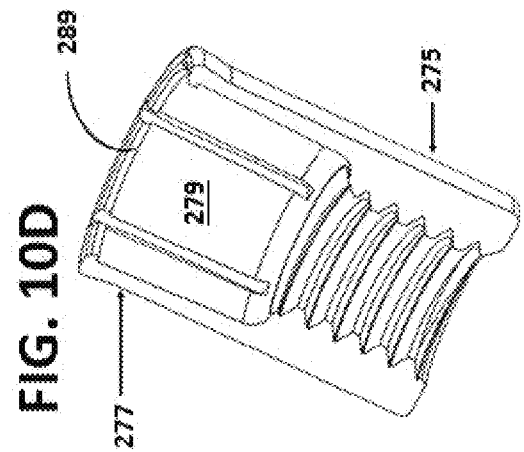
FIG. 10D is a longitudinal cross-sectional view of the inner sleeve portion of the implant anchoring portion of FIG. 10A.
Figure 10B:
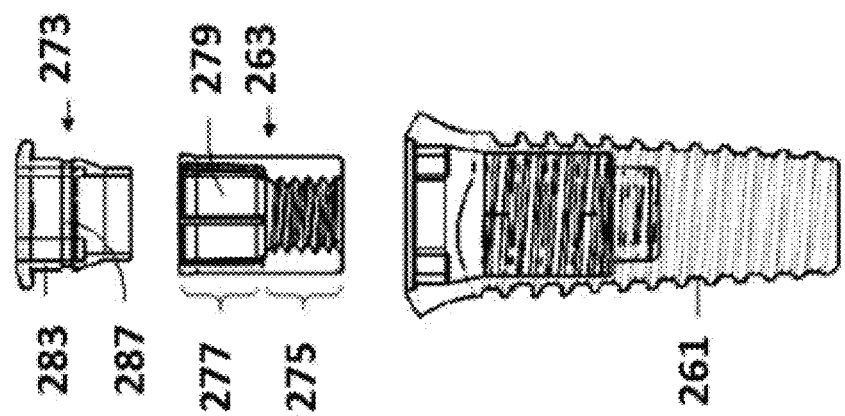
FIG. 10B is an exploded assembly view of the implant anchoring portion of FIG. 10A shown in partial cross section.
Figure 10A:
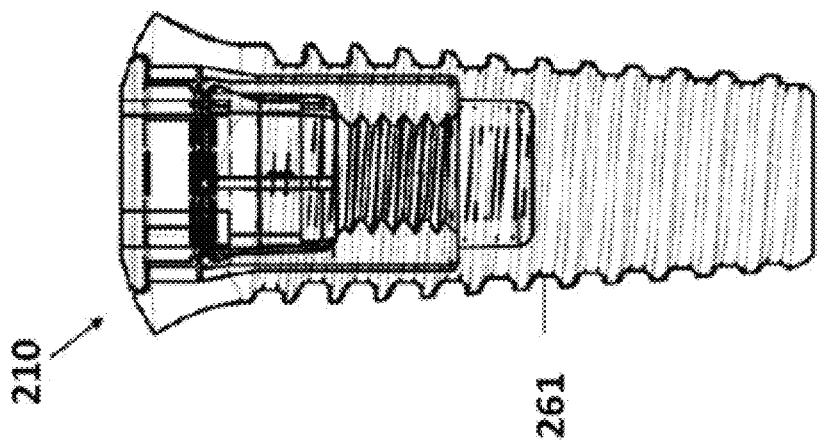
FIG. 10A is a side plan view of an alternative embodiment of the implant anchoring portion of a two stage threaded implant having features and advantages in accordance with the present invention.
Figure 10E:
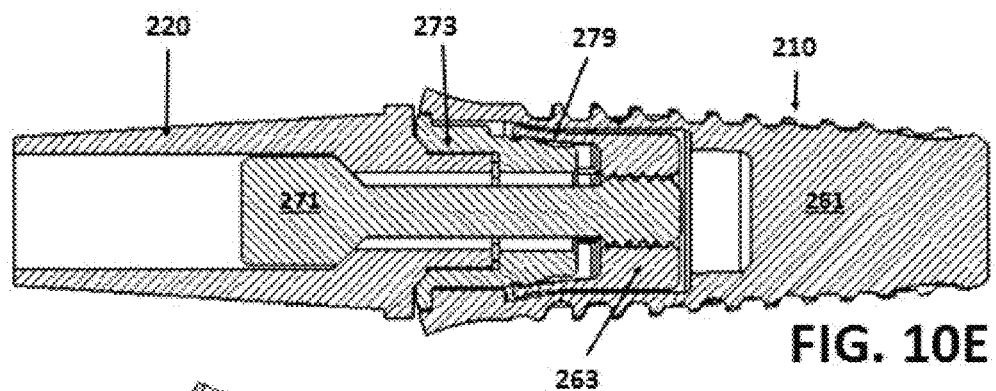
FIG. 10E is a longitudinal cross-sectional view of the two stage threaded implant of FIG. 10A with an attached abutment.
Figure 10F:
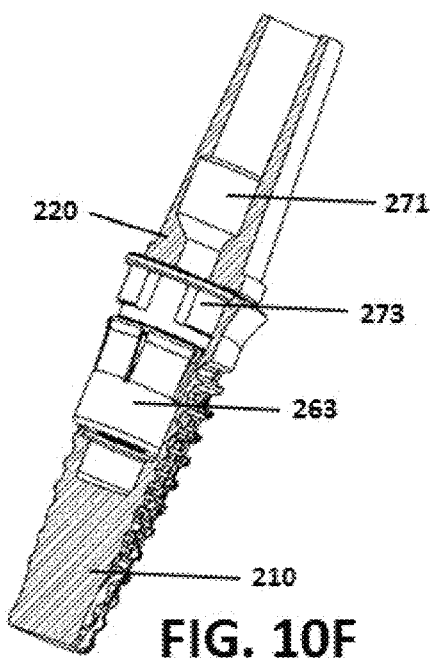
FIG. 10F is a side plan view of the two stage threaded implant and attached abutment of FIG. 10E.
Figure 10G:
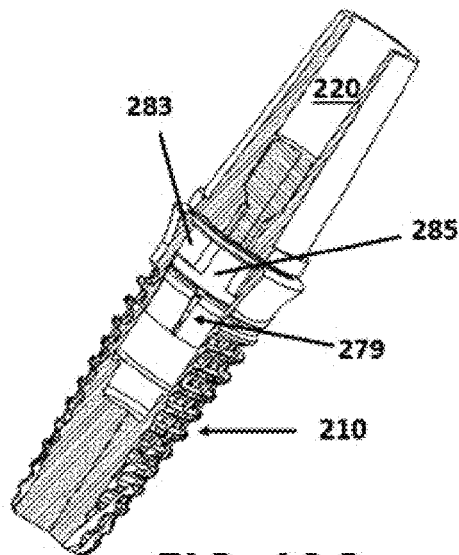
FIG. 10G is a side plan detail view of the two stage threaded implant and attached abutment of FIG. 10E.

FIGS. 10A and 10B are a side plan and exploded assembly views, respectively, of an alternative embodiment of the anchoring portion 210 illustrated and described in connection with FIGS. 9A-D which eliminates the need for the sleeve retention screw 269. The anchoring portion 210 illustrated in FIGS. 10A-I is similar or identical in design and construction to the anchoring portion 210 illustrated and described above in connection with FIGS. 9A-D, with the exception of certain features that are described in more detail below. As illustrated in FIGS. 10A-I the modified anchoring portion 210 generally comprises an outer shell 261 (e.g., FIGS. 10C, 10H) formed from a ceramic material, and lower and upper inner sleeves 263, 273 formed from a suitably strong material having a high spring constant such as titanium or stainless steel (e.g., FIGS. 10B, 10D, 10E, 10H). The lower inner sleeve 263 includes a lower threaded portion 275 for receiving the threaded end of abutment retention screw 271 (e.g., FIGS. 10E, 10F) and an upper portion 277 having multiple flexible retention fingers 279. The lower inner sleeve 263 is designed to slip into a mating cylindrical cavity 281 formed in the top of the outer ceramic shell 261 (e.g., FIGS. 10C, 10E).

Figure 10H:
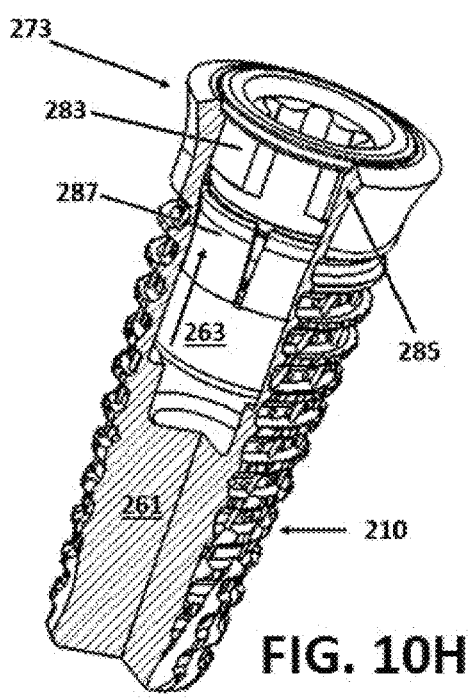
FIG. 10H is an isometric view of the two stage threaded implant FIG. 10A from a side perspective with the outer ceramic shell shown in partial cross section.
Figure 10I:
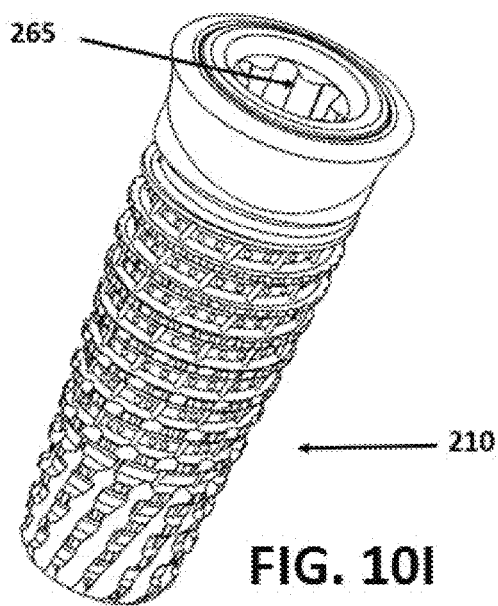
FIG. 10I is an isometric view of the two stage threaded implant FIG. 10A from a top perspective.

Once the lower inner sleeve 263 is in place within the inner cavity 281 of the outer shell 261, the upper inner sleeve 273 is pressed in through the opening 281 and engages the flexible fingers 279 of the lower sleeve 263. When the retention screw 271 is inserted and tightened, the lower sleeve 263 is pulled upward toward the upper sleeve 273 causing the flexible fingers 279 to ride up the sloped surface of the upper sleeve 273 and resiliently expand as illustrated in FIG. 10H. An annular groove 287 is preferably provided in the upper sleeve 273 (e.g., FIG. 10E, 10H) configured to receive mating snaps 289 provided on the flexible fingers 279 (e.g., FIG. 10D) of the lower sleeve 263. Once the retention screw is fully tightened, the flexible fingers tightly contract and the snaps 289 matingly engage with the annular groove 287 pulling the upper sleeve 273 downward against the outer shell 261 with a desired sealing force and providing secure retention between the upper sleeve 273 and the lower sleeve 263. Preferably, this secure retention and downward sealing force is maintained even if the retention screw 271 becomes loosened and/or is subsequently removed.

Preferably, torque-transmitting anti-rotational features 283 are provided on the upper sleeve 273 (e.g., FIGS. 10*h*, 10H) and engage corresponding anti-rotational lobes 285 provided within the interior opening 281 of the outer shell 261 (FIG. 10C) so that driving torque may be transmitted from the upper sleeve 273 directly to the outer ceramic shell 261. Alternatively, and/or in addition, one or more anti-rotational features (not shown) may be provided between one or more of the sleeves 263, 273 and the outer shell 261 so that driving torque may also (or instead) be transmitted from the inner sleeves 263, 273 to the outer shell 261. The upper sleeve 273 also preferably includes at least one anti-rotational feature 265, such as a hex- or star- or multi-lobed-shaped section (e.g., FIG. 10I), which is configured to interlock with a similarly-configured mating abutment and/ or the male bit of a torque driver or similar tool (see, e.g., FIGS. 12A-12E) for driving the anchoring portion 210 into an osteotomy.

Single Stage Press-Fit Implant

FIGS. 11A and 11B are partial side plan and top plan views, respectively, of one embodiment of a single stage press-fit implant 300 having features and advantages of the present invention. The press-fit implant 300 may have a diameter ranging from about 2.5 mm to 7.5 mm and a length ranging from about 3 mm to 12 mm, as desired or expedient. Preferably the entire implant 300 is formed from a suitable ceramic material such as yttrium-stabilized zirconia which is molded and densely sintered to a final desired geometry, as will be described in more detail herein. Alternatively, the implant 300 may be formed as a densely sintered ceramic blank which is then machined to a final desired geometry by grinding and/or other machining steps. Alternatively, the implant 300 may be formed from a blank of pure titanium, titanium alloy, or other suitable material by molding, casting, rolling, forging, grinding and/or other machining operations. Alternatively, the implant 300 may be formed in two or more mating pieces configured to be permanently and/or removably secured to one another either before, during or after use in one or more surgical procedures. This may be accomplished, for example, using one or more mating screws or fasteners, and/or using a suitable cement or bonding agent such as zinc phosphate or polycarboxylate.

As illustrated in FIG. 11A, the implant 300 generally comprises an anchoring portion 310 configured to extend subgingivally into an osteotomy formed within the alveolar bone (either the maxilla or the mandible), and an abutment portion 320 connected to and preferably integrally-formed with the anchoring portion 310 and configured to extend through the gingiva 150 into the oral cavity to support a prosthetic tooth 140 or other structure(s) desired to be secured (see, e.g., FIG. 2). The implant 300 is configured to be surgically inserted into an unthreaded osteotomy formed within the alveolar bone of a patient, which typically consists of both hard/dense cortical bone and relatively soft/spongy cancellous bone. The abutment portion 320 preferably comprises a smoothly tapered transgingival portion 323 configured to emerge from the anchoring portion 310 through the gingiva in a desired emergence profile, and a supragingival portion 330 comprising a post-like structure configured to extend into the oral cavity to receive and support a prosthetic tooth or other restorative structure such as an anatomically-functional aesthetic porcelain crown.

The angle of emergence and the particular emergence profile of the abutment portion 320 relative to the anchoring portion 310 may be varied, as desired, such as illustrated in FIGS. 11B and 11C, in order to address a wide variety of clinical needs using a single surgical implant system. Most preferably, the implant 300 is packaged and/or provided as part of a surgical implant system that includes multiple implants 300 having similar geometries (e.g., similar or identical anchoring portions 310), but with varying abutment emergence angles, emergence profiles, implant surface features, and the like, such as illustrated in FIG. 11C. Optionally, a system of similarly-configured implant analogues 350 may also be provided, such as illustrated in FIG. 11D, in order to enable a surgeon to check the fit, depth, emergence angle, emergence profile and/or desired angular orientation of the final implant selection using a similarly-configured implant analogue 350. Preferably, the anchoring portion of each corresponding implant analogue 350 is slightly undersized (e.g., by 1% to 2%) and has a smooth and/or polished surface so as to facilitate easy insertion and removal from an osteotomy. Implant analogues 350 may be formed from ceramic, titanium, stainless steel, or other suitable materials, as desired or expedient.

Preferably, the transgingival portion 323 of the implant 300 has smooth biologically inert surface that provides a good sealing interface with the surrounding soft gum tissues and prevents or resists the accumulation of plaque and calculus thereon. A suitably smooth surface may be formed, for example, by molding, machining and/or polishing. The transgingival portion 323 is also preferably molded, shaped and/or contoured in accordance with any number of tooth emergence profiles as may be desired. Suitable emergence profiles may include, for example, simple rotationally symmetric shapes (e.g., round or conical), bilaterally symmetric shapes (e.g., ovular), radially symmetric shapes (e.g., triangular or hexagonal), compound curves, complex curves, or other arbitrary or asymmetric shapes (e.g., shapes mimicking or approximating the emergence profile of a natural tooth being replaced). In one embodiment, a suitable emergence profile is formed as an outwardly-opening flattened or ovular-shaped truncated cone that is substantially circular at the narrower end and substantially ovular at the wider end. The outer edge 324 of the transgingival portion 323 may also be contoured or shaped as desired. For example, the buccal and lingual sides of the transgingival portion 323 may be shaved down or undercut, as illustrated in FIG. 11A (see also FIG. 1), in order to more closely follow the crescent-shaped gum lines of a natural tooth being replaced. In another embodiment, the emergence profile of the transgingival portion 323 is formed or shaped based on a mold or CT scan of the natural tooth being replaced and/or a sculpted analogue closely matching the tooth socket of the removed tooth.

The supragingival portion 330 preferably comprises a post-like structure having a tapered anti-rotational cross-section (e.g., hex, square, star, and/or the like) configured to extend into the oral cavity to receive and support a porcelain crown or other restorative device or structure. The crown or other restorative device may be bonded or cemented directly to the supragingival portion 330 using a suitable bonding agent such as zinc phosphate or polycarboxylate. Preferably, a torque driver or similar tool (see, e.g., FIGS. 12A-E and the accompanying discussion) is provided with a similarly-configured female socket (e.g., hex, square, star, multi-lobed and/or the like) configured to matingly engage and apply a desired amount of torque to the supragingival portion 330 to help press and rotate and/or wiggle the implant 300 back and forth while maneuvering it into an unthreaded osteotomy to a final desired depth and angular orientation. Optionally, a small mallet and/or a specially configured surgical impact driver or vibration driver may be used to vibrate, tap, rotate and/or drive the implant 300 into an unthreaded osteotomy to a final desired depth and angular orientation without overstressing the implant or causing undue patient discomfort.

The anchoring portion 310 generally comprises a soft-bone-engaging lower anchoring portion 326 and a hard-bone-engaging upper anchoring portion 328. The lower anchoring portion 326 comprises a generally round or cylinder-like body, as illustrated, which may either be tapered or untapered, as desired. Preferably, the lower anchoring portion 326 is untapered or only slightly tapered (e.g., less than 1° or 2°) along all or a selected portion of its length from the proximal end (closest to the oral cavity) to the distal end thereof (furthest from the oral cavity). If tapered, the lower anchoring portion 326 is preferably widest at the proximal end and smallest at the distal end and may have a constant or variable (e.g., accelerating or decelerating) rate of taper from the proximal to the distal end. In one embodiment the lower anchoring portion 326 may be 5% to 10% smaller in diameter at the distal end than at the proximal end thereof. If desired, the distal end of the implant may terminate in a single-reducing or double-reducing chamfer 331, as illustrated in FIG. 11C. If desired, one or more cutting edges (not shown) may be formed or provided at or near the distal end of the lower anchoring portion 326 so as to provide a self-drilling or self-reaming capability.

Preferably, the outer bone-engaging surface of the lower anchoring portion 326 is densely covered with multiple raised and/or sunken surface features, such as dimples, bumps or ridges, arranged in a regular or irregular spaced pattern. See, for example, FIGS. 8A and 8B and the accompanying discussion. These raised and/or sunken surface features are preferably directly molded or otherwise integrally formed with the lower anchoring portion 326 of the implant 300 and have a packing density of greater than about 0.65, more preferably greater than about 0.85, and most preferably greater than about 0.90. In the particular preferred embodiment illustrated in FIG. 11A a plurality of similarly-sized dimples are arranged in a square-packed lattice pattern and have a packing density of about 0.75. Alternatively, other suitable packing configuration(s) may be employed, such as disclosed herein. However, square or hexagonal lattice packing configurations are particularly preferred.

Preferably, these and/or other similar raised and/or sunken features are formed with a maximum height or depth relative to the implant surface equal to or less than about 0.15 mm or about 4% of the local diameter of the implant 300. In an alternative embodiment, these and/or other similar raised and/or sunken features are formed with a maximum height or depth relative to the implant surface equal to or less than about 0.05 mm or about 1% of the local diameter of the implant 300. However, some larger features may also be used, as desired. Advantageously, the combination of these and other raised and/or sunken surface features, such as dimples, bumps and ridges, increases mechanical engagement of the implant and encourages in-growth and adhesion of live bone tissue, thereby improving primary stability and promoting healing and osseointegration of the implant 300. Dimples preferably have an average diameter of about 0.130 mm, an average depth of about 0.065 mm and are preferably spaced apart between 0.13 mm and 0.18 mm from center to center and, more preferably about 0.15 mm from center to center, in a square packing or hexagonal packing arrangement. Alternatively, the size and/or depth of the dimples may be varied in a regular or irregular (e.g., random) pattern, if desired, so as to provide an improved bone-engaging surface that increases mechanical engagement and promotes in-growth and adhesion of live bone tissue. Optionally, some or all of the dimples may be replaced with raised bumps, studs, spurs, spikes, knurling and/or similar raised surface features for providing enhanced gripping, frictional anisotropy, resistance to rotation and/or additional desired bone engagement and increased primary stability. If present, these raised features create limited localized residual stresses at the point where each bump or other raised surface feature presses into the surrounding soft cancellous bone tissue 170 (see FIG. 2).

For example, 25% to 75% and, more preferably, about 50% of the dimples may be replaced with small bumps that protrude less than about 0.03 to 0.10 mm and, more preferably, less than about 0.065 mm from the bone-engaging surface 326 into the surrounding soft cancellous bone tissue. These bumps and/or similar raised surface features may be arranged in a regular or irregular (e.g., random) pattern, as desired. Alternatively, an alternating pattern of round dimples and raised spikes may be provided in a regular or irregular spaced pattern in order to provide precisely controlled amounts of mechanical engagement with the soft cancellous bone tissue. Advantageously, the combination of these raised and/or sunken surface features produce precisely controllable amounts of localized stress and stress relief distributed over one or more desired areas of the implant site, resulting in increased mechanical engagement and interlocking of the implant 300 within the surrounding bone tissue and improved primary stability, while reducing or limiting the possibility of stress-induced bone necrosis and/or other bone injuries. Of course, those skilled in the art will readily appreciate that a wide variety of similar raised and/or sunken finely detailed surface features may be provided in various shapes, sizes, combinations and patterns in order to achieve these and similar advantages as described herein.

Alternatively, or in addition, larger raised features, such as large bumps (e.g., having diameters greater than about 0.25 mm), gripping edges, thread-like features, and/or the like, may be added in order to provide additional desired functionality. For example, hemispherical bumps 333 having a diameter between 0.25 mm to 0.5 mm may be arranged on the lower anchoring portion 326, as illustrated in the alternative embodiment shown in FIG. 11C(v). These may be uniform in size and spacing, as shown, or they may be varied in size and/or spacing along the length of the lower anchoring portion 326, as desired. In another possible alternative embodiment, scalloped gripping edges 335 are provided, as illustrated in FIG. 11C(ii). Preferably, the gripping edges 335 are formed in an upward arc or scallop, as shown, so as to provide frictional anisotropy relative to the insertion (pressing-in) direction of the implant 300. Those skilled in the art will appreciate that wiggling or rotating the implant 300b of FIG. 11C(ii) back and forth (i.e., alternately torqueing it clockwise and counterclockwise) creates small amounts of locomotion in the insertion direction which helps move the implant 300b deeper into an unthreaded osteotomy. In this manner, the insertion depth and angular orientation of the implant 300b can be precisely controlled and/or adjusted by the surgeon.

In another possible alternative embodiment illustrated in FIG. 11C(iii) one or more isotropic or anisotropic raised surface features are arranged in an helical pattern H1 and configured so as to help drive the implant 300c into an unthreaded osteotomy as it is rotated clockwise (in the case of a right-handed helix) or counterclockwise (in the case of a left-handed helix). In another possible alternative embodiment illustrated in FIG. 11C(iv), a first plurality of raised surface features are provided arranged in a right-handed helix pattern H1 and a second plurality of raised surface features are provided arranged in a left-handed helix pattern H2. The surface features may comprise, for example, anisotropic gripping edges formed along and aligned with each helix pattern H1 and H2 configured to produce small amounts of locomotion in the insertion direction when the implant 300d is wiggled or rotated back and forth (i.e., alternately torqued clockwise and counterclockwise). Again, in this manner, the insertion depth and angular orientation of the implant 300d can be precisely controlled and/or adjusted by the surgeon.

Referring again to FIG. 11A the upper anchoring portion 328 is designed to engage the hard/dense cortical bone 160 (e.g., see FIG. 2) in a manner that optimally achieves both primary stability and long-term osseointegration. Preferably, the upper anchoring portion 328 is generally formed as a cylinder having diameter that is about 3% to 8% larger than the diameter if the lower anchoring portion 326 and, more preferably, about 4% to 5% larger. The stepped transition 337 between the upper and lower anchoring portions 328, 326 may be square, chamfered or curved, as desired or expedient. Optionally, the stepped transition 337 may include one or more downward-facing cutting edges or teeth (not shown) configured and arranged to cut, abrade or expand a slightly-undersized osteotomy (e.g., an osteotomy that is undersized by about 3% to 8%). Optionally, the stepped transition 337 may be coated or impregnated with a temporary bonding or sealing agent and/or an antibacterial coating such as silver ions or the like. The outer bone-engaging surface of the upper anchoring portion 328 is preferably configured with a knurled bone-gripping surface comprising a raised diamond pattern, as illustrated. Preferably this knurled surface is also frictionally anisotropic relative to the insertion direction of the implant 300 such that rotating the implant 300 back and forth generates locomotion in the insertion direction to help move the implant 300 deeper into an unthreaded osteotomy. In this manner, the insertion depth and angular orientation of the implant 300 can be precisely controlled and/or adjusted. Optionally, the upper anchoring portion 328 may be further coated or impregnated with a temporary bonding or sealing agent and/or an antibacterial coating such as silver ions, silver-decorated carbon nanotubes, or the like.

Preferably, all of the described geometries and surface features illustrated and discussed above in connection with FIGS. 11A-D are achieved through molding and sintering of the implant 300 (e.g., by spark plasma sintering of yttrium-stabilized zirconia, discussed later) without subsequent machining steps. Alternatively, some or all of the described geometries and/or surface features may be formed by subsequent machining, grinding, etching and/or other fabrication techniques well known to those skilled in the art.

Clinical Techniques and Tools

In the clinical procedure for inserting each of the implant embodiments described above, an oral surgeon first prepares the implant site by exposing and forming an osteotomy within the alveolar bone (either the maxilla or the mandible) of a patient. The size, shape, depth and orientation of the osteotomy is carefully planned using X-ray imaging and/or CT scanning of the patient's teeth, mouth and surrounding tissues to ensure there is sufficient bone integrity, thickness and depth to accommodate the implant. If the available bone structure is insufficient to support the implant, various bone grafting techniques may be used to augment, build up and/or repair the target implant site. A drill guide is preferably used to ensure the precise location and desired orientation of the osteotomy. Progress may be confirmed using X-ray imaging and/or CT scanning as the procedure progresses.

Once the osteotomy is formed to a desired depth a reamer and/or other similar tools may be used to expand and/or more precisely shape the opening of the osteotomy in accordance with a desired bone emergence profile of a particular implant selected to be inserted. For example, a dual-diameter stepped cylindrical reamer may be used to precisely shape the opening of the osteotomy to match the stepped cylindrical profile of the upper anchoring portion 128 of the threaded implant 100 illustrated and described above in connection with FIGS. 1-7. A conical or flared reamer may be used to precisely shape the opening of the osteotomy to match the flared emergence profile of the upper anchoring portion 228 of the two stage implant 200 illustrated and described above in connection the FIGS. 9 and 10. A single-diameter cylindrical reamer may be used to precisely shape the opening of the osteotomy to match the cylindrical profile of the upper anchoring portion 328 of the press-fit implant 300 illustrated and described above in connection the FIGS. 11A-D. In each case, the appropriately-shaped reamer preferably includes a smooth cylindrical guide portion that extends into the previously-formed osteotomy to ensure precise alignment of the tool with the osteotomy. One or more additional reamers or similar shaping tools may optionally be used to further hone, expand and/or shape the osteotomy, as needed or desired, to accommodate a tapered implant such as threaded implant 100, 200. In the case of a threaded implant, preferably a bone tap is used to cut threads into the surrounding bone tissue to a desired depth. Preferably, the bone tap is shaped and configured to form female threads that matingly engage with the male threads formed on the outer bone-engaging surface of the threaded implant.

Once the osteotomy is formed and suitably shaped and/or threaded, a precision torque driver is preferably used to drive or maneuver the implant to its final seated position. The torque driver is preferably configured to limit the amount of insertion torque to no more than the maximum design torque threshold for the particular associated implant (up to about 45 N-cm for a titanium implant and about 15-30 N-cm for a Zirconia implant). If the torque required to seat the implant exceeds the design threshold, the surgeon must remove the implant and use one or more of the above-described tools (e.g., drills, reamers, taps) to clean and/or enlarge the osteotomy. The torque driver and/or any one or more of the other tools described herein may be packaged and sold with the implant as a sterile single-use implant surgical kit, or the tools may be packaged and sold separately from the implant, as desired or expedient.

Figure 12A:
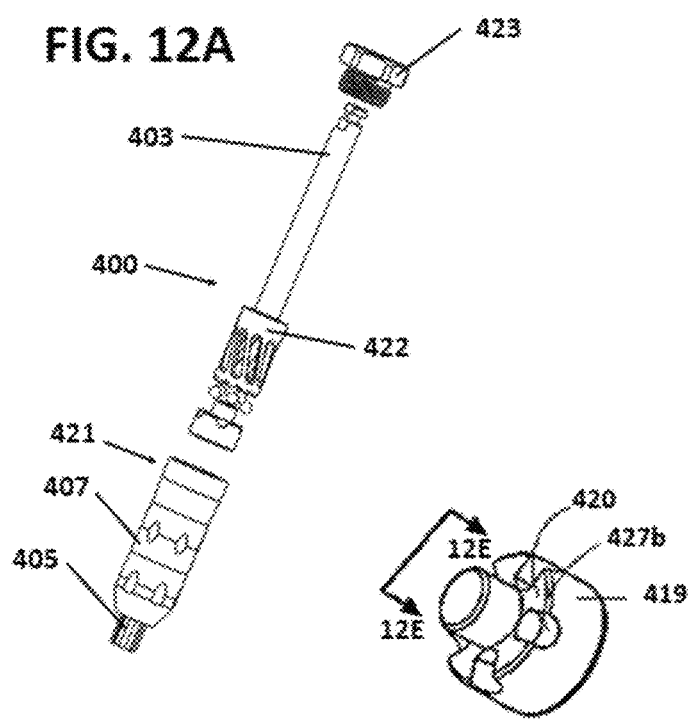
FIG. 12A is an exploded assembly view an implant torque driver having features and advantages in accordance with the present invention.
Figure 12C:
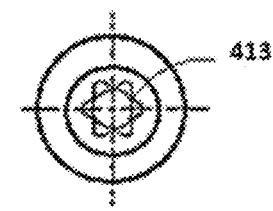
FIG. 12C is a bottom plan view of the implant torque driver of FIG. 12A.

FIGS. 12A-E illustrate one possible embodiment of a precision torque driver 400 configured for driving a threaded or unthreaded ceramic implant and having features and advantages in accordance with the present invention. As illustrated in FIG. 12A the torque driver essentially comprises an input drive shaft 403, an output drive shaft 405, and a torque-limiting transfer coupling 407. The input drive shaft 403 is configured to be coupled to a motorized driver (not shown) or a manually-manipulated T-handle (not shown) through a conventional shaft coupling. The output shaft 405 is formed as an implant-engaging male or female driver bit having a mating anti-rotational cross-section such as a square, hex, star, multi-lobed 413. Optionally, one or more intermediate output drive shaft components (not shown) may be used to engage and drive other mating male and/or female components, as desired.

The torque-limiting transfer coupling 407 comprises multiple (preferably 5) ball bearings 415 (e.g., stainless steel or ceramic bearings) that are generally configured to roll within a bearing race formed between a first component comprising a flexible cage 417 which forms an upper race 418 and a second component comprising a bearing support 419 forming a lower race 420. Alternatively, other rolling or sliding bearing types may be used with efficacy, including spherical-, cylindrical-, needle-, tapered-, barrel-, or slip-type bearings. The flexible cage 417 generally comprises a hollow cylinder having an upper portion 417*a*, a lower portion 417*b* and a middle portion 417*c* having a plurality of flexible fingers 422. The fingers 422 may be straight or slanted, as desired, or expedient. Preferably the fingers 422 are slanted or twisted by 5° to 10° as illustrated. Those skilled in the art will appreciate that at least the upper portion 417*a* of the flexible cage is rigidly coupled to the input shaft 403 while the second component 419 forming the lower race 420 is rigidly coupled to the output shaft 405. The flexible cage 417 and the second component 419 are both mounted within a housing comprising a main enclosure 421 and a threaded cap 423 which threads onto the end of the main enclosure 421. Those skilled in the art will appreciate that the housing may be fixed relative to the output shaft 405 and the second component 419, or it may be fixed relative to the input shaft 403 and the flexible cage 417, as desired or expedient.

Figures 12D, 12E:
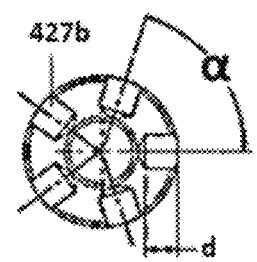
FIG. 12D is an isometric view of the lower bearing support component of the implant torque driver of FIG. 12A.
FIG. 12E is a top plan view of the lower bearing support component of FIG. 12D.
Figure 12B:
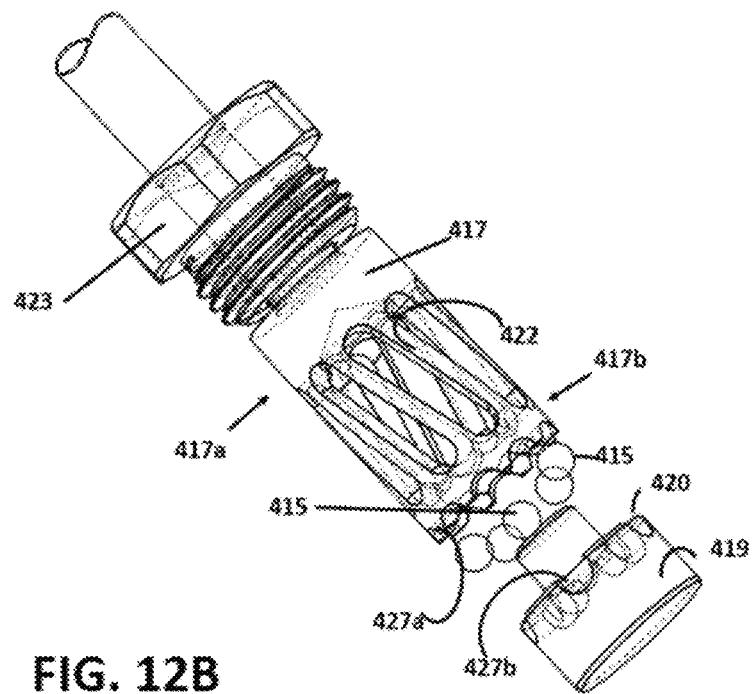
FIG. 12B is a detail exploded assembly view of the implant torque driver of FIG. 12A.

When the torque-limiting transfer coupling 407 is assembled as illustrated in FIG. 12A, the flexible cage 417 presses the upper race 418 against the bearings 415 which press against the lower race 420. The precise amount of force applied will be dictated by the effective spring constant of the flexible fingers 422 and the amount of preload or compression applied. These parameters can be varied or adjusted as desired. The upper race 418 and/or the lower race 420 is preferably formed with one or more grooves, undulations, dimples and/or detents 427a, 427b that allow the bearings 415 to be seated or partially seated at various angular displacements a (preferably in 72° increments) along the bearing race, as best illustrated in FIGS. 12B, 12D and 12E. Those skilled in the art will appreciate that when the bearings 415 are seated within their respective detents 427a and 427b further clockwise rotation of the input shaft 403 relative to the output shaft 405 will cause the flexible cage 417 to twist and axially contract as the bearings 415 unseat and advance to the next detent location. The threshold input torque required to fully unseat the bearings 415 is the maximum torque that can be transmitted by the torque driver 400. However, counter-clockwise rotation of the input shaft 403 relative to the output shaft 405 will cause the flexible cage 417 to twist in the opposite direction causing it to axially expand (as the flexible fingers 422 try to straighten out), preventing the bearings 415 from unseating from their respective detents 427a, 427b and effectively locking the input shaft 403 to the output shaft 405. In this manner, the insertion torque of the torque driver 400 is limited according the maximum design threshold, but the extraction torque is not limited. In an alternative design, the maximum extraction torque may be limited to the same, higher or lower threshold as the insertion torque. This may be achieved, for example, by varying the twist angle and/or flex characteristics of the flexible fingers 422.

Implant Fabrication

Conventional titanium implants are typically individually machined from a solid cylinder of titanium material and then acid etched to produce a finished implant having the final desired geometry and surface texture. The machining and acid etching (or other surface treatment) processes introduce oils, chemicals and other impurities to the surface of the work piece which must be removed by extensive post-fabrication cleaning and sterilization. Conventional titanium implant fabrication is also slow, requiring several days or even weeks to complete a single finished implant. It is also highly capital intensive, typically requiring multiple six-axis grinding machines and other sophisticated production equipment.

Conventional ceramic implants are typically fabricated in a similar fashion by grinding green-stage blanks to an initial desired geometry (e.g., forming threads and other macro features), sintering in an oven for several hours and then further grinding, sandblasting or acid etching the resulting hard smooth surface of the sintered implant to produce a finished implant having the final desired geometry and surface texture. The green-stage grinding process alone typically leads to production losses of 10-15% due to discoloration, fracturing and chipping. Additional expense and production losses are incurred in the post-sintering machining operations due to the inherent difficulties in machining hard, brittle ceramic materials. It is well known that post-sintering grinding and other ablative machining, sandblasting and chemical etching steps can leave machining marks, micro-cracks, fissures and other defects in the finished ceramic surface that can make the implant more susceptible to cracking or fracturing. See, e.g., Gahlert M, Burtscher D, Grunert I, Kniha H, Steinhauser E., Failure analysis of fractured dental zirconia implants, Clin. Oral Impl. Res. 23, 2012;287-293. As a result of these and other difficulties, ceramic implant fabrication according to conventional methods is expensive, slow and capital intensive, typically requiring multiple six-axis grinding machines and other sophisticated production equipment.

Figure 13:
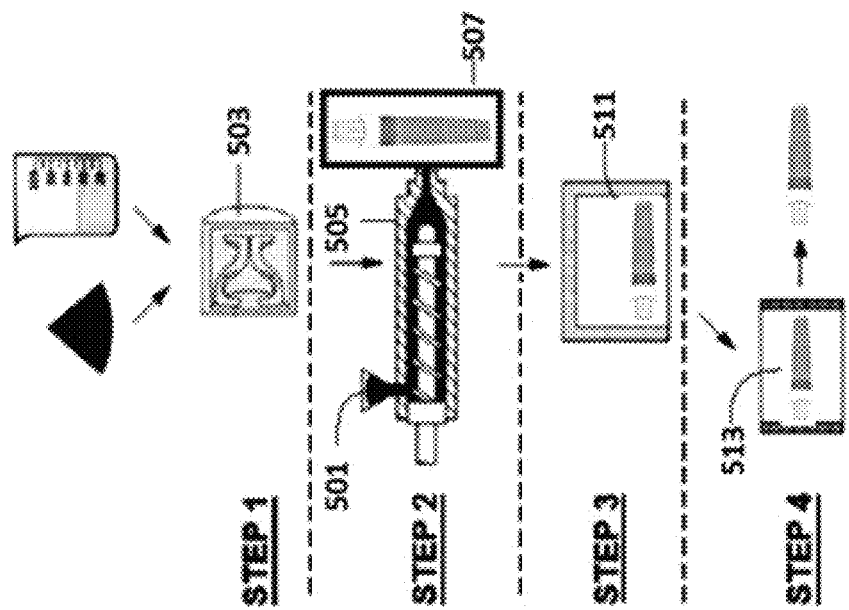
FIG. 13 is a schematic diagram illustrating the process of injection molding, debinding and sintering an implant having features and advantages in accordance with the present invention.

Accordingly, an improved implant fabrication technique is provided, as described in more detail herein, that avoids or mitigates some or all of these problems and which increases manufacturing yields and reduces manufacturing time and expense. In accordance with one embodiment, as schematically illustrated in FIG. 13, an implant is molded in green stage to substantially its final geometry (enlarged to account for shrinkage during subsequent sintering), including substantially all final surface texturing and/or other surface features as disclosed and described herein. For example, the single stage threaded implant 100 may be molded entirely in green stage (e.g., from powdered ceramic or powdered titanium) with finely detailed surface features, such as tie rods 129, serrated thread 127b, dimples 133, 143, and the like. This green stage implant may be debinded and then sintered in one or more sintering operations to produce a finished product that does not require any grinding, machining, sandblasting or etching. Thus, for example, a finished osseointegrative ceramic implant can be reliably and inexpensively fabricated by sintering an injection-molded ceramic (or titanium) green-stage body. Advantageously, the integrity and fracture resistance of the finished product is considerably improved because the crystalline grain pattern of the sintered material follows the geometry and surface features of the mold cavity rather than being formed ablatively by grinding, machining, sandblasting or etching the green-stage body and/or the sintered body.

Referring to FIG. 13, the manufacturing process begins at Step 1. Yttria-stabilized zirconia ("YSZ") powder is mixed in a mixer 503 (e.g., a twin screw kneader) with a suitable binder, such as low density polyethylene, paraffin wax or, more preferably, a water-soluble binder described in more detail below. Those skilled in the art will appreciate that the binder is a temporary vehicle for homogeneously packing the powder particles into the desired shape during injection molding and then holding the particles in shape until the beginning of sintering. The binder system may include multiple components which are preferably selected to provide sufficiently low viscosity for easy filling of the mold cavity during injection molding, high green strength for demolding (i.e., ejection or removal of the green body), as well as good shape retention and low shrinkage during debinding and subsequent sintering.

The dispersibility of powder particles within a binder is highly dependent on the forces between the particles. Accordingly, the use of small organic molecules such as fatty acids offers an attractive inter-particle potential, which dominates the rheological behavior of a suspension. Because particle agglomerates are frequently observed in starting ceramic powders, surfactants such as oleic acid and stearic acid (SA) are preferably added to the mixture to improve powder dispersion during mixing. The main function of such surfactants is to produce a modified powder surface so that steric stabilization between individual particles can be attained in the colloid to help evenly disperse the powder. For example, suitable surface modification of zirconia powder may be achieved by thoroughly ball-milling the YSZ powder with 3.0 vol % stearic acid (SA) before mixing with the binder. See, e.g., Wei Liu,z Zhipeng Xie,w,z Xianfeng Yang,z,y Yin Wu,z Cui Jia,z Tiezhu Bo,z and Linlin Wang, Surface Modification Mechanism of Stearic Acid to Zirconia Powders Induced by Ball Milling for Water-Based Injection Molding, J. Am. Ceram. Soc., 94 [5] 1327-1330 (2011), incorporated herein by reference in its entirety. Advantageously, the resulting SA coating limits the agglomeration of the YSZ powder and changes the nature of the powder surface from hydrophilic to hydrophobic, which decreases the shear viscosity of the feedstock and increases the water-debinding rate.

Preferably, an SA-coated superfine (0.5-10 µm dia.) or ultrafine (≤500 nm dia.) powder of 3 mol % yttria-stabilized zirconia (Y2O3)3 (ZrO2)97 having an average particle size of between 0.05 and 0.25 µm, more preferably about 0.16 µm, and a BET surface area between about 5 and 30 m2/g, more preferably about 8.2 m2/g, is mixed with a water-soluble binder such as polyethylene glycol (PEG) or poly-oxy-methylene (POM) to provide a feedstock injection molding operations. For example, suitable YSZ powders may be obtained from Farmeiya Advanced Materials Co., Ltd., Jiujiang, China, such as grade YSZ-F-DM-3.0. Alternatively, finer-grade YSZ powders may also be used with efficacy, including nano powders having an average particle size between 20 and 50 nm and a BET surface area between 15 and 40 m2/g, such as 3 mol % Y2O3 stabilized ZrO2 nano powder (product #4039ON-9502) available from Inframat Advanced Materials LLC, Manchester, Conn. See, e.g., F. Mohd Foudzi, et al., Yttria stabilized zirconia formed by micro ceramic injection molding: Rheological properties and debinding effects on the sintered part, Ceramics International (2012), http://dx.doi.org/10.1016/j.ceramint. 2012.09.033, incorporated herein by reference in its entirety. Of course, those skilled in the art will appreciate that the fabrication techniques described herein are not limited to YSZ powders, but may be practiced using a wide variety and combination of ceramic and/or non-ceramic powders including, without limitation, zirconia, alumina, silica, porcelain, calcium phosphate β-tricalcium phosphate, hydroxylapatite, bioglass, silicon carbide, tungsten carbide, titanium, titanium oxide, vanadium, thorium, niobium, tantalum, calcium, and the like. However, SA-coated superfine or ultrafine powders comprising YSZ are preferred.

The SA-coated YSZ powder is preferably mixed with a water-soluble binder in sufficient ratio to achieve a solids loading of between 40% and 60% and more preferably about 48%. It has been found that YSZ solids loadings in this range provide sufficiently high green densities for sintering while maintaining good flowability in the injecting phase. The feedstock flow behavior is defined largely by the interactions between particles. During injection molding the particles slide past each other by translation and rotation. Accordingly, YSZ powders comprising spherical or nearly spherical particles are generally preferred as such particles can easily rotate and slip past each other in the feedstock stream. However, some degree of particle shape irregularity is also acceptable and can actually improve particle packing and shape stability during green-stage processing. Easy gliding is also supported by low binder viscosity, good wetting behavior and thorough coating of the powder surface. Preferably, all agglomerates are broken up during the mixing step in order to completely eliminate any enclosed pores and eliminate large irregular shaped compacts that might otherwise increase flow resistance and/or produce defects in the finished product.

Figure 14B:
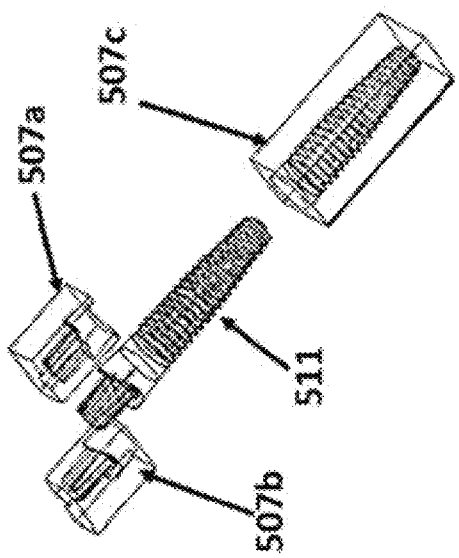
FIGS. 14A and 14B are assembled and exploded views, respectively, of a three-part injection mold used to form a green body of an implant in accordance with the injection molding, debinding and sintering process illustrated in FIG. 13.
Figure 14A:
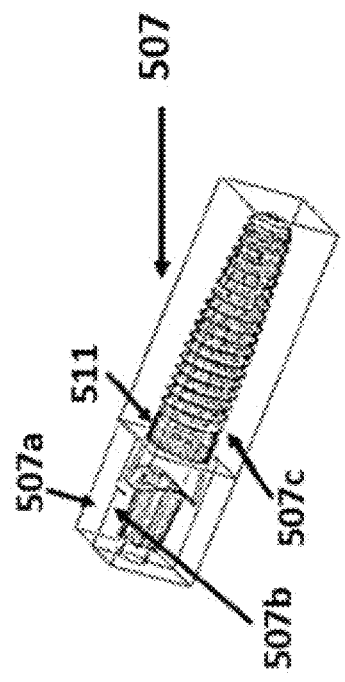

The next step (FIG. 13, Step 2) involves injecting the feedstock 501 into a suitably-constructed mold 507 using an injection molding machine 505. For example, FIG. 14A illustrates a three-part mold 507 that may be used to form a green body of a ceramic implant 100 having all of the final geometries (enlarged to accommodate for subsequent shrinkage) and detailed surface features as described herein. Those skilled in the art will appreciate that the feedstock may be heated (e.g., to 175° C.) and injected under pressure (e.g., 80 MPa) so as to completely fill the mold 507 with the feedstock 501 comprising the above-described mixture of powdered YSZ and binder material. Once the mold cools, the top portions 507a, 507b of the mold are separated into their two halves exposing the top portion of the green body 511 corresponding generally to the abutment portion 128 of the single stage threaded implant 100 illustrated and described above in connection with FIGS. 1-6. The green body 511 is then removed from the lower portion of the mold by rotating the top portion of the green body in a counter-clockwise unscrewing motion. Those skilled in the art will appreciate that the green body 511 shrinks slightly upon cooling making it possible to be easily removed from the lower portion of the mold 507c without damaging the green body. See, e.g., V. Piotter, T. Mueller, K. Plewa, J. Prokop, H.-J. Ritzhaupt-Kleissl, & J. Haussell, Manufacturing of Complex-shaped Ceramic Components by Micropowder Injection Molding, Int. J. Adv. Manuf. Technol. (2010) 46:131-134, incorporated herein by reference in its entirety. Advantageously, this so-called "untwist demolding" enables molding of unique complex features, such as serrated threads, cutting edges, undercut features, and the like, that cannot otherwise be easily attained using a conventional two-part mold. Alternatively, some or all of these unique complex features may be omitted and a traditional two-part mold may be used, if desired.

The next step (FIG. 13, Step 3) involves debinding the green body 511 (i.e., removing all or substantially all of the binder material). Thermal debinding (heating in a kiln or oven and thereby causing the binder to evaporate or burn off) is the traditional method of debinding and is widely used in the ceramic injection molding industry. But this process produces outgassing of pollutants which must be vented and/or otherwise controlled. Also, during thermal debinding considerable care must be taken to avoid excessive pressure build-up from decomposed gases which might otherwise cause cracking, crazing and/or other defects in the finished product. Organic solvent debinding, water debinding, wicking debinding, supercritical debinding and catalytic debinding are examples of other debinding methods that have been developed as improvements, supplements and/or alternatives to thermal debinding. Among these alternatives, water debinding and catalytic debinding are particularly preferred for purposes of carrying out the present invention, as they have advantages of high efficiency, flexibility and environmental friendliness.

Binder systems for water debinding mainly consist of a water-soluble binder which dissolves in water and a water-insoluble backbone binder which keeps the strength of the green body after the water-soluble binder has been removed. During initial water debinding a large fraction (e.g., 85% or more) of the organic binder material is dissolved in water and is extracted, leaving a green body having a generally interconnected porous structure. The remaining fraction of organic binder material is removed in one or more subsequent debinding steps, such as organic solvent debinding, catalytic debinding, thermal debinding, and/or the like. Higher solids loadings and smaller particle sizes generally lead to lower porosity, higher tortuosity of the pores, a lower interdiffusion coefficient and a slower debinding rate. Depending on the binder polymer used, these further debinding steps can be carried out by thermal and/or chemical decomposition. For example, POM-based binders are typically removed by catalytic debinding using concentrated nitric acid at 110° C. See, e.g., U.S. Pat. No. 8,674,018 to Maat et al, incorporated herein by reference in its entirety. Suitable examples of water-soluble binder systems include combinations of: i) acetanilide with polystyrene, ii) polyethylene glycol (PEG) with polymethyl-methacrylate (PMMA), iii) PEG with cellulose acetate butyrate, iv) PEG with polyvinyl butyral (PVB), and v) polyoxymethylene (POM).

Advantageously, the resulting interconnected porous structure evolved through water debinding, thermal debinding and/or catalytic debinding may also be used as a channel to introduce additional elements, compounds or materials through the porous outer surface of the partially debound green body 511 to a particular desired depth (e.g., less than 0.5 mm and preferably less than 0.1 mm). See, e.g., G. W. Liu, Z. P. Xie, W. Wang, Y. Wu and X. F. Yang, Fabrication of coloured zirconia ceramics by infiltrating water debound injection moulded green body, Advances in Applied Ceramics 2011 VOL 110 NO 1, p. 58, incorporated herein by reference in its entirety. These added elements, compounds or materials may be used, for example, to modify the color, translucency, surface texture, surface chemistry, surface hardness, crystallinity, porosity, electrical conductivity, or biological compatibility of the implant surface. For example, the water debound green body 511 may be fully or partially immersed in an aqueous solution containing ions of silver, gold, titanium, and/or other elements or compounds, as desired, so as to cause the ion solution to enter the porous surface of the green body 511 by capillary action and to diffuse interiorly to a desired depth. The depth of penetration can be controlled or adjusted by varying the concentration of the ion solution, temperature, agitation, exposure time, and/or other parameters affecting the duration of exposure or the rate of diffusion. As another example, the water debound green body 511 may be fully or partially immersed in a colloidal solution or fluidized bed comprising nanoparticles of titanium, zirconia, YSZ, α-tricalcium phosphate, hydroxyapatite, carbon, carbon nanotubes (CNT), and/or other particles sufficiently small in size such that at least some of the particles enter and remain lodged in the porous surface of the green body 511 and/or diffuse interiorly to a desired depth. As another example, the water debound green body 511 may be fully or partially exposed to an electric arc discharge, gas plasma, ionized gas, sublimation vapors, air-borne particulates, and/or other particles suspended in a fluid such that at least some of the surface-modifying elements, compounds or materials enter the porous surface of the green body 511 and/or diffuse interiorly to a desired depth.

In any one or more of the above described examples partial surface modification may be achieved by selectively exposing only a portion of the water debound green body 511 (e.g., the anchoring portion or the abutment portion) to the surface-modifying element, compound or material. For example, certain portions of the water debound green body 511 may be selectively dipped in an aqueous ion solution and/or certain portions of the green body 511 may be selectively masked with a masking element or a temporary coating prior to exposing the green body to the surface-modifying element, compound or material. In some embodiments, the surface-modifying element, compound or material itself forms a desired component of the finished post-sintered implant surface. For example, surface infused particles of titanium, zirconia, silica, boron, hydroxyapatite or YSZ may provide a desired surface chemistry, roughness and/or color that improves biological compatibility, osseointegration or aesthetic appeal of the finished implant product. In other embodiments, the surface-modifying element, compound or material is used only as an intermediate component to facilitate further modification of the post-sintered implant surface and/or the green body surface. For example, surface infused ions or particles of silver, gold, carbon or titanium may provide desired electrical conductivity at the surface of the green body 511 and/or the sintered implant in order to facilitate further surface modification through various electro-chemical reactions, electroplating, electric discharge machining (EDM), and/or similar surface modification techniques. In yet other embodiments, the surface-modifying element, compound or material may be extracted, dissolved, or otherwise removed from the post-sintered implant surface (e.g., via water, acid or other solvent, electrochemical reaction, or burning/oxidation) producing, for example, a porous outer YSZ ceramic surface having improved biological compatibility and/or osseointegration characteristics.

The final step (FIG. 13, Step 4) involves sintering and densification of the debound green body 511 into a hard, dense body 513 having the final desired geometry, surface features and dimensions. Sintering is based on atomic diffusion between two or more adjacent contacting particles. The driving force for sintering and densification is the change in free energy from the decrease in surface area and lowering of the surface free energy by the gradual elimination of solid-vapor interfaces between adjacent particles. On a microscopic scale, material transfer is affected by atomic diffusion powered by the difference in free energy across the curved surfaces of each particle. As the size of the particle becomes smaller (and its curvature becomes higher) the resulting decrease in free energy becomes larger.

In a typical sintering process, the debound green body 511 is heated in a kiln or furnace to an elevated temperature (e.g., 300-1500° C.) that is below the melting point of the material. The atoms making up the individual powder particles diffuse across the boundaries of the particles, eventually fusing the particles together forming one solid mass. Advantageously, because the sintering temperature is lower than the melting point of the material, the geometrical shape of the green body 511 can be precisely maintained while the individual powder particles gradually fuse together forming a densely sintered body 513. For example, in one embodiment a green body with finely detailed surface features is formed by injection molding a feedstock comprising ultrafine polycrystalline yttria-stabilized tetragonal zirconia powder (94.4% ZrO2, 5.0-5.3% Y2O3, 0.2-0.3% Al2O3) having an average particle size of between 0.05 and 0.25 μm thoroughly mixed in a water-soluble POM-based binder. After final debinding the debound green body is sintered by heating it from room temperature to 270° C. at a rate of about 3 K/min and holding for 1 hour, then heating it to 1500° C. at a rate of about 3 K/min and holding for 1 hour, then cooling it to 600° C. at a rate of about −5 K/min, followed by furnace cooling for one hour. Following initial sintering, hot isostatic pressing (HIP) is used to close any residual porosity and to gain additional density and strength. Preferably, the sintered body is placed in a pressurized vessel containing Argon gas maintained at a pressure of 150-250 MPa. The sintered body is heated from room temperature to 1350° C. at a rate of about 5 K/min and held for 2 hours, then cooled to 1200° C. at a rate of about 3 K/min and held for 1 hour, and then cooled to room temperature.

During conventional sintering the heat necessary to produce atomic diffusion is usually provided via one or more external heating elements and transferred to the green body 511 in a furnace or kiln via convection and/or infrared radiation. While the green body 511 is heating up, the external heat transfer mechanism (which heats the green body from the outside in) can lead to undesirable thermal gradients, which can result in cracks, shape distortions and/or other defects. To prevent the formation of undesirable thermal gradients during sintering, slow heating rates and/or isothermal holding periods are typically employed. For example, conventional sintering of 3 mol % YSZ is typically limited to a heating rate of only about 7° C. per minute. However, slower heating rates lead to growth of larger crystalline grains which generally results in decreased material properties such as strength, hardness, and toughness. Thus, rapid sintering and densification is generally preferred.

Microwave sintering (MWS) is another sintering method which uses microwaves to heat up a zirconia green body 511. It is well known that the conductivity of zirconia increases with temperature and that zirconia is actually a good electrical conductor at temperatures above 800-850° C. This allows a YSZ green body 511 to be heated from the inside out using microwaves or other electromagnetic fields. Combined with conventional heating mechanisms such as convection and radiation, microwave assisted sintering advantageously allows the green body 511 to be heated at a more rapid rate of 20° C. per minute or more without producing cracks, shape distortions or other defects.

Figure 15A:
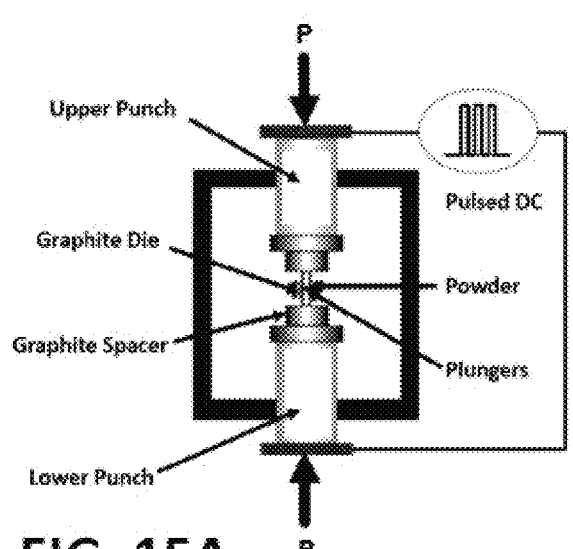
FIGS. 15A, 15B and 16 are schematic diagrams illustrating the process of spark plasma sintering an implant having features and advantages in accordance with the present invention.
Figure 15B:
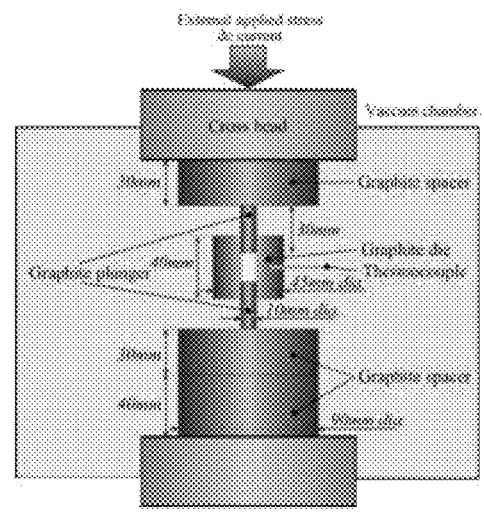
Figure 16:
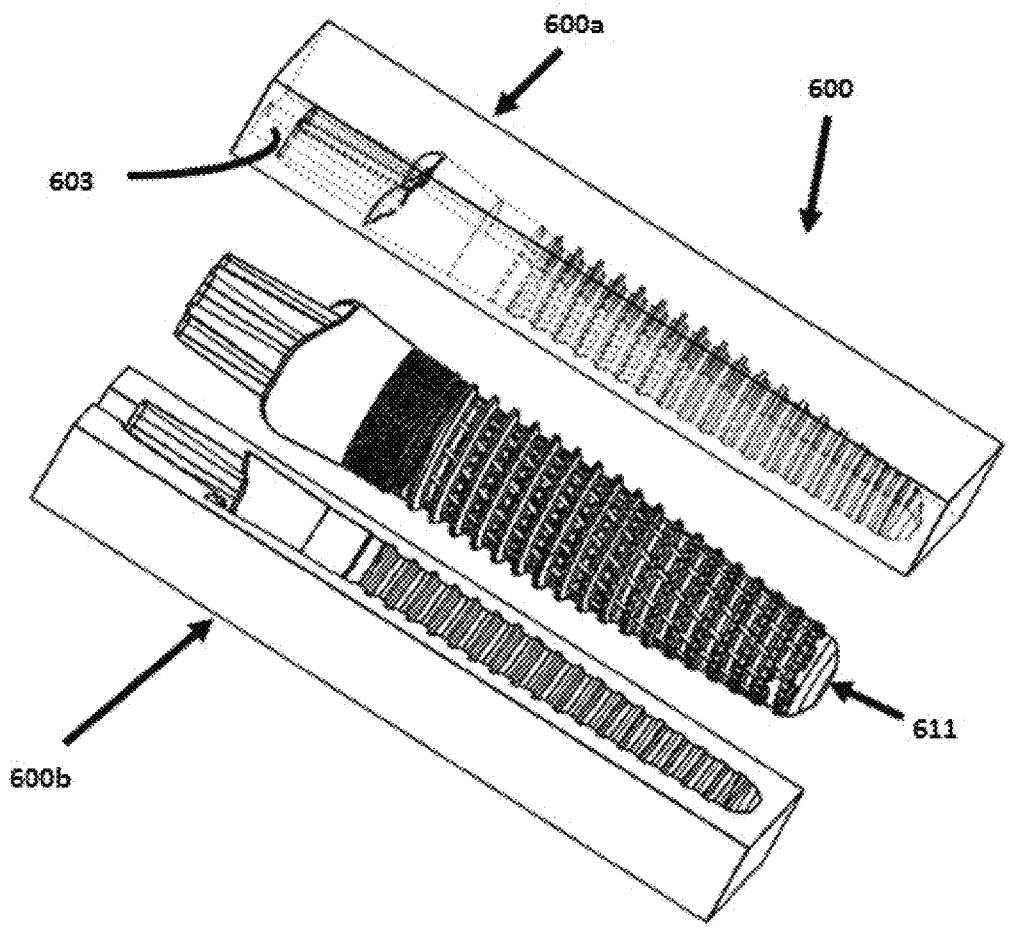

In a further alternative embodiment, as illustrated in FIGS. 15-16, spark plasma sintering is used to provide rapid sintering and densification of a dry-pressed powder compact. Spark plasma sintering (SPS), also known as plasma-activated sintering or field-assisted sintering technique (FAST), or pulsed electric current sintering (PECS), uses a combination of heat and mechanical pressure to rapidly compress and densify a finely powdered material within a heated graphite die. See, e.g., Zuhair A. Munirw and Dat V. Quach, Electric Current Activation of Sintering: A Review of the Pulsed Electric Current Sintering Process, J. Am. Ceram. Soc., 94 [1] 1-19 (2011) and R. Chaim, M. Levin, A. Shlayer and C. Estournes, Sintering and densification of nanocrystalline ceramic oxide powders: a review, Advances in Applied Ceramics 2008 VOL 107 NO 3 p. 159, both of which are incorporated herein by reference in their entirety. While the term "spark plasma sintering" is commonly used, the term is somewhat of a misnomer since neither a spark nor a plasma may be present in the process. The main characteristic of SPS is that a pulsed DC current is caused to pass directly through the graphite die and/or the powder compact, producing very rapid sintering and densification of the powdered material. In contrast to conventional sintering where heat is provided by external heating elements, in SPS heat generation is internal, facilitating very high heating rates (e.g., exceeding 500° C./min, up to 2000° C./min) and, hence, the sintering process generally is very fast (within a few minutes). The rapid speed of the SPS process allows it to sinter and densify a variety of ceramic and metal powders with nanosize particles (e.g., <=500 nm) while minimizing crystalline grain growth. Near theoretical densities (e.g., greater than 95%) can be achieved using SPS with small crystalline grain structures of only 2-3 times the average particle size of the powder compact starting material.

For example, 3 mol % Y2O3 stabilized ZrO2 nano powder may be used as a starting material such as available from Inframat Advanced Materials LLC, Manchester, Conn. (product #4039ON-9502). Of course, those skilled in the art will appreciate that a wide variety of other ceramic and/or non-ceramic powders may also be used with efficacy. It is known in classic sintering theory that densification and grain growth are two competing processes, and both of them are driven by forces that are inversely proportional to grain size. Thus, the smaller the initial powder size, the larger the densification and grain growth rates during sintering. For SPS, a finer powder will usually attain higher densities and will undergo larger grain growth than a coarser powder under identical sintering conditions. In addition, finer powders will start to densify at lower temperatures and densify at greater rates than coarser powders. Thus, the effectiveness of realizing rapid densification by applying a fast heating rate using SPS is highly dependent on the particle size of the starting powder material. Accordingly, finer powders are particularly preferred for SPS, such as nano powders having an average particle size between 20 and 50 nm and a BET surface area between 15 and 40 m2/g.

In accordance with one embodiment, a powder compact or green body is initially formed using a powder compacting press, which packs and compresses ultrafine or nano powder material into a graphite die, such as the two part die 600 illustrated in FIG. 16. The die 600 preferably has a cylindrical opening 603 at one or both ends, as illustrated. The powdered starting material is dry packed into the die and then compressed using, for example, a plunger and/or a needle inserted through the cylindrical opening 603. In accordance with one embodiment, the powder compact may be prepared by uniaxial pressing at 64 MPa followed by cold isostatic pressing (CIP) at 200 MPa producing a powder compact or green body having a density of around 43% of theoretical density. If desired, some or all of the pressing may be performed within a vacuum chamber so as to eliminate any air or other gases trapped within the green body. Alternatively, conventional colloidal (i.e., wet) processing may be used to form a reasonably dense green body that fills substantially all of the voids within the die. If wet processing is used, care should be taken to remove (e.g., debind or burn off) all of the binder material prior to SPS. Preferably, a volume of excess material is formed as part of the green body (e.g., within the cylindrical opening 603 of the die 600) in order to provide a sufficient volume of material to accommodate the desired amount compression and densification of the sintered component during the SPS process.

Once the powder compact is formed and/or compressed to a desired density, the graphite die 600 is mounted between two opposing punches (e.g., see FIGS. 15A and 15B). One or more graphite plungers are arranged to extend into the cylindrical openings (e.g., opening 603) of the die 600 so as to apply pressure to the powder compact or green body contained therein. Those skilled in the art will appreciate that additional supporting structures (not shown) may also be provided in order to adequately support the die 600 and/or prevent it from opening or cracking during pressing and sintering. A pulsed DC current is introduced through the graphite plungers and is caused to pass directly through the graphite die and/or the powder compact, heating it very rapidly (e.g., exceeding 500° C./min, up to 2000° C./min). At the same time, mechanical pressure (e.g., 40 MPa, up to 800 MPa) is applied via the graphite plungers. These conditions produce very rapid sintering and densification of the powdered material within the die cavity. The SPS conditions are preferably such that the powdered material is densely compressed and sintered to near theoretical density (e.g., greater than 95%) while assuming the precise shape and fine surface details of the die cavity. The result is a densely sintered implant 611 having small grain size and finely detailed surface features according to the particular geometries of the die 600.

If desired, the SPS process may be further adjusted and/or modified so as to produce an even more densely sintered (e.g., greater than 98.5% and up to 99.9% of theoretical density) implant 611 having desired translucence properties. The most significant factor affecting the translucence of a ceramic is porosity which typically occurs at the grain boundaries. The surface of a pore is a boundary between phases with sharply different optical characteristics, which therefore intensely reflects and refracts light. The presence of a large number of pores makes ceramics opaque. Accordingly, one way to produce a translucent ceramic implant is to more densely sinter the ceramic material in order to reduce or eliminate pores at the grain boundaries.

In one embodiment a densely sintered ceramic implant is formed by sintering a powder compact of 3YSZ powder at 1100° C. for 10 minutes at a pressure of 400 MPa, producing a highly translucent zirconia implant having a transmission coefficient tc (including both direct and diffuse transmission) of greater than about 25% measured at a wavelength of 525 nm. In another embodiment a densely sintered ceramic implant is formed by sintering a powder compact of 3YSZ powder at 1075° C. for 12 minutes at a pressure of 500 MPa, producing a highly translucent zirconia implant having a transmission coefficient tc of greater than about 33% measured at a wavelength of 525 nm. In another embodiment a densely sintered ceramic implant is formed by sintering a powder compact of 3YSZ powder at 1050° C. for 16 minutes at a pressure of 600 MPa, producing a highly translucent zirconia implant having a transmission coefficient tc of greater than about 40% measured at a wavelength of 525 nm. In another embodiment a densely sintered ceramic implant is formed by sintering a powder compact of 3YSZ powder at 1025° C. for 22 minutes at a pressure of 750 MPa, producing a highly translucent zirconia implant having a transmission coefficient tc of greater than about 60% measured at a wavelength of 525 nm. In another embodiment a densely sintered ceramic implant is formed by sintering a powder compact of 3YSZ powder at 1100° C. for 18 minutes at a pressure of 700 MPa, producing a highly translucent zirconia implant having a transmission coefficient tc of greater than about 75% at a wavelength of 525 nm.

If desired, tinting and/or coloring of the implant 611 can be provided by introducing trace impurities and/or by annealing the sintered implant in an oxidizing atmosphere (e.g., annealing in air for 1-2 hours at 800° C.). See, e.g., H. Zhang, B. Kim, K. Morita, H. Yoshida, K. Hiraga and Y. Sakka, Fabrication of Transparent Yttria by High-Pressure Spark Plasma Sintering, J. Am. Ceram. Soc., 94 [10] 3206-3210 (2011) and H. Zhang, B. Kim, K. Morita, H. Yoshida, J. Lim and K. Hiraga, Optical Properties and Microstructure of Nanocrystalline Cubic Zirconia Prepared by High-Pressure Spark Plasma Sintering, J. Am. Ceram. Soc. 94 [9] 2981-2986 (2011), both of which are incorporated herein by reference in their entirety.

Composite Materials

In accordance with another aspect of the invention, an osseointegrative implant may be fabricated from a composite material. Composite materials may generally be defined as those materials that consist of two or more fundamentally different components that are able to act synergistically to produce material properties superior to those provided by either component alone. For example, it is known that alumina ceramics can be combined with hydroxyapatite in order to achieve a composite ceramic material having higher bioactivity. See, e.g., S. Zeng, Z. Yang, P. Ling, G. Xu and W. Cao, Materials Research Society Symposium Proceedings 292 (Biomolecular Materials), 271-275 (1993). Various alumina-zirconia composites have also been investigated for enhancing biocompatibility with bone tissue. See, e.g., B. A. Konduk A. H. Ucisik, Journal of the Australasian Ceramic Society, 37(1), 63-81 (2001).

In accordance with one embodiment, an osseointegrative implant is fabricated in whole or in part by densely sintering a green body formed from a composite powder mixture of polycrystalline yttria-stabilized tetragonal zirconia and alumina comprising by weight approximately 94.4% $ZrO_2$, 5.0-5.3% $Y_2O_3$, and 0.2-0.3% $Al_2O_3$. In accordance with another embodiment, an osseointegrative implant is fabricated in whole or in part by densely sintering a green body formed from a composite powder mixture comprising by weight approximately 75% to 85% of 3 mol % yttria-stabilized zirconia $(Y_2O_3)_3 (ZrO_2)_{97}$ and approximately 15% to 25% titanium dioxide ($TiO_2$). In accordance with another embodiment, an osseointegrative implant is fabricated in whole or in part by densely sintering a green body formed from a composite powder mixture comprising approximately 85% to 95% of 3 mol % yttria-stabilized zirconia $(Y_2O_3)_3 (ZrO_2)_{97}$ and approximately 5% to 15% titanium dioxide ($TiO_2$). In accordance with another embodiment, an osseointegrative implant is fabricated in whole or in part by densely sintering a green body formed from a composite powder mixture comprising approximately 75% to 95% of 3 mol % yttria-stabilized zirconia $(Y_2O_3)_3 (ZrO_2)_{97}$ and approximately 5% to 25% of 6 mol % yttria-stabilized zirconia $(Y_2O_3)_6 (ZrO_2)_{94}$. In accordance with another embodiment, an osseointegrative implant is fabricated in whole or in part by densely sintering a green body formed from a composite powder mixture comprising approximately 75% of 3 mol % yttria-stabilized zirconia $(Y_2O_3)_3 (ZrO_2)_{97}$, approximately 15% hydroxyapatite, and approximately 10% titanium dioxide ($TiO_2$).

In each case described above and in other cases where two or more different materials are used to form a composite green body, the composition and/or the ratio of composite components may also be varied throughout the green body so as to provide various desired material properties at different locations of the finished implant (e.g., interior vs. exterior, inner threads vs. outer threads, subgingival vs. transgingival vs. supragingival, etc.) in order to enhance the overall performance characteristics of the implant. Such composite variations may be achieved in accordance with any number of well-known molding and/or forming techniques such as powder compacting, powder coating, casting, slip molding, injection molding, co-injection molding, spraying, dipping, rolling, masking, co-extrusion, multi-layer extrusion, sol-gel processing, 3D printing, and/or similar techniques.

In accordance with another aspect of the invention, a densely sintered osseointegrative implant is fabricated from a nanocomposite material prepared by the incorporation of a substantial portion by volume of carbon nanotubes in a finely powdered starting material. Carbon nanotubes (CNTs) are allotropes of carbon with a cylindrical nanostructure. CNTs are the strongest and stiffest materials yet discovered in terms of tensile strength and elastic modulus respectively. This strength results from the covalent sp2 bonds formed between the individual carbon atoms. The surface areas of CNTs can also be very high because, in the absence of agglomeration, every atom of a single walled nanotube lies on its surface. Another significant feature of CNTs is their very high aspect (length to diameter) ratio which is relevant to load transfer, heat transfer and electrical conductivity within a composite matrix.

Figure 17:
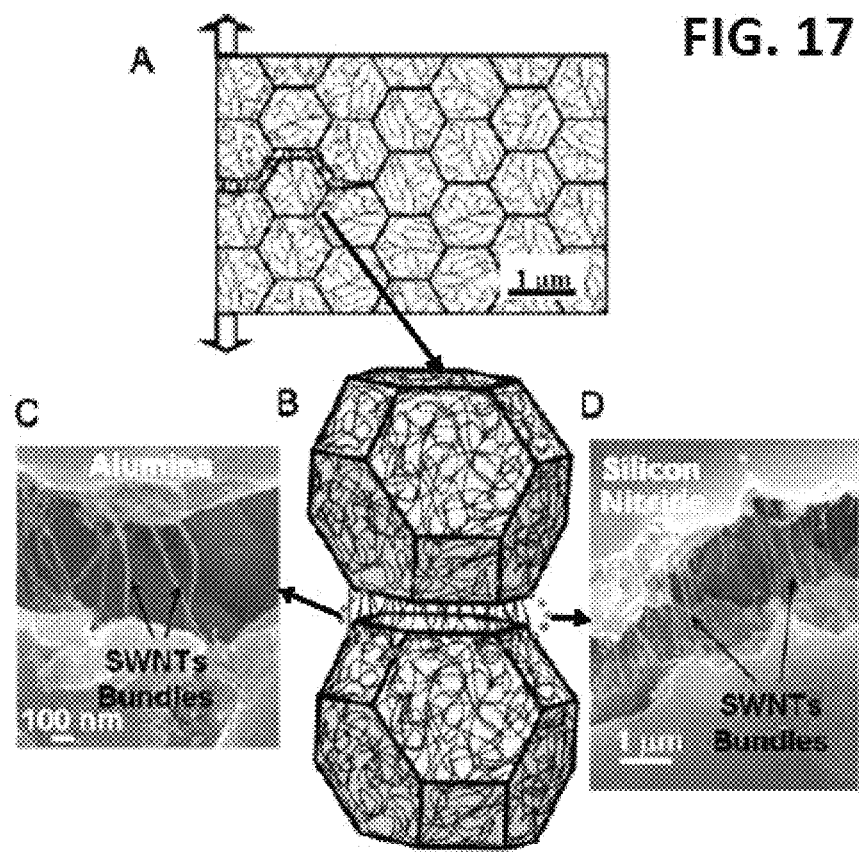
FIG. 17 is a schematic illustration of a CNT-reinforced ceramic composite material used to fabricate an implant having features and advantages in accordance with the present invention.

CNTs provide a basic building block for producing many advanced engineering composite materials having unprecedented mechanical and thermal properties, including ultra-high elastic modulus (~1 TPa), high tensile strength (~150 GPa), high thermal conductivity (~3000-6000 W/mK), and a low coefficient of thermal expansion ($2.7\times10^{-6}$/K to $4.4\times10^{-6}$/K). The outstanding mechanical properties of CNTs provide particularly attractive advantages in the context of a ceramic implant. Added as a reinforcement material to a ceramic-based material (e.g., zirconia, alumina and/or hydroxyapatite), CNTs can substantially increase the torsional and bending strength of the implant while reducing its susceptibility to stress-induced crack propagation. This phenomena is illustrated in FIG. 17. Inset (A) of FIG. 17 is a schematic illustration of a CNT-reinforced ceramic composite material which has developed an intergranular crack. Inset (B) of FIG. 17 shows a detailed view of the separated ceramic grains and the CNT bundles bridging the crack. Insets (C) and (D) of FIG. 17 are SEM images of intergranular cracks observed in a CNT-reinforced alumina composite and a CNT-reinforced silicon nitride composite, respectively, showing CNT bundles bridging the intergranular cracks of the CNT-reinforced alumina composite material. See, e.g., N. Padture, Multifunctional Composites of Ceramics and Single-Walled Carbon Nanotubes, Adv. Mater. 2009, 21, 1767-1770, incorporated herein by reference in its entirety.

Figure 18:
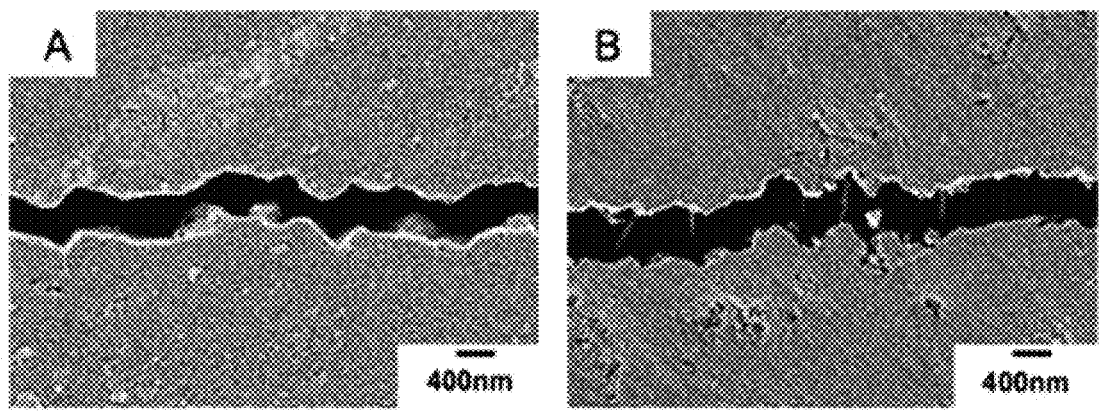
FIG. 18 is a side-by-side FESEM micrograph comparison of indentation induced crack morphology in (A) monolithic zirconia, versus (B) 1.0 wt % CNT-reinforced zirconia composite.

FIG. 18 shows comparative FESEM micrographs of indentation induced crack morphology in monolithic zirconia (inset A) and 1.0 wt % CNT-reinforced zirconia composite (inset B). As can be seen from the inset B micrograph, the 1.0 wt % CNT-reinforced zirconia exhibits a significant crack-induced toughening response caused by interfacial bonding between the CNTs and the zirconia matrix (note the CNTs bridging the fracture gap). The extent of CNTs bridging the fracture gap indicates a reduction of and/or impedance to further crack propagation, thus increasing the fracture toughness of the composite ceramic material.

Table 1 below shows that a densely sintered composite body of 3YZT having 0.5 to 5 wt % of CNTs has a shear modulus that is 5% to 40% higher than that of monolithic 3YTZ.

TABLE 1

| Material Composition | Shear Modulus (GPa) |
| --- | --- |
| 3YSZ | 78 ± 6.5 |
| 3YSZ + 0.5 wt. % CNT | 82 ± 5.4 |
| 3YSZ + 1.5 wt. % CNT | 92 ± 4.3 |
| 3YSZ + 3.0 wt. % CNT | 99 ± 3.8 |
| 3YSZ + 5.0 wt. % CNT | 107 ± 3.8 |

See, e.g., M. Mazaheri, et al., Multi-walled carbon nanotube/nanostructured zirconia composites: Outstanding mechanical properties in a wide range of temperature, Compos. Sci. Technol. (2011), incorporated herein by reference in its entirety. See also, B. Milsom et al., The effect of carbon nanotubes on the sintering behaviour of zirconia, Journal of the European Ceramic Society 32 (2012) 4149-4156 and F. Inam et al., The sintering and grain growth behaviour of ceramic-carbon nanotube nanocomposites, Composites Science and Technology 70 (2010) 947-952.

There are two main kinds of carbon nanotubes relevant to the present invention: single-walled carbon nanotubes (SWCNTs) comprising individual cylinders 1-2 nm in diameter and made up of a single rolled graphene sheet, and multi-walled carbon nanotubes (MWCNTs) comprising a multi-layered structure made up of several concentric graphene cylinders, with weak Van der Waals forces binding the inner and outer tubes together. SWCNTs are significantly smaller in diameter compared to MWCNTs and the mechanical properties may differ significantly. MWCNTs consist of nested graphene cylinders coaxially arranged around a central hollow core with interlayer separations of about 0.34 nm, similar to the interplane spacing of graphite. MWCNTs are often curled, kinked and some of them are highly twisted with each other forming big CNT bundles having strong inter-tube van der Waals attraction.

If desired, some or all of the CNTs may be decorated with nanoparticles such as Au, Pd, Pt, Ag, Ti, or TiO2. See, e.g., F. Xin et al., Decoration of carbon nanotubes with silver nanoparticles for advanced CNT/polymer nanocomposites, Composites: Part A 42 (2011) 961-967, incorporate herein by reference in its entirety. Advantageously, decorated CNT's may be used to increase the electrical conductivity of the ceramic composite material, alter the color of the CNT (e.g., change it from black to silver or gold), improve biocompatibility, improve antibacterial characteristics, and/or improve dispersion and interfacial bonding between the CNTs and the ceramic base material. See, e.g., S. Ou et al., Research of antibacterial activity on silver containing yttria-stabilized-zirconia bioceramic, Ceramics International 39 (2013) 3591-3596, and E. Fortunati, Carbon nanotubes and silver nanoparticles for multifunctional conductive biopolymer composites, CARBON 49 (2011) 2370-2379. A wide variety of suitable SWCNT and MWCNT materials, both decorated and undecorated, are commercially available from sources such as Nanointegris Technologies Inc. in Menlo Park, Calif. and Sigma-Aldrich Corporation in St. Louis, Mo.

In accordance with one embodiment, an osseointegrative implant is fabricated in whole or in part by densely sintering a green body formed from a composite powder mixture comprising approximately 95.0 to 97.5 wt % of powdered ceramic material such as 3 mol % yttria-stabilized zirconia (Y2O3)3 (ZrO2)97 and approximately 2.5 to 5.0 wt % of CNTs. In accordance with another embodiment, an osseointegrative implant is fabricated in whole or in part by densely sintering a green body formed from a composite powder mixture comprising by approximately 97.5 to 99.5 wt % of powdered ceramic material such as 3 mol % yttria-stabilized zirconia (Y2O3)3 (ZrO2)97 and approximately 0.5 to 2.5 wt % of SWCNTs. In accordance with another embodiment, an osseointegrative implant is fabricated in whole or in part by densely sintering a green body formed from a composite powder mixture comprising approximately 97.5 to 98.5 wt % of powdered ceramic material such as 3 mol % yttria-stabilized zirconia (Y2O3)3 (ZrO2)97 and approximately 1.5 to 2.5 wt % of MWCNTs. In accordance with another embodiment, an osseointegrative implant is fabricated in whole or in part by densely sintering a green body formed from a composite powder mixture comprising approximately 97.5 to 98.5 wt % of powdered ceramic material such as 3 mol % yttria-stabilized zirconia (Y2O3)3 (ZrO2)97 and approximately 1.5 to 2.5 wt % of MWCNTs decorated with an electrically conductive metal such as silver, gold or titanium. In accordance with another embodiment, an osseointegrative implant is fabricated in whole or in part by densely sintering a green body formed from a composite powder mixture comprising approximately 97.5 to 98.5 wt % of 3 mol % yttria-stabilized zirconia (Y2O3)3 (ZrO2)97 and approximately 1.5 to 2.5 wt % of silver-decorated CNTs.

Preferably, the CNT material is processed and mixed with the ceramic base powder material in such a way as to ensure a substantially homogeneous dispersion of CNTs within the composite mixture prior to sintering. For example, this may involve pre-treatment and/or chemical surface modification of the CNTs to improve dispersion within either a colloidal suspension or dry powder mixture. Advantageously, the unique flexible nature of CNTs allows them bend and pass through spaces between nanopowders and/or wrap around them. Any CNT agglomerates are preferably dispersed and/or removed prior to green body formation and the remaining individual nanotubes are thoroughly mixed and distributed uniformly throughout the composite mixture. Good dispersion and interfacial bonding between the CNTs and the ceramic base material is important in order to achieve desired mechanical and electrical properties in the post-sintered ceramic composite material.

Surface Modifications

Optionally, the outer surface of the implant or any portion thereof may be coated, anodized, treated, sandblasted, etched and/or otherwise modified so as to provide a desired surface roughness, surface chemistry, biocompatibility and/or bioactivity. In one embodiment, particles of titanium and/or titanium oxide are infused with the outer surface of at least the bone-engaging portions of a ceramic implant by electrical discharge machining, as described in more detail below, creating a strongly bonded titanium oxide layer up to 20 μm thick and having unique roughness and porosity characteristics favorable for promoting rapid and/or more thorough bone osseointegration (see, e.g. the SEM micrograph inset shown in FIG. 21).

Electrical discharge machining (EDM) is an ablative material removal process that uses high-voltage electrical discharges passing through a dielectric fluid to erode and remove material from an electrically-conductive surface of a workpiece. During the EDM process the workpiece surface undergoes rapid melting and vaporization at the contact point of each electric discharge followed by rapid cooling and carrying away of ejected debris by the dielectric fluid. EDM is typically used to cut and/or form complex shapes in a hardened metal component such as a die or a mold that is otherwise difficult to machine using conventional cutting tools. EDM can also been used for surface modification, surface hardening and/or depositing various desired coatings on the outer surface of an electrically-conductive component. This latter process, also called electric discharge coating (EDC), can be used to deposit strongly-bonded coatings of material up to 20 μm thick.

In one embodiment, EDC is used to create a strongly-bonded titanium oxide layer on the outer surface of at least the bone-engaging portions of a ceramic implant. Preferably, the relevant portions of the implant are formed and/or treated so as to have a specific electrical resistance of 300 Ω-cm or less. For example, the electrical resistivity of ZrO2 can be reduced from in excess of 10E12 Ω-cm to about 100 Ω-cm by incorporating 0.1 wt % of SWCNT in the powder mixture that is used to form the green body or powder compact, as disclosed herein. Those skilled in the art will appreciate that well-dispersed carbon nanotubes form an interconnected percolation network through the insulating ZrO2 matrix such that the post-sintered CNT-ZrO2 composite ceramic exhibits an overall desired electrical conductivity that is sufficiently high to support the EDC process. Alternatively, as discussed in more detail herein in connection with FIG. 13, the interconnected porous structure evolved through water debinding of the implant green body may be used as a channel to introduce electrically conductive ions and/or particles of gold, silver, titanium, carbon, CNTs, and/or other electrically-conductive particles sufficiently small in size such that at least some of the particles enter and remain lodged within in the porous surface of the green body and/or diffuse interiorly to a desired depth to provide sufficient electrical conductivity at the surface of the post-sintered component to support the EDC process described herein.

As illustrated in FIGS. 19-22, the workpiece to be coated (in this case an electrically conductive ceramic implant) is placed within a dielectric fluid such as deionized water (DI) and brought within close proximity of a high-potential titanium electrode. The electrode may be shaped and/or positioned so as to provide a substantially uniform spark gap between the opposing surfaces of the electrode and the workpiece. For example, FIGS. 22A and 22B illustrate one possible configuration of a pair of closely fitting electrodes 650 (anode+cathode) configured for selectively coating only the bone-engaging portions of an implant 611 with a fused layer of titanium oxide using an EDC process as described herein. The closely fitting electrodes 650 generally comprise an anode portion 651 and a cathode portion 653, each shaped and configured to accommodate the implant 611 desired to be coated. If desired, the interior portions of the cathode portion 653 may be shaped to closely match the outer contours of the implant 611 so as to provide a substantially uniform spark gap between the outer implant surface to be coated and the cathode portion 653. This is more of a concern where the spark gap is small. For larger spark gaps the uniformity of the spark gap and the particular size, shape and positioning of the cathode is less important.

Figure 22A:
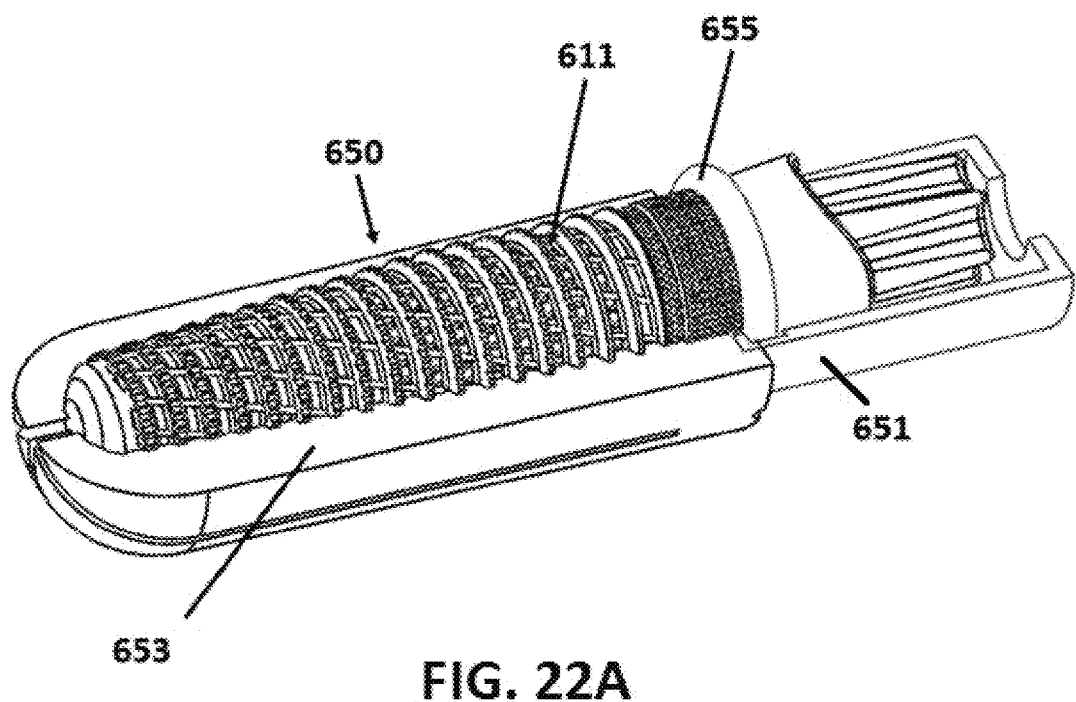
FIG. 22A is a partial cross-sectional view of an EDC electrode system having features and advantages in accordance with the present invention configured for selectively coating the bone-engaging portions of an implant with a fused layer of titanium oxide.
Figure 22B:
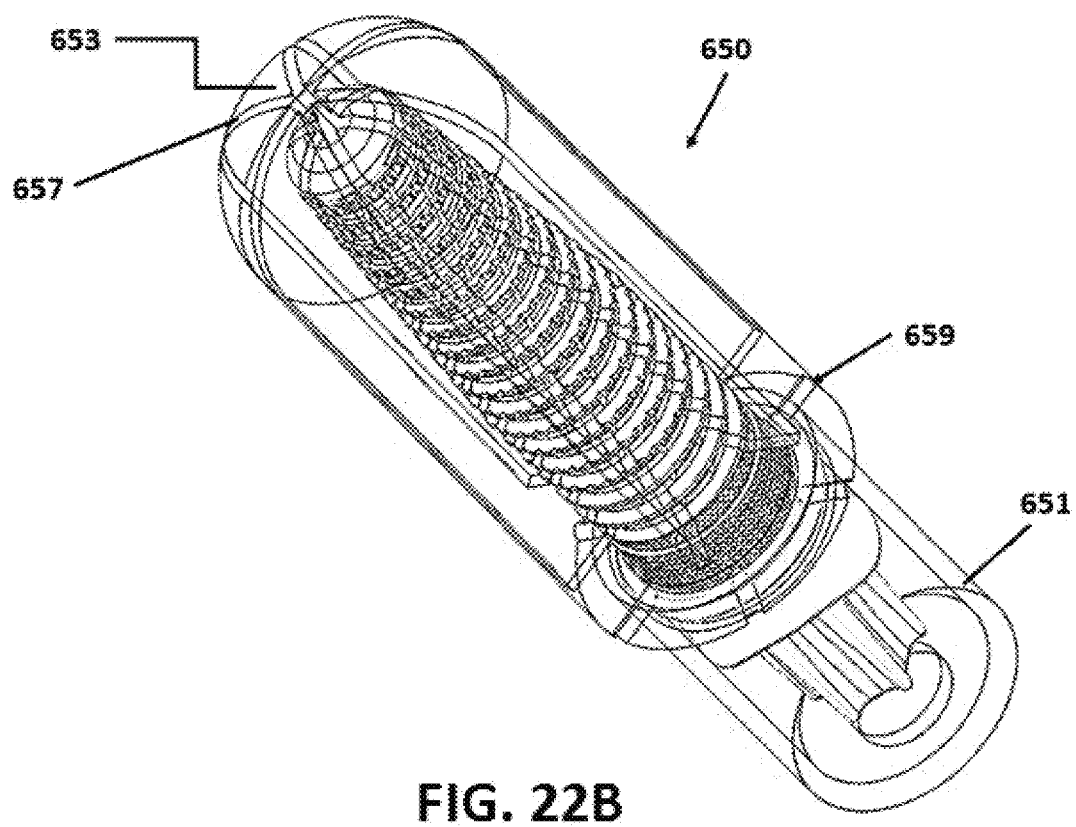
FIG. 22B is a partially-transparent assembled isometric view of the EDC electrode system of FIG. 22A.

The anode portion 651 is preferably shaped and configured to grip and hold the implant 611 and provide sufficient electrical connection to allow substantially arc-free current flow between the anode portion 651 and at least one electrically-conductive portion of the implant 611. If desired, an optional O-ring seal 655 may be provided between the anode portion 651 and the implant 611 in order to mask or shield selected portions of the implant. The anode portion 651 and the cathode portion 653 are also preferably insulated from one another by an electrical insulating barrier (not shown) in order to prevent current flow and/or arcing between the anode portion 651 and the cathode portion 653. One or more vents 657, 659 may be provided in the anode portion 651 and/or the cathode portion 653, as illustrated in FIG. 22B, in order to provide adequate inflows and outflows of dielectric fluid during the EDC process. Optionally, the implant 611 and/or the cathode 653 may be rotated and/or translated back-and-forth or side-to-side to help ensure substantial uniformity of coverage over the entire implant surface desired to be coated.

During the EDC process an electrical current is caused to flow from the titanium electrode (cathode) to the workpiece (anode) causing high-voltage arcing through the dielectric fluid, as illustrated in FIG. 19. The high-voltage arcing produces rapid melting and vaporization of both the titanium electrode and the workpiece at the arc contact points of each electric discharge followed by rapid quenching and cooling by the dielectric fluid. This in turn results in the formation of minute craters and the ejection of titanium and titanium oxide particles and ceramic debris into the dielectric fluid. Titanium oxide (TiO2) is created through a spark-initiated chemical reaction between the eroded titanium electrode material and the cracked oxygen from the surrounding decomposed DI water. As the EDC process continues, some of the fluid suspended titanium and/or titanium oxide particles near the workpiece surface are also melted and/or vaporized by the high-voltage arcing, creating a spattered surface layer on the exposed outer surface of the implant, as illustrated in FIG. 21. Further arcing causes portions of the spattered surface layer and the underlying ceramic substrate to melt eventually forming a recast layer of ceramic material infused with particles of titanium oxide. The spattered surface area and the recast layer thus become inseparably fused to the underlying ceramic substrate, as illustrated in FIG. 21.

To increase and/or control the erosion rate of the titanium cathode, it is preferably formed from a green powder compact and/or a partially- or fully-sintered compact of powdered titanium. Titanium powders having an average particle size of between about 45 µm and 180 µm are preferred, although finer or courser powders may also be used with efficacy (e.g., ranging between about 0.5 µm and 0.25 mm). Electrodes formed from finer powders typically lead to faster erosion of the cathode and result in more intricate and higher-surface-area roughness and porosity characteristics of the titanium oxide coating layer. Smaller size particles also create greater suspension effect in the dielectric fluid (e.g., DI water) as the cathode erodes, allowing for more uniform and/or higher concentrations of titanium oxide particles in the dielectric fluid.

Optionally, as illustrated in FIGS. 20 and 21, pure titanium and/or titanium oxide powder(s) may be added directly to the dielectric fluid in order to reduce the insulating strength of the dielectric fluid, increase the spark gap between the electrode and the workpiece and increase the coating rate, thickness and/or quality. See, e.g., G. Prihandana et al., Effect of micro-powder suspension and ultrasonic vibration of dielectric fluid in micro-EDM processes, Int. J. Mach. Manu. 49 (2009) 1035-1041, incorporated herein by reference in its entirety. The added powdered materials can be maintained in suspension via one or more mechanical agitators, such as a fluid pump, mechanical stirring system and/or ultrasonic agitator. The electrode may also be moved reciprocally (up-and-down and/or side-to-side) in order to stabilize the machining process and/or help flush powder from the gap and maintain it in fluid suspension. This so-called powder mixed electric discharge coating (PMEDC) process provides added flexibility in the coating process and permits the ability to more precisely control the thickness, quality and surface finish of the resulting titanium oxide coating. For example, a combination of fine, medium and course titanium and/or titanium oxide powders (and/or other powdered materials) may be added to the dielectric fluid in various ratios (e.g., 50/35/15 fine/medium/course) in order to provide a coated surface characterized by a unique combination of large, medium and small craters and random spatter-like surface features that promote rapid and/or more thorough osseointegration of the implant with live bone tissue. Optionally, titanium and/or titanium oxide powder having an average particle size less than 36 µm may be added to the dielectric fluid (e.g., DI water) at a concentration of 50 g/l. As a further option, pure titanium powder having an average particle size less than 100 µm may be added to the dielectric fluid (e.g., DI water) at a concentration of 25-40 g/l.

In an alternative embodiment, a modified PMEDC process is used to create a fused titanium oxide layer on the outer surface of an otherwise non-electrically-conductive ceramic implant. According to this alternative embodiment a first layer of electrically conductive substance is applied to the surface of the implant to form a temporary or auxiliary electrode capable of initiating the PMEDC process. See, e.g., G. Kucukturka et al., A new method for machining of electrically nonconductive workpieces using electric discharge machining technique, Machining Science and Technology: An International Journal, Vol. 14, Issue 2, pgs. 189-207 (2010), and US20100038344 to Forster et al, each incorporated herein by reference in their entirety. For example, the bone-engaging portions of a non-conductive ceramic implant may be coated with a thin conductive layer (CL) of biocompatible material such as, for example, a 3-5 µm thick layer of titanium nitride (TiN) or titanium carbonitride (TiCN). Titanium nitride is non-toxic, meets FDA guidelines and has been used in a wide variety of medical devices such as scalpel blades, orthopedic bone saw blades and hip prostheses. It has a specific electrical resistivity of between 30 and 70 µΩ•cm, providing suitable surface conductivity for sustaining the EDC process. TiN or TiCN can be readily applied to the non-conductive surface of a ceramic implant by physical vapor deposition (e.g., sputter coating, cathodic arc deposition or electron beam heating) and/or chemical vapor deposition. In both methods, pure titanium is sublimated and reacted with nitrogen in a high-energy, vacuum environment and the resulting vapors are caused to condense on the cooler exposed surfaces of the ceramic implant. During subsequent EDC and/or PMEDC processing (such as described above) the initial spark discharge formations occur between the titanium electrode and the CL. The CL may be partially or fully ablated and/or eroded in the process. However, as the EDC and/or PMEDC process continues, a spattered surface layer of titanium oxide develops on the surface of the implant providing sufficient surface conductivity to sustain the EDC coating process.

According to the various surface modification techniques disclosed and described herein, particles of titanium and/or titanium oxide are able to be infused with the outer surface of the bone-engaging portions of a ceramic or ceramic composite implant, creating a fused titanium oxide layer up to 20 µm thick having unique roughness and porosity characteristics favorable for promoting rapid and/or more thorough bone osseointegration. As illustrated in more detail in FIG. 21 the resulting modified implant surface is characterized by a dense variety of pits and craters formed by melting, spalling and spattering of the coated surface created during the EDC process. In cross section the modified implant surface can generally be divided into three layers consisting of a spattered surface layer, a recast layer, and a heat affected zone. The spattered surface layer is formed as molten material is displaced, ejected and/or deposited on the implant surface with each spark discharge. Immediately following each spark discharge, the implant surface is rapidly cooled by the dielectric fluid, resulting in solidification of molten material and thermal-stress-induced fracturing, palling or pitting. The next layer is formed by rapid melting and solidification of the surface immediately below the spattered surface layer and is referred to as a recast layer. The recast layer mainly comprises the base ceramic substrate material (e.g., zirconia) but may also include some embedded titanium oxide particles, which are captured and/or mixed in with the recast layer. The layer immediately below the recast layer is the heat affected zone. In this layer, the underlying base material is typically not melted and there is substantially no mixing or capturing of titanium oxide parties. However, there may be some crystalline growth and/or restructuring caused by intense localized heat introduced by the EDM process.

APPLICATIONS AND EXAMPLES

Embodiments of the present invention may be employed, produced and carried out in a wide variety of clinical and commercial applications, as will be readily apparent to those skilled in the art. The following specific examples are provided for purposes of illustration and for better understanding of the invention and should not be taken as limiting the invention in any way.

Example 1

A single-stage threaded implant is formed having one or more of the features and geometries as illustrated and described above in connection with FIGS. 1-8. The implant is formed by conventional machining and/or grinding of a solid cylinder of pure titanium or titanium alloy material.

Example 2

A single-stage press-fit implant is formed having one or more of the features and geometries as illustrated and described above in connection with FIGS. 11A-C. The implant is formed by conventional machining and/or grinding of a solid cylinder of pure titanium or titanium alloy material.

Example 3

A two-stage threaded ceramic implant is formed having one or more of the features and geometries as illustrated and described above in connection with FIGS. 9-10. At least one portion of the implant is formed by conventional machining and/or grinding of a solid cylinder of pure titanium, titanium alloy or stainless steel material. At least the outer bone-engaging portion of the implant is formed by densely sintering a ceramic green body formed by slip casting, powder compacting or injection molding a ceramic feedstock comprising 3 mol % yttria-stabilized powdered zirconia having an average particle size of about 0.16 µm.

Example 4

A dental implant is formed according any of the Examples 1-3 wherein a circumferentially extending pattern of 50 to 250 discrete raised and/or sunken surface features are formed on an outer bone-engaging surface of the implant and wherein each discrete surface feature has a maximum height or depth relative to the implant surface of less than about 0.1 mm.

Example 5

A dental implant is formed according any of the Examples 1-4 wherein a pattern of raised and/or sunken surface features form a geometric pattern on an outer bone-engaging surface of the implant so as to provide a directionally-dependent coefficient of sliding friction for the implant that is at least 30% less in the implant insertion direction than in the implant extraction direction.

Example 6

A dental implant is formed according to any of the Examples 1-5 wherein the implant is formed at least in part by hot forging and/or cold forging a partially-shaped blank of pure titanium or titanium alloy material.

Example 7

A dental implant is formed according to any of the Examples 1-6 wherein the implant is formed at least in part by sintering a green body formed by slip casting, powder compacting or injection molding a feedstock comprising a powdered titanium or titanium alloy material having an average particle size of between 10 and 36 µm.

Example 8

A dental implant is formed according to any of the Examples 1-7 wherein the implant is formed at least in part by sintering a green body formed by slip casting, powder compacting or injection molding a ceramic feedstock comprising 3 mol % yttria-stabilized powdered zirconia having an average particle size of about 0.16 µm.

Example 9

A dental implant is formed according to any of the Examples 1-8 wherein the entire implant is molded or powder compacted in green stage to substantially its final geometry (enlarged to account for shrinkage during subsequent sintering), including substantially all final surface texturing and other desired surface features. The green stage implant is then debinded (if a binder is used) and sintered in one or more sintering operations to produce a finished dental implant product that does not require any grinding or machining operations.

Example 10

A dental implant is formed according to any of the Examples 1-9 wherein the implant is formed at least in part by injection molding a ceramic feedstock comprising powdered polycrystalline yttria-stabilized tetragonal zirconia comprising by weight approximately 94.4% $ZrO2$, 5.0-5.3% $Y2O3$ and 0.2-0.3% $Al2O3$ and having an average particle size between 0.05 and 0.25 µm and a BET surface between about 8.0 and 40.0 m2/g. The powdered YSZ is first coated with stearic acid by ball-milling for 4 hours with 3 vol % stearic acid solution. The SA-coated powder is then thoroughly mixed with a POM binder using a twin screw kneader until a solids loading of about 48% is reached.

Example 11

A dental implant is formed according to any of the Examples 1-10 wherein the implant is formed by sintering a debound green body. Prior to sintering, the debound green body is fully or partially immersed in an aqueous solution containing ions and/or particles of silver, gold, titanium, zirconia, YSZ, α-tricalcium phosphate, hydroxyapatite, carbon, carbon nanotubes, and/or other particles sufficiently small in size such that at least some of the particles enter and remain lodged in the porous surface of the green body and/or diffuse interiorly to a desired depth.

Example 12

A dental implant is formed according to any of the Examples 1-11 wherein the implant is formed by sintering a debound green body. Prior to sintering, the debound green body is fully or partially immersed in a colloidal solution containing particles of carbon, carbon nanotubes, and/or other carbon-based particles such that at least some of the particles enter and remain lodged in the porous surface of the green body and/or diffuse interiorly to a desired depth. The green body is then fully sintered in a vacuum chamber or other oxygen free environment. After sintering the implant is heated in an oxygen environment until substantially all of the carbon-based particles are fully oxidized and/or burned off leaving a porous outer surface having improved biological compatibility and/or osseointegration characteristics.

Example 13

A dental implant is formed according to any of the Examples 1-12 wherein the implant is formed at least in part by spark plasma sintering a powder compact formed by compacting finely powdered 3-mol % yttria-stabilized zirconia having an average particle size between about 10 and 50 nm and a BET surface area between about 15 and 75 m2/g. The powder compact is pressed into a graphite die by uniaxial pressing at 64 MPa followed by cold isostatic pressing at 200 MPa producing a compacted green body having a density of around 43% of theoretical density. A pulsed DC current is introduced through a pair of graphite plungers and is caused to pass directly through the powder compact, heating it at a rate exceeding 500° C./min. Once a sintering temperature of 1050° C. is reached mechanical pressure of up to 400 MPa is applied until the powdered material is densely compressed and sintered to a final density between about 96.5% and 99.9% of theoretical density, resulting in a densely sintered zirconia implant having an average grain size of about 0.75 μm in diameter and detailed surface features according to the internal geometries of the graphite die.

Example 14

A dental implant is formed according to any of the Examples 1-13 wherein at least the supragingival portions of the implant have greater than 75% translucence to visible light. The implant is formed at least in part by spark plasma sintering a powder compact formed by compacting finely powdered 3-mol % yttria-stabilized zirconia having an average particle size between about 5 and 30 nm and a BET surface area between about 20 and 100 m2/g. The powder compact is pressed into a graphite die by uniaxial pressing at 64 MPa followed by cold isostatic pressing at 200 MPa producing a compacted green body having a density of around 43% of theoretical density. A pulsed DC current is introduced through a pair of graphite plungers and is caused to pass directly through the powder compact, heating it at a rate exceeding 500° C./min. Once a sintering temperature of 1100° C. is reached mechanical pressure of up to 800 MPa is applied for about 10 minutes until the powdered material is densely compressed and sintered to a final density greater between about 99.5% and 99.9% of theoretical density, resulting in a densely sintered zirconia implant having desired translucence properties.

Example 15

A dental implant is formed according to any of the Examples 1-14 wherein the implant is formed at least in part by densely sintering a green body formed from a composite powder mixture comprising approximately 98.0 wt % of powdered 3-mol % yttria-stabilized zirconia (Y2O3)3 (ZrO2)97 and approximately 2.0 wt % of SWCNTs.

Example 16

A dental implant is formed according to any of the Examples 1-15 wherein the implant is formed at least in part by densely sintering a green body formed from a composite powder mixture comprising approximately 97.5 wt % of powdered 3-mol % yttria-stabilized zirconia (Y2O3)3 (ZrO2)97 and approximately 2.5 wt % of MWCNTs decorated with silver, gold and/or titanium.

Example 17

A dental implant is formed according to any of the Examples 1-16 wherein at least the bone-engaging surfaces of the implant are surface modified by electrical discharge machining, to create a strongly bonded 12 μm thick titanium oxide layer having desired surface roughness and porosity characteristics favorable for promoting implant osseointegration.

Example 18

A dental implant is formed according to any of the Examples 1-17 wherein at least the bone-engaging surfaces of the implant are surface modified by a PMEDC process to create a strongly bonded 16 μm thick titanium oxide layer having desired surface roughness and porosity characteristics. A titanium cathode is used and is formed from a green powder compact of pure titanium powder having an average particle size of about 120 μm. Dionized water is used as the dielectric fluid. Titanium oxide powder having an average particle size of 25 μm is added to the dionized water and is maintained in fluid suspension at a concentration of 50 g/l using a pump having a flow rate of about 15 L/min. The PMEDC process is continued until at least a 16 μm thick titanium oxide layer is attained.

Example 19

A dental implant is formed according to any of the Examples 1-18 wherein at least a portion of the implant is formed from a non-electrically-conductive ceramic and wherein at least the bone-engaging surfaces of the implant are surface modified by a PMEDC process to create a strongly bonded 18 μm thick titanium oxide layer having desired surface roughness and porosity characteristics. An initial coating of 3.5 μm thick titanium nitride (TiN) is applied to the bone-engaging surfaces of the ceramic implant by physical vapor deposition in order to form a temporary conductive layer for initiating the PMEDC process. During PMEDC a titanium cathode is used which is formed from a partially-sintered powder compact of pure titanium powder having an average particle size of about 100 μm. Dionized water is used as the dielectric fluid. Pure titanium powder having an average particle size of 100 μm is added to the dionized water and is maintained in fluid suspension at a concentration of 40 g/l using a pump having a flow rate of about 20 L/min. The PMEDC process is continued until an 18 μm thick titanium oxide layer is attained.

Other Applications and Modifications

Although this invention has been disclosed in the context of certain preferred embodiments and examples, those skilled in the art will appreciate that the present invention extends beyond the specifically disclosed embodiments to other alternative embodiments and/or uses of the invention and obvious modifications and equivalents thereof. Thus, it is intended that the scope of the present invention should not be limited by the particular preferred embodiments disclosed herein, but should be determined only by a fair reading of the claims that follow.

What is claimed is:

1. A method for manufacturing a threaded osseointegrative surgical implant, said method comprising:
   injecting a feedstock into a mold cavity, said feedstock comprising a powdered material suspended in a heated liquid binder, said mold cavity comprising at least one female thread and at least one textured interior surface;
   causing or allowing said injected feedstock to cool in said mold cavity until it forms a substantially solid green body having sufficient strength for demolding, said green body comprising a mating male thread corresponding to said at least one female thread and a textured exterior surface corresponding to said at least one textured interior surface;
   removing said green body from said mold cavity by rotating and unscrewing said green body;
   debinding said green body to remove said binder; and
   sintering said debound green body to form a threaded osseointegrative surgical implant having a mating male threadcorresponding to said at least one female thread in said mold cavity and a textured exterior surface corresponding to said at least one textured interior surface in said mold cavity and wherein said textured exterior surface of said threaded osseointegrative surgical implant has a peak-to-peak surface roughness (SZ) of between 23.91 µm and 36.27 µm.

2. The method of claim 1, wherein said at least one textured interior surface comprises a plurality of bumps or dimples distributed in a regular spaced pattern and wherein said textured exterior surface of said threaded osseointegrative surgical implant comprises a corresponding pattern of bumps or dimples with an average height or depth between 0.03 mm and 0.15 mm.

3. The method of claim 2, wherein said feedstock comprises powdered 3-mol % yttria-stabilized zirconia (Y2O3)3 (ZrO2)97.

4. The method of claim 3, wherein said powdered yttria-stabilized zirconia has an average particle size of between 0.05 and 0.25 µm and a BET surface area of between about 8.0 and 40.0 m2/g.

5. The method of claim 2, wherein said feedstock comprises ultrafine powered yttria-stabilized zirconia suspended in a water-soluble binder system with a solids loading of about 48%.

6. The method of claim 2, wherein said feedstock comprises powdered titanium.

7. The method of claim 2, further comprising densifying said threaded osseointegrative surgical implant by hot isostatic pressing at a pressure between 150 MPa and 250 MPa and a temperature between 1200° C. and 1350° C.

8. A method for manufacturing a restorative dental implant, said method comprising:
   injecting a feedstock into a mold cavity, said feedstock comprising a first powdered material suspended in a liquid binder, said mold cavity comprising an internal geometry and surface texture corresponding to a desired external geometry and surface texture of said restorative dental implant;
   causing or allowing said injected feedstock to cool in said mold cavity until it forms a substantially solid green body having sufficient strength for demolding, said green body having an external geometry and surface texture corresponding to said internal geometry and surface texture of said mold cavity;
   removing said green body from said mold cavity;
   debinding said green body to form a debound green body having a fluid-permeable interconnected porous structure;
   exposing at least a portion of said debound green body to a colloidal mixture comprising a second powdered material suspended in a fluid and allowing said second powdered material to infuse said fluid-permeable interconnected porous structure to a desired depth; and
   sintering said infused debound green body to form a restorative dental implant having an external geometry and surface texture corresponding to said internal geometry and surface texture of said mold cavity and at least one surface infused with particles comprising said second powdered material.

9. The method of claim 8, wherein said first powdered material is selected from the group consisting of zirconia, yttria-stabilized zirconia, alumina, and titanium.

10. The method of claim 8, wherein said second powdered material is selected from the group consisting of silver, titanium, zirconia, yttria-stabilized zirconia, silica, boron, tricalcium phosphate, hydroxyapatite, carbon, and carbon nanotubes.

11. The method of claim 8, further comprising dissolving or chemically removing said infused particles from said at least one surface to produce a porous surface.

12. The method of claim 8, wherein said internal surface texture of said mold cavity comprises a plurality of bumps or dimples distributed in a regular spaced pattern and wherein said external surface texture of said restorative dental implant comprises a corresponding pattern of bumps or dimples with an average height or depth between 0.03 mm and 0.15 mm.

13. The method of claim 8, wherein said internal surface texture of said mold cavity is configured to produce a restorative dental implant having a corresponding external surface texture with frictionally anisotropic bone-engaging surfaces.

14. The method of claim 8, wherein said internal surface texture of said mold cavity is configured to produce a restorative dental implant having a corresponding external surface texture with a peak-to-peak surface roughness (SZ) of between 23.91 µm and 36.27 µm.

* * * * *